United States Patent
Tanaka et al.

(10) Patent No.: US 9,129,384 B2
(45) Date of Patent: Sep. 8, 2015

(54) MEDICAL IMAGE PROCESSING DEVICE

(71) Applicant: OLYMPUS MEDICAL SYSTEMS CORP., Tokyo (JP)

(72) Inventors: Kenichi Tanaka, Kariya (JP); Sawako Shibata, Tama (JP); Yusuke Tomoto, Tokyo (JP); Hirokazu Nishimura, Hachioji (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 0 days.

(21) Appl. No.: 14/300,406

(22) Filed: Jun. 10, 2014

(65) Prior Publication Data

US 2014/0334698 A1    Nov. 13, 2014

Related U.S. Application Data

(63) Continuation of application No. PCT/JP2013/079884, filed on Nov. 5, 2013.

(30) Foreign Application Priority Data

Nov. 7, 2012  (JP) ................................. 2012-245667
Dec. 5, 2012  (JP) ................................. 2012-266445

(51) Int. Cl.
*G06K 9/00*    (2006.01)
*G06T 7/00*    (2006.01)
(Continued)

(52) U.S. Cl.
CPC ............. *G06T 7/0081* (2013.01); *A61B 1/0005* (2013.01); *A61B 1/00009* (2013.01); *A61B 1/0646* (2013.01); *G06T 2207/30004* (2013.01)

(58) Field of Classification Search
None
See application file for complete search history.

(56) References Cited

U.S. PATENT DOCUMENTS 6,430,432 B1 *  8/2002  Wilting et al. ................. 600/425
2006/0050966 A1  3/2006  Nishimura et al.
(Continued)

FOREIGN PATENT DOCUMENTS

EP    1568307 A1    8/2005
EP    2423875 A1    2/2012
(Continued)

OTHER PUBLICATIONS

Kudo, Shin-ei, et al., "Magnifying Endoscopic Observation and Diagnosis of Depth of Invasion of Colorectal Tumor—Consensus at the Hakone Symposium Regarding Type V sub-classification", Stomach and Intestines, Apr. 2004, vol. 39, No. 5, pp. 747-752, together with an English language translation.
(Continued)

*Primary Examiner* — Bhavesh Mehta
*Assistant Examiner* — Andrew Moyer
(74) *Attorney, Agent, or Firm* — Scully, Scott, Murphy & Presser, P.C.

(57) ABSTRACT

A medical image processing device includes an input section to which a biological mucous membrane image obtained by picking up an image of a biological mucous membrane is inputted, a region extracting section that extracts a mucous membrane microstructure region corresponding to a mucous membrane microstructure from the inputted biological mucous membrane image, a closed region identifying section that identifies at least one closed region regarded as being surrounded by the mucous membrane microstructure region, and a unit region setting section that sets a biologically histological unit region on the basis of the mucous membrane microstructure region and the closed region.

18 Claims, 44 Drawing Sheets

(51) Int. Cl.
    *A61B 1/00*     (2006.01)
    *A61B 1/06*     (2006.01)

(56) References Cited

U.S. PATENT DOCUMENTS

| | | | |
|---|---|---|---|
| 2009/0074269 A1* | 3/2009 | Nishimura et al. | 382/128 |
| 2009/0074272 A1* | 3/2009 | Lu et al. | 382/128 |
| 2011/0245642 A1* | 10/2011 | Minetoma | 600/324 |
| 2012/0051654 A1 | 3/2012 | Kitamura et al. | |
| 2012/0076373 A1 | 3/2012 | Tomoto | |
| 2012/0296220 A1 | 11/2012 | Tanaka | |

FOREIGN PATENT DOCUMENTS

| | | |
|---|---|---|
| EP | 2502547 A1 | 9/2012 |
| EP | 2567651 A1 | 3/2013 |
| JP | 02-124131 A | 5/1990 |
| JP | 2918162 B2 | 7/1999 |
| JP | 4409166 B2 | 2/2010 |
| JP | 4451460 B2 | 4/2010 |
| JP | 2012-045055 A | 3/2012 |
| JP | 5011453 B2 | 8/2012 |
| JP | 5139606 B2 | 2/2013 |
| WO | WO 2004049923 A1 | 6/2004 |
| WO | WO 2012002012 A1 | 1/2012 |
| WO | WO 2012105141 A1 | 8/2012 |

OTHER PUBLICATIONS

Niwa, Hirofumi, et al., "Colon", Image-enhance Endoscopy, 2010, pp. 203-214, together with an English language translation.
Yao, Takeshi, "Establishment of NBI Combined Magnifying Endoscope Findings of Normal Gastric Mucosal Membrane", Stomach Magnifying Endoscope, 2009, pp. 79-87, together with an English language translation.
English Abstract of JP 2004-181096, dated Jul. 2, 2004.
English Abstract of JP 2007-209770, dated Aug. 23, 2007.

* cited by examiner

MEDICAL IMAGE PROCESSING DEVICE

CROSS REFERENCE TO RELATED APPLICATION

This application is a continuation application of PCT/JP2013/079884 filed on Nov. 5, 2013 and claims benefit of Japanese Applications No. 2012-245667 filed in Japan on Nov. 7, 2012, No. 2012-266445 filed in Japan on Dec. 5, 2012, the entire contents of each of which are incorporated herein by their reference.

BACKGROUND OF THE INVENTION

1. Field of the Invention

The present invention relates to a medical image processing device that applies image processing to a medical image obtained by picking up an image of a biological mucous membrane.

2. Description of the Related Art

Observation using an image pickup apparatus such as an endoscope (including a capsule type) apparatus has been widely performed in a medical field. The endoscope apparatus includes, for example, an elongated insertion portion inserted into a body cavity as a living organism and has a configuration and action for picking up, with image pickup means such as a solid-state image pickup device, an image in the body cavity formed by an objective optical system arranged at a distal end portion of the insertion portion, outputting the image as an image pickup signal, and displaying a video of the image in the body cavity on display means such as a monitor on the basis of the image pickup signal.

A user performs observation of, for example, organs in the body cavity on the basis of the video of the image in the body cavity displayed on the display means such as the monitor. The endoscope apparatus is capable of directly picking up an image of a digestive tract mucous membrane. Therefore, the user can comprehensively observe various findings such as a tone of a mucous membrane, a shape of a lesion, and a microscopic structure on a mucous membrane surface (a mucous membrane microstructure), for example.

A large number of diagnostics for classifying and diagnosing conditions of diseases using the findings of the mucous membrane microstructure (a blood vessel, a pit, an epithelium structure, etc.) are proposed targeting various organs such as a large intestine, a stomach, and an esophagus. For example, as one of diagnostics widely used in Japan, there is a pit pattern classification of a large intestine. Further, in recent years, according to spread of an endoscope for narrow band light observation (NBI), examinations of diagnostics for a medical image picked up by the NBI are actively performed.

However, sufficient experience and the like are necessary for understanding and practice of these diagnostics. Therefore, it is difficult to make best use of the diagnostics when determinations are different depending on doctors and is difficult for an inexperienced doctor to make best use of the diagnostics. Therefore, researches and developments are performed concerning computer aided diagnosis (CAD) for providing, through image processing for a medical image, support information such as an estimation result of a condition of a disease by identification and image analysis of a microstructure that should be paid attention to in provision of a quantitative determination scale and diagnosis.

In a mucous membrane microstructure in an endoscopic image, an image of a continuous pattern is picked up in a complicated form. Highly accurate extraction and analysis are difficult with a conventional image analysis method. An image of a pattern of the mucous membrane microstructure to be picked up is different according to a difference in an organ such as a stomach or a large intestine. Further, in the same organ, for example, in the stomach, an image of a pattern is different in a pyloric gland and a fundic gland.

Furthermore, images of mucous membrane microstructures of a blood vessel, an epithelium structure, and the like are two-dimensionally picked up on an endoscopic image. However, as described in Takeshi Yao: Stomach Magnifying Endoscope; PP. 79-87, 2009 (hereinafter referred to as Non-Patent Literature), the mucous membrane microstructures actually assume three-dimensional structures.

Japanese Patent No. 2918162 describes a method of dividing and detecting a small region with a gastric area in a stomach mucous membrane set as a unit region. However, a minimum unit of a target region is the gastric area. The method does not target an analysis of a structure so complicated and small as a range set as one unit in terms of biological histology. Japanese Patent No. 4451460 discloses content for setting a plurality of regions of interest (abbreviated as ROIs) in an endoscopic image, calculating feature values from the respective ROIs, and estimating and discriminating a pit pattern classification. Note that the setting of the ROIs is manually performed.

SUMMARY OF THE INVENTION

A medical image processing device according to an aspect of the present invention includes: an input section to which a biological mucous membrane image obtained by picking up an image of a biological mucous membrane is inputted; a region extracting section that extracts a mucous membrane microstructure region corresponding to a mucous membrane microstructure, which is a microscopic structure included in the biological mucous membrane, from the biological mucous membrane image inputted to the input section; a closed region identifying section that identifies at least one closed region regarded as being surrounded by the mucous membrane microstructure region; and a unit region setting section that sets a unit region, which is a region set as one unit in terms of biological histology, on the basis of the mucous membrane microstructure region extracted by the region extracting section and the closed region identified by the closed region identifying section.

DETAILED DESCRIPTION OF THE PREFERRED EMBODIMENTS

Embodiments of the present invention are explained below with reference to the drawings.

First Embodiment

In a first embodiment of the present invention, a processing apparatus and a processing method for setting a region divided as a unit region from an image of a mucous membrane microstructure picked up as an endoscopic image, which is a medical image, are explained. FIG. 1 to FIG. 13 relate to the first embodiment of the present invention.

Figure 1:
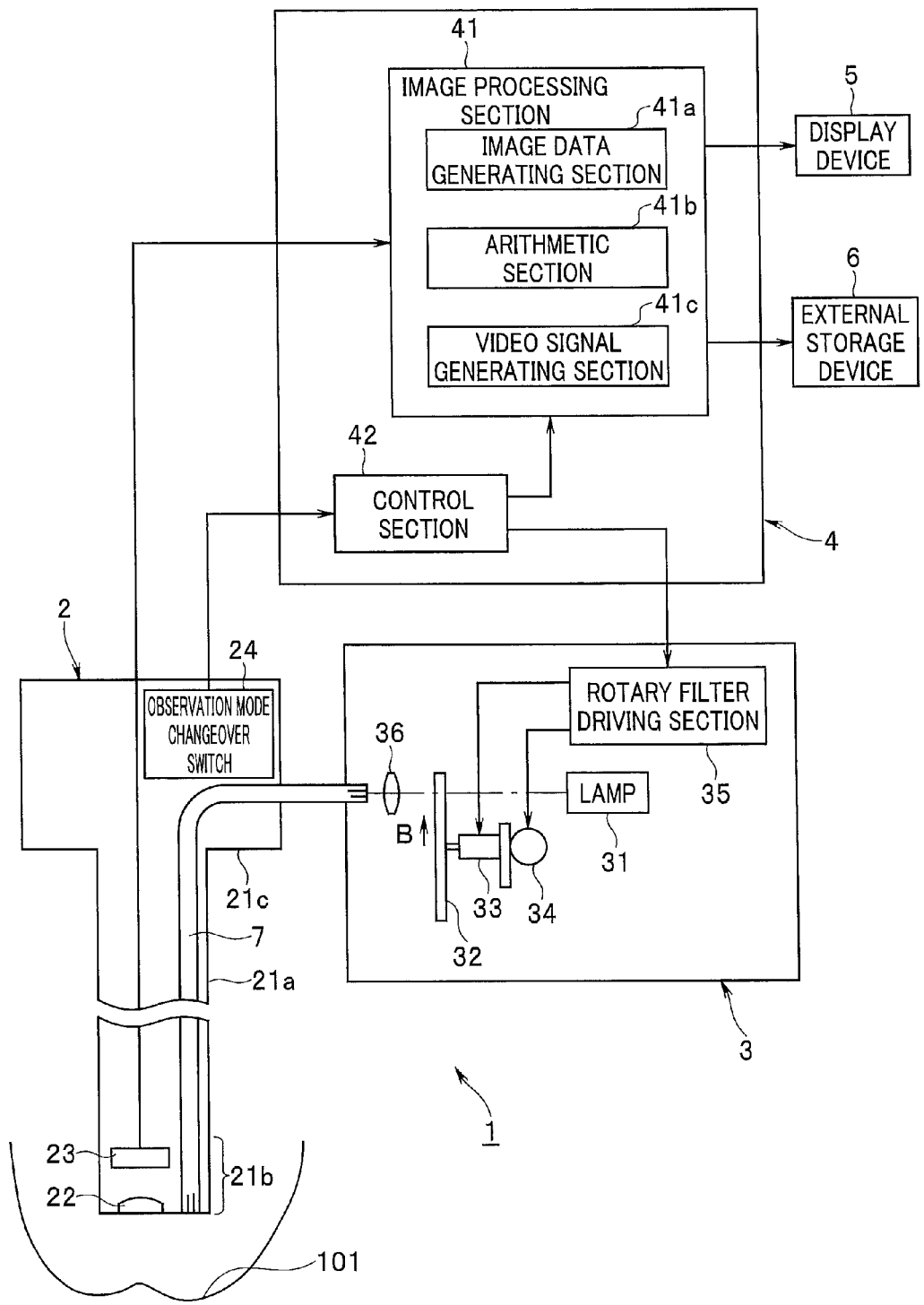
FIG. 1 is a diagram showing an example of a schematic configuration of an endoscope apparatus including a medical image processing device according to a first embodiment of the present invention.

As shown in FIG. 1, an endoscope apparatus 1 includes an endoscope 2 that is inserted into a body cavity of a subject and outputs, as a signal, an image obtained by picking up an image of an object such as a biological tissue 101 in the body cavity, a light source device 3 that emits illumination light for illuminating the biological tissue 101, a processor 4 configuring a medical image processing device that applies various kinds of processing to the output signal from the endoscope 2, a display device 5 that displays an image corresponding to a video signal from the processor 4, and an external storage device 6 that stores an output signal corresponding to a processing result in the processor 4.

The endoscope 2 includes an insertion portion 21a including an elongated shape and a dimension insertable into the body cavity of the subject, a distal end portion 21b provided on a distal end side of the insertion portion 21a, and an operation portion 21c provided on a proximal end side of the insertion portion 21a. A light guide 7 for transmitting the illumination light emitted in the light source device 3 to the distal end portion 21b is inserted through an inside of the insertion portion 21a.

One end face (a light incident end face) of the light guide 7 is detachably connected to the light source device 3. The other end face (a light emission end face) of the light guide 7 is arranged near a not-shown illumination optical system provided at the distal end portion 21b of the endoscope 2. With such a configuration, the illumination light emitted in the light source device 3 is emitted to the biological tissue 101 in the body cavity after being transmitted through the light guide 7 connected to the light source 3 and the not-shown illumination optical system provided at the distal end portion 21b.

At the distal end portion 21b of the endoscope 2, an objective optical system 22 that forms an optical image of the object and a charge coupled device (abbreviated as CCD) 23 arranged in an image forming position of the objective optical system 22 and configuring an image pickup section that picks up an optical image and acquires the optical image as an image are provided. In the operation portion 21c of the endoscope 2, an observation mode changeover switch 24 capable of performing an instruction for switching an observation mode to any one of a normal light observation mode and a narrowband light observation mode is provided.

The light source device 3 includes a white light source 31 formed by a Xenon lamp or the like, a rotary filter 32 that changes white light emitted from the white light source 31 to frame-sequential illumination light, a motor 33 that drives to rotate the rotary filter 32, a motor 34 that moves the rotary filter 32 and the motor 33 in a direction (a sign A in FIG. 1) perpendicular to an emission optical path of the white light source 31, a rotary filter driving section 35 that drives the motors 33 and 34 on the basis of control by a control section 42 of the processor 4, and a condensing optical system 36 that condenses the illumination light transmitted through the rotary filter 32 and supplies the illumination light to the incident end face of the light guide 7.

Figure 2:
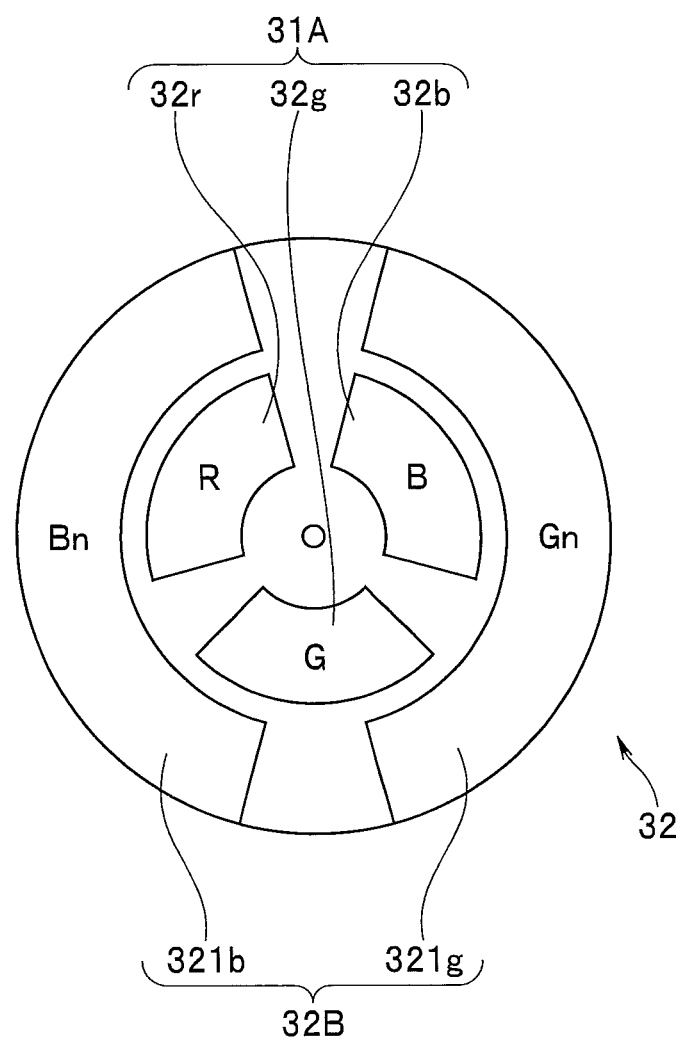
FIG. 2 is a diagram showing an example of a configuration of a rotary filter included in a light source device shown in FIG. 1.

As shown in FIG. 2, the rotary filter 32 is formed in a disk shape, a center of which is a rotating shaft. The rotary filter 32 includes a first filter group 32A including a plurality of filters provided along a circumferential direction on an inner circumference side and a second filter group 32B including a plurality of filters provided along a circumferential direction on an outer circumference side. A driving force of the motor 33 is transmitted to the rotating shaft, whereby the rotary filter 32 rotates. Note that, in the rotary filter 32, portions other than portions where the respective filters of the first filter group 32A and the second filter group 32B are arranged are configured by a light blocking member.

The first filter group 32A includes an R filter 32r that allows light in a red wavelength band to pass, a G filter 32g that allows light in a green wavelength band to pass, and a B filter 32b that allows light in a blue wavelength band to pass, which are respectively provided along the circumferential direction on the inner circumference side of the rotary filter 32.

Figure 3:
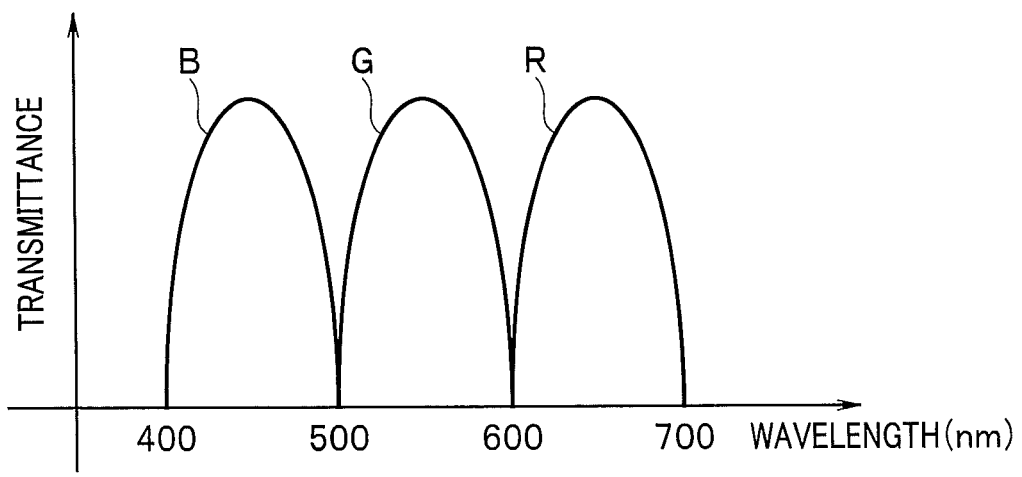
FIG. 3 is a diagram showing an example of transmission characteristics of respective filters included in a first filter group shown in FIG. 2.

For example, as shown in FIG. 3, the R filter 32r has a configuration for mainly transmitting light (R light) from 600 nm to 700 nm. For example, as shown in FIG. 3, the G filter 32g has a configuration for mainly transmitting light (G light) from 500 nm to 600 nm. Further, as shown in FIG. 3, the B filter 32b has a configuration for mainly transmitting light (B light) from 400 nm to 500 nm. Note that, in FIG. 3, the R filter 32r, the G filter 32g, and the B filter 32b are simply indicated by R, G, and B.

The white light emitted in the white light source 31 is transmitted through the first filter group 32A, whereby wide band light for the normal light observation mode is generated.

The second filter group 32B includes a Bn filter 321b that allows blue and narrowband light to pass and a Gn filter 321g that allows green and narrowband light to pass, which are respectively provided along the circumferential direction on the outer circumference side of the rotary filter 32.

Figure 4:
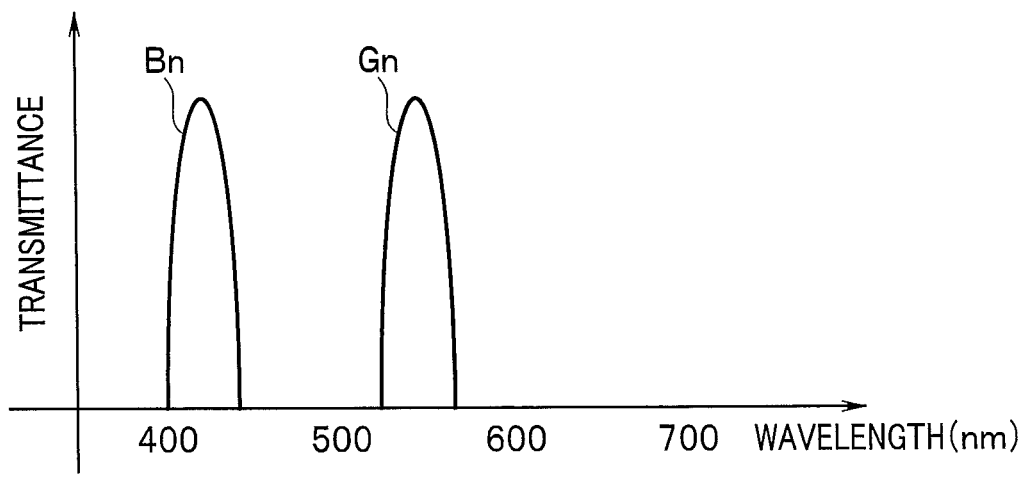
FIG. 4 is a diagram showing an example of transmission characteristics of respective filters included in a second filter group shown in FIG. 2.

For example, as shown in FIG. 4, a center wavelength of the Bn filter 321b is set near 415 nm. The Bn filter 321b is configured to transmit light (Bn light) in a narrow band compared with the B light.

For example, as shown in FIG. 4, a center wavelength of the Gn filter 321g is set near 540 nm. The Gn filter 321g is configured to transmit light (Gn light) in a narrow band compared with the G light. Note that, in FIG. 4, the Bn filter 321b and the Gn filter 321g are simply indicated by Bn and Gn.

The white light emitted in the white light source 31 is transmitted through the second filter group 32B, whereby narrowband lights in a plurality of discrete bands for the narrowband light observation mode are generated.

The processor 4 includes a configuration including a function of the medical image processing device in the present embodiment. More specifically, as shown in FIG. 1, the processor 4 includes an image processing section 41 and a control section 42. The image processing section 41 includes an image data generating section 41a, an arithmetic section 41b, and a video signal generating section 41c.

The image data generating section 41a of the image processing section 41 applies processing such as noise removal and A/D conversion to an output signal from the endoscope 2 on the basis of control by the control section 42 to thereby generate image data corresponding to an image obtained in the CCD 23.

The arithmetic section 41b of the image processing section 41 performs predetermined processing using the image data generated by the image data generating section 41a to thereby extract a mucous membrane microstructure of a living organism out of image data obtained by picking up an image of the biological tissue 101. Further, the arithmetic section 41b performs an arithmetic operation for setting a unit region based on predetermined conditions from the mucous membrane microstructure.

Note that, in the present embodiment, it is assumed that the mucous membrane microstructure of the living organism is included in the image data. Unit region setting processing serving as processing for setting, concerning the mucous membrane microstructure, as a unit region, a range set as one unit in terms of biological histology is performed. Details of such unit region setting processing are explained below.

The video signal generating section 41c of the image processing section 41 applies processing such as gamma conversion and D/A conversion to the image data generated by the image data generating section 41a to thereby generate a video signal and outputs the video signal to the display device 5 and the like.

When the control section 42 detects that an instruction for switching to the normal light observation mode is performed on the basis of an instruction of the observation mode changeover switch 24, the control section 42 applies, to the rotary filter driving section 35, control for causing the light source device 3 to emit wideband light for the normal light observation mode. The rotary filter driving section 35 causes, on the basis of the control by the control section 42, the motor 34 to operate to insert the first filter group 32A on an emission optical path of the white light source 31 and retract the second filter group 32B from the emission optical path of the white light source 31.

When the control section 42 detects that an instruction for switching to the narrowband light observation mode is performed on the basis of an instruction of the observation mode changeover switch 24, the control section 42 applies, to the rotary filter driving section 35, control for causing the light source device 3 to emit narrowband lights in a plurality of bands for the narrowband light observation mode.

The rotary filter driving section 35 causes, on the basis of the control by the control section 42, the motor 34 to operate to insert the second filter group 32B on the emission optical path of the white light source 31 and retract the first filter group 32A from the emission optical path of the white light source 31.

That is, with the configuration of the endoscope apparatus 1 explained above, when the normal light observation mode is selected, it is possible to cause the display device 5 to display an image (a normal light image) having a tint substantially the same as a tint obtained when an observation target such as the biological tissue 101 is viewed by naked eyes and further cause the external storage device 6 to store the image. With the configuration of the endoscope apparatus 1 explained above, when the narrowband light observation mode is selected, it is possible to cause the display device 5 to display an image (a narrowband light image) in which a blood vessel near a surface layer included in the biological tissue 101 is highlighted and further cause the external storage device 6 to store the image.

Figure 5:
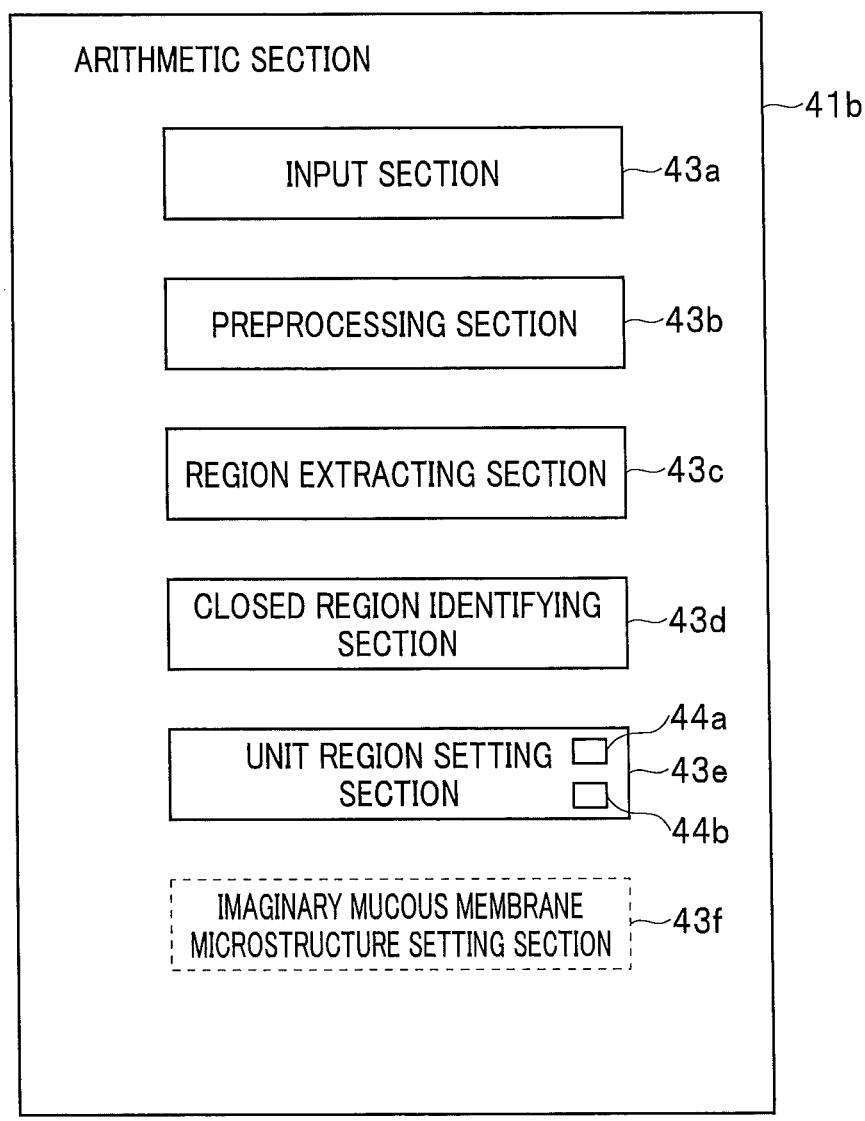
FIG. 5 is a block diagram showing a configuration of an arithmetic section shown in FIG. 1.

As shown in FIG. 5, the arithmetic section 41b configuring the medical image processing device shown in FIG. 1 includes an image input section (abbreviated simply as input section) 43a to which (image data of) a biological mucous membrane image obtained by picking up an image of a biological mucous membrane with the CCD 23 is inputted from the image data generating section 41a, a preprocessing section 43b that applies preprocessing to the biological mucous membrane image inputted to the input section 43a, a region extracting section 43c that extracts a mucous membrane microstructure region corresponding to a mucous membrane microstructure subjected to the preprocessing, a closed region identifying section (or a substantially closed region identifying section) 43d that identifies at least one closed region (or surrounded region) regarded as being surrounded by the mucous membrane microstructure region, and a unit region setting section 43e that sets a unit region on the basis of the mucous membrane microstructure region extracted by the region extracting section 43c and the closed region identified by the closed region identifying section 43d. The medical image processing device is not limited to a configuration in which the arithmetic section 41b includes the input section 43a and may have a configuration in which the image processing section 41 (e.g., the image data generating section 41a) excluding the arithmetic section 41b includes the input section 43a.

As explained above, the processor 4 functioning as the medical image processing device in the present embodiment is characterized by including the arithmetic section 41b including the input section 43a, the region extracting section 43c, the closed region identifying section 43d, and the unit region setting section 43e. The region extracting section 43c may be configured to extract, without performing the preprocessing, the mucous membrane microstructure region corresponding to the mucous membrane microstructure from the biological mucous membrane image inputted to the input section 43a.

The unit region setting section 43e shown in FIG. 5 includes a width calculating section 44a functioning as a feature value calculating section that calculates, from the mucous membrane microstructure region or the closed region, a width of a belt-shaped mucous membrane microstructure region as a feature value used for range setting for a unit region and a range setting section 44b that sets a range of the unit region on the basis of the feature value of the width.

Note that the input section 43a configuring the arithmetic section 41b may be configured at an input end of image data to the arithmetic section 41b. The configuration is shown in which the region extracting section 43c, the closed region identifying section 43d, the unit region setting section 43e, the width calculating section 44a, and the range setting section 44b are provided in the arithmetic section 41b configured by a central processing unit (CPU) or the like. However, the present embodiment is not limited to such a case. The region extracting section 43c, the closed region identifying section 43d, the unit region setting section 43e, the width calculating section 44a, and the range setting section 44b may be configured using kinds of dedicated hardware that perform the processing of the respective sections. For example, the region extracting section 43c, the closed region identifying section 43d, the unit region setting section 43e, the width calculating section 44a, and the range setting section 44b may be respectively configured by a region extracting circuit, a closed region identifying circuit, a unit region setting circuit, a width calculating circuit, and a range setting circuit. The same applies to a convolutional operation section 45a, a substantially closed region pixel candidate detecting/labeling section 45b, and the like in an embodiment explained below.

Next, action of the endoscope apparatus 1 including the processor 4 functioning as the medical image processing device is explained.

First, after turning on power supplies of the respective sections of the endoscope apparatus 1, a surgeon selects the normal light observation mode in the observation mode changeover switch 24. The surgeon inserts, while viewing an image displayed on the display device 5 when the normal light observation mode is selected, that is, an image having a tint substantially the same as a tint obtained when an object is viewed with naked eyes, the endoscope 2 into a body cavity to thereby bring the distal end portion 21b to a part where the biological tissue 101 set as an observation target is present.

When the normal light observation mode is selected by the observation mode changeover switch 24, lights of respective colors, i.e., R light, G light, and B light are sequentially emitted from the light source device 3 to the biological tissue 101. Images corresponding to the lights of the respective colors are respectively acquired in the endoscope 2.

When the image corresponding to the R light, the image corresponding to the G light, and the image corresponding to the B light are inputted, the image data generating section 41a of the image processing section 41 generates image data of color components corresponding to the respective images, respectively.

Figure 6A:
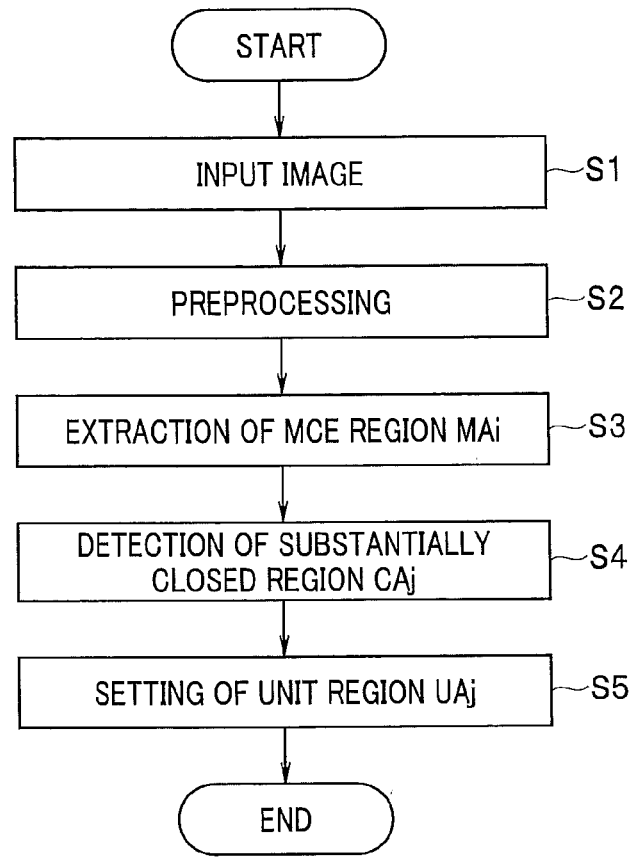
FIG. 6A is a flowchart showing processing content in the first embodiment.

Next, details of an operation for performing the unit region setting processing for setting a unit region included in the arithmetic section 41b of the image processing section 41 are explained. FIG. 6A shows main processing for performing the unit region setting processing.

In an example of image data obtained by picking up an image of a pyloric gland of a stomach forming an epithelium pattern (an epithelium structure) on the biological tissue 101 in the narrowband light observation mode, the unit region setting processing is explained concerning a case in which a mucous membrane microstructure included in the image data is a marginal crypt epithelium (MCE).

Figure 7:
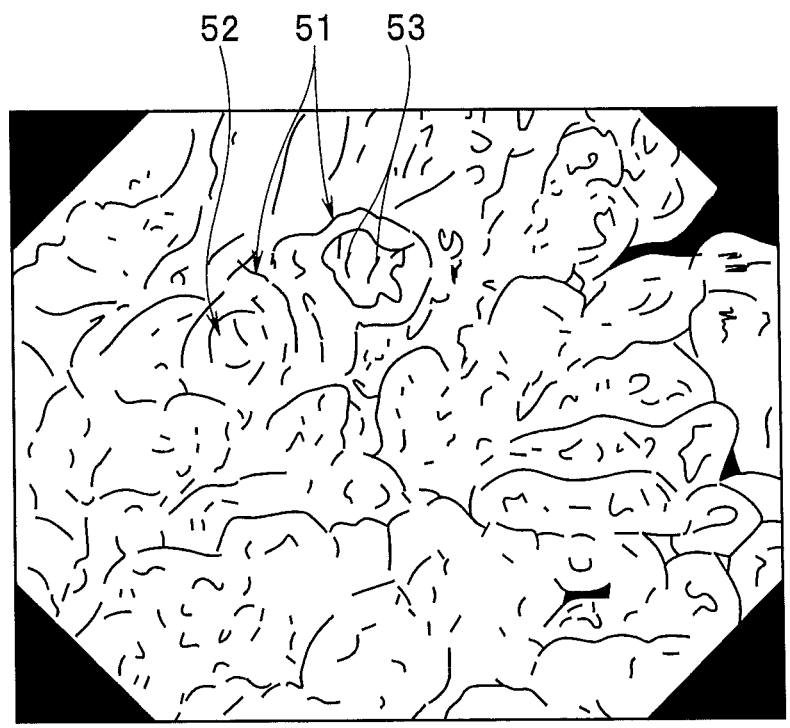
FIG. 7 is a schematic diagram of an endoscopic image.
Figure 8:
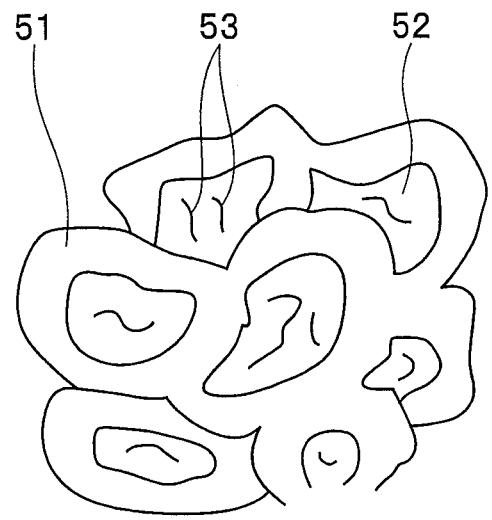
FIG. 8 is an enlarged schematic diagram of a part of FIG. 7.

FIG. 7 schematically shows an image obtained by picking up an image of the pyloric gland of the stomach in the narrowband light observation mode. There is a merit that a structure and the like near a surface layer are displayed more clearly by picking up an image in the narrowband light observation mode than a case of the wideband light observation mode. An image obtained by locally slicing out a part of the image shown in FIG. 7 is shown in FIG. 8. In FIG. 7 and FIG. 8, a plurality of belt-shaped MCEs 51 are present overlapping one another. An interval portion 52 is present in a region (usually a closed region) on an inner side surrounded by the MCE 51. Blood vessels 53 run in the interval portion 52.

Further, image data picked up by the endoscope 2 depends on image pickup conditions such as a distance and an angle and a state of a mucous membrane itself. Therefore, a boundary of one MCE 51 is clear in some case and a boundary of the MCE 51 adjacent to the MCE 51 is unclear in other cases.

As shown in step S1 in FIG. 6A, image data generated by the image data generating section 41a is inputted to the preprocessing section 43b in the arithmetic section 41b from the input section 43a. Note that image data in the present embodiment and the other embodiments is formed by three (color component) images of RGB, a size (lateral and longitudinal numbers of pixels) of which is ISX×ISY. Each of the respective images of R, G, and B include 8-bit gradations formed by values 0 to 255. For example, ISX×ISY=640×480.

In the next step S2, the preprocessing section 43b applies preprocessing such as noise suppression and inverse gamma correction to the inputted image data. In the present embodiment, as the noise suppression, publicly-known median filtering (for rearranging pixel values in a mask including a pixel of attention according to magnitudes and replacing a value of the pixel of attention with a median) is applied in a mask size of a size 3×3.

Note that gamma correction is nonlinear processing applied to give visually linear gradation when an image is displayed on a monitor or the like. The inverse gamma correction resets the nonlinear gradation to the original linear gradation. Therefore, when the gamma correction is not applied to image data inputted to the preprocessing section 43b, the inverse gamma correction is unnecessary.

The image data subjected to the preprocessing is outputted to the region extracting section 43c. As shown in step S3, the region extracting section 43c performs extraction of a belt-shaped MCE region MAi (i≥1) as a mucous membrane microstructure region corresponding to a mucous membrane microstructure.

Figure 6B:
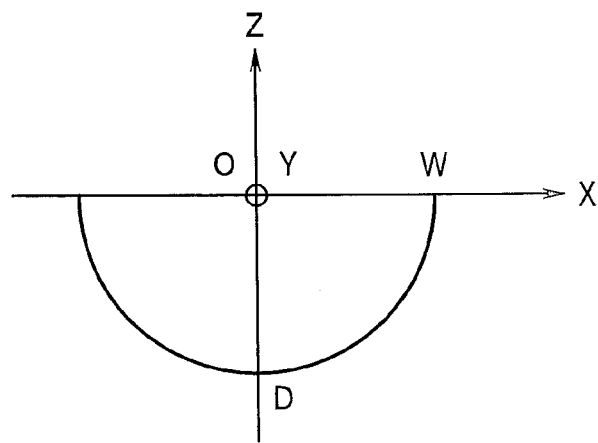
FIG. 6B is a diagram showing a semielliptical shape used in a template matching.

As an extraction method for the MCE region MAi, for example, a structural component extraction method by template matching described in Japanese Patent No. 4409166 is used. FIG. 6B shows a semielliptical shape used in the template matching.

Note that a width W of a semielliptical shape used for creation of a template is set as W=3 to 9 (at an interval of 1.0). A depth D of the semielliptical shape may be set to a value corresponding to the depth of the MCE region MAi. As the other parameters, values described in the embodiment of the Japanese Patent No. 4409166 only have to be used as they are.

Figure 9:
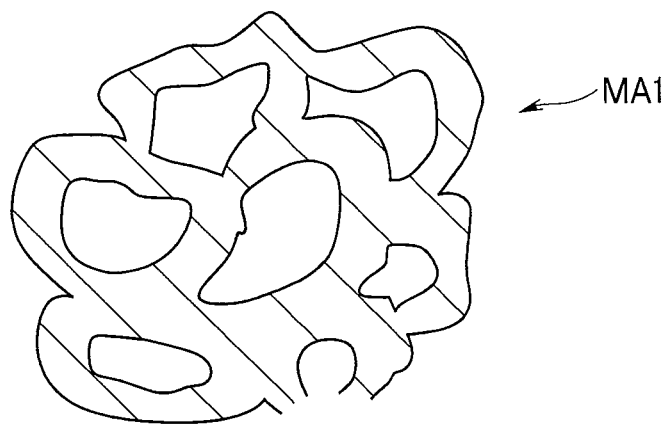
FIG. 9 is a diagram showing an example of a detection result of an MCE region MA1 in the first embodiment.

As in the embodiment of Japanese Patent No. 4409166, processing only has to be carried out targeting a G image among three images of RGB. Such an extraction method is applied to the image data shown in FIG. 7 or FIG. 8 to extract an MCE region MA1, for example, as shown in FIG. 9. The extracted MCE region MA1 is outputted to the closed region identifying section 43d. Note that the extracted MCE region MA1 is indicated by hatching in FIG. 9.

In the next step S4 in FIG. 6A, the closed region identifying section 43d performs processing for detecting or identifying a substantially closed region CAj (j≥1) substantially surrounded by the MCE region MAi detected as the mucous membrane microstructure region (in other words, as a closed region surrounded by or a substantially closed region regarded as being surrounded by the MCE region MAi).

Note that, in the first embodiment and a modification of the first embodiment, the substantially closed region CAj is a surrounded closed region. In a second embodiment explained below, the substantially closed region CAj includes a surrounded closed region and a substantially closed region not completely surrounded but substantially surrounded.

Figure 10:
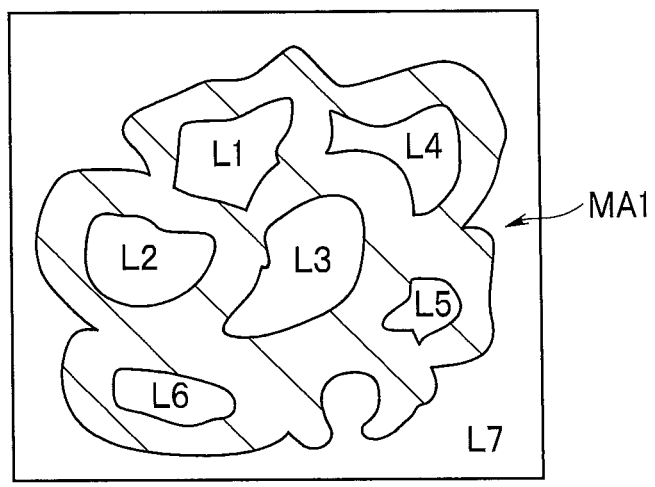
FIG. 10 is a diagram showing an example of a labeling result of a region including the MCE region MA1 in the first embodiment.

In order to perform the processing in step S4, publicly-known labeling is carried out for regions of pixels other than the region detected as the MCE region MAi. When the labeling is applied to a detection result of the MCE region MA1 shown in FIG. 9, the MCE region MA1 is divided into seven labels L1 to L7 as shown in FIG. 10. Note that, in FIG. 10, processing for surrounding an opening region and closing an unclosed end portion is applied in the MCE region MA1 shown in FIG. 9. The MCE region MA1 is indicated by hatching in FIG. 10.

Among the labels L1 to L7, the labels other than the label including outermost peripheral pixels (pixels, X coordinates of which are 0 or 639, and pixels, Y coordinates of which are 0 or 479) of image data in pixels in the label are set as the substantially closed region CAj. In an example of application to FIG. 10, the labels L1 to L6 excluding the label L7 are respectively substantially closed regions CA1 to CA6. Information concerning the substantially closed regions CA1 to CA6 detected or identified by the closed region identifying section 43d is outputted to the unit region setting section 43e.

In the next step S5, the range setting section 44b of the unit region setting section 43e calculates a width serving as a feature value of the MCE region MAi on the basis of the substantially closed region CAj and performs processing for setting a range of a unit region UAj.

First, the width calculating section 44*a* of the unit region setting section 43*e* calculates a width Wk (k≥1) serving as a feature value of the MCE region MAi adjacent to the substantially closed region CAj. For example, the width calculating section 44*a* scans pixels in a direction opposite to the substantially closed region CAj adjacent to the MCE region MAi from a boundary pixel BPk (e.g., on the substantially closed region CAj side) with the MCE region MAi adjacent to the substantially closed region CAj and counts the number of pixels of the MCE region MAi to calculate the width Wk in the boundary pixel BPk.

Figure 11:
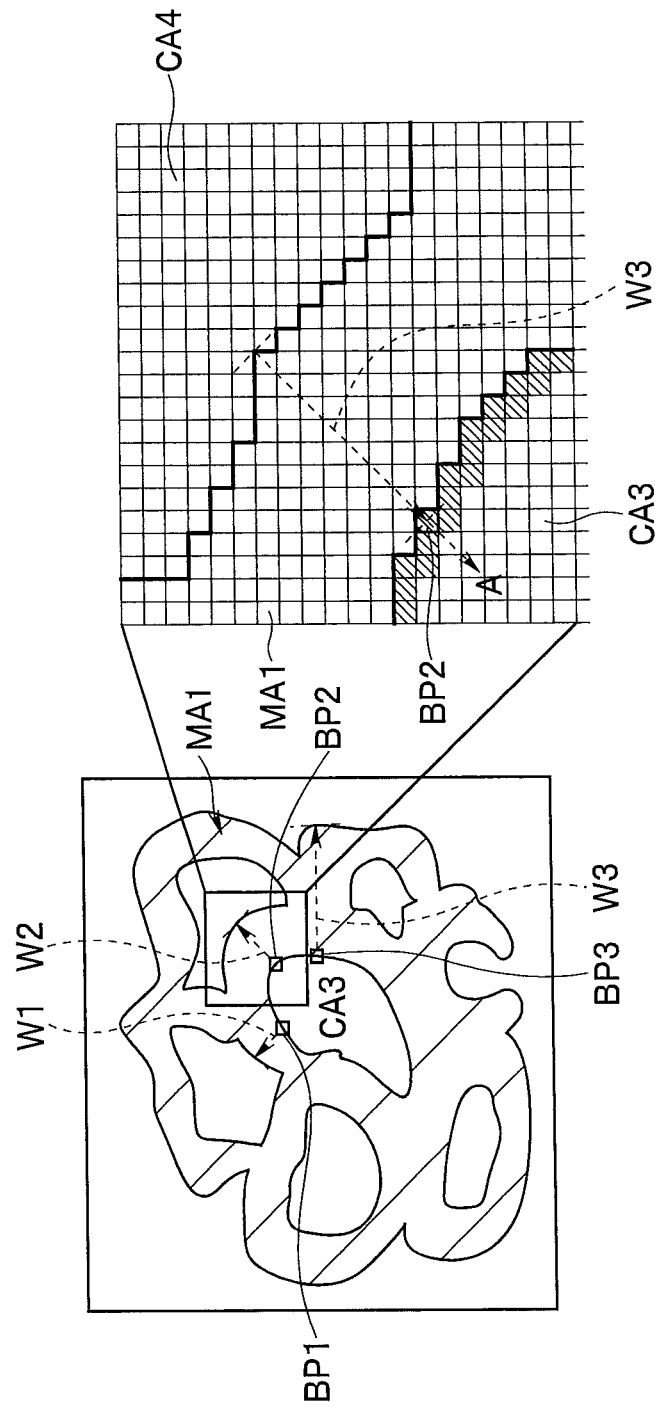
FIG. 11 is a diagram showing an example of a case in which a width Wk is calculated as a feature value of an MCE region MAi in the first embodiment.

FIG. 11 shows an example in which widths W1, W2, and W3 in, for example, three representative directions in a case in which the substantially closed region CA3 is set as a target are calculated and an enlarged view of a case in which the width W2 is calculated in one direction with attention paid to the boundary pixel BP2. Note that, the MCE region MA1 is indicated by hatching in FIG. 11.

In FIG. 11, a state is shown in which, when three boundary pixels BP1, BP2, and BP3 are set in an outer periphery of the substantially closed region CA3, the widths W1, W2, and W3 of the MCE region MA1 adjacent to the substantially closed region CA3 are calculated respectively from the respective boundary pixels BP1, BP2, and BP3. In the following explanation, concerning the case of one boundary pixel BP2, the width W2 is calculated with reference to an enlarged view of a part including the boundary pixel BP2.

As shown in an enlarged view of FIG. 11, the substantially closed region CA3 adjacent to the boundary pixel BP2 is located in a left downward direction (a direction indicated by A in FIG. 11). Therefore, pixels are scanned in a right upward direction, which is a direction opposite to the left downward direction, from the boundary pixel BP2. When the number of pixels of the MCE region MA1 is counted while the pixels are scanned in the right upward direction (in FIG. 11, the substantially closed region CA4 side), the number of pixels is 8. This is a value of the width W2.

Note that, when the substantially closed regions CAj adjacent to the boundary pixel BPk are present in a plurality of pixels, the pixels are scanned in directions of the respective substantially closed regions CAj to count the number of pixels. A smallest number of pixels is set as a value of the width Wk. In FIG. 11, only the three pixels of the boundary pixels BP1, BP2, and BP3 discretely shown in the substantially closed region CA3 are illustrated. However, the calculation of the width Wk is carried out in all the boundary pixels BPk.

Next, an average of the widths Wk calculated in all the boundary pixels BPk is set as a region size ASj of the MCE region MAj adjacent to the substantially closed region CAj. The range setting section 44*b* sets or determines, on the basis of the calculation of the width by the width calculating section 44*a*, as a range of the unit region UAj, a region obtained by combining the substantially closed region CAj and the MCE region MAi located in a range of the region size ASj from the substantially closed region CAj.

Figure 12:
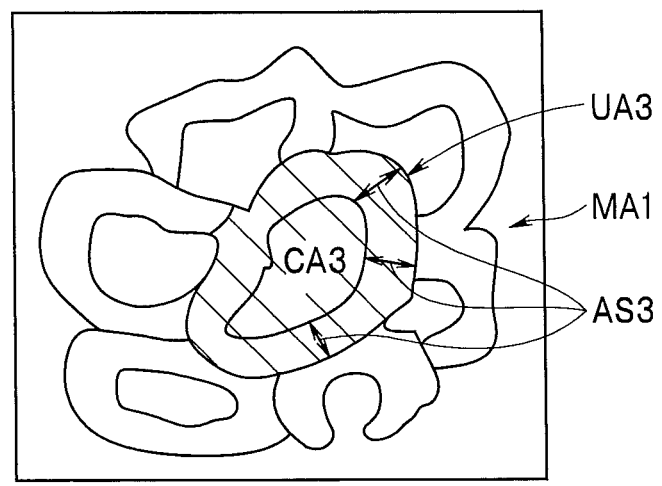
FIG. 12 is a diagram showing an example of setting of a unit region UA3 in the first embodiment.

FIG. 12 shows an example of a unit region UA3 set when the substantially closed region CA3 explained with reference to FIG. 11 is set as a target and a region size AS3 of the MCE region MA1 adjacent to the substantially closed region CA3. Note that the set unit region UA3 is indicated by hatching in FIG. 12. The unit region UA3 shown in FIG. 12 is a region obtained by combining the substantially closed region CA3 and the belt-shaped MCE region MA1 located in a range of the region size AS3, which is determined by the average of the width, from an outer peripheral boundary (a peripheral edge boundary) of the substantially closed region CA3 to surround the substantially closed region CA3. The belt-shaped MCE region MA1 located in the range of the region size AS3 surrounding the substantially closed region CA3 (e.g., determined by the average of the width) may be represented as MCE region MA1-3. When this representation is used, the unit region UA3 shown in FIG. 12 is formed by the substantially closed region CA3 and the belt-shaped MCE region MA1-3 surrounding the substantially closed region CA3.

In the above explanation, the processing or the method for calculating, from the substantially closed region CAj, the width Wk serving as the feature value of the belt-shaped MCE region MAi surrounding the substantially closed region CAj and setting the range of the unit region UAj is illustrated targeting the substantially closed region CA3. However, actually, the processing or the method is carried out for all the substantially closed regions CAj.

Figure 13:
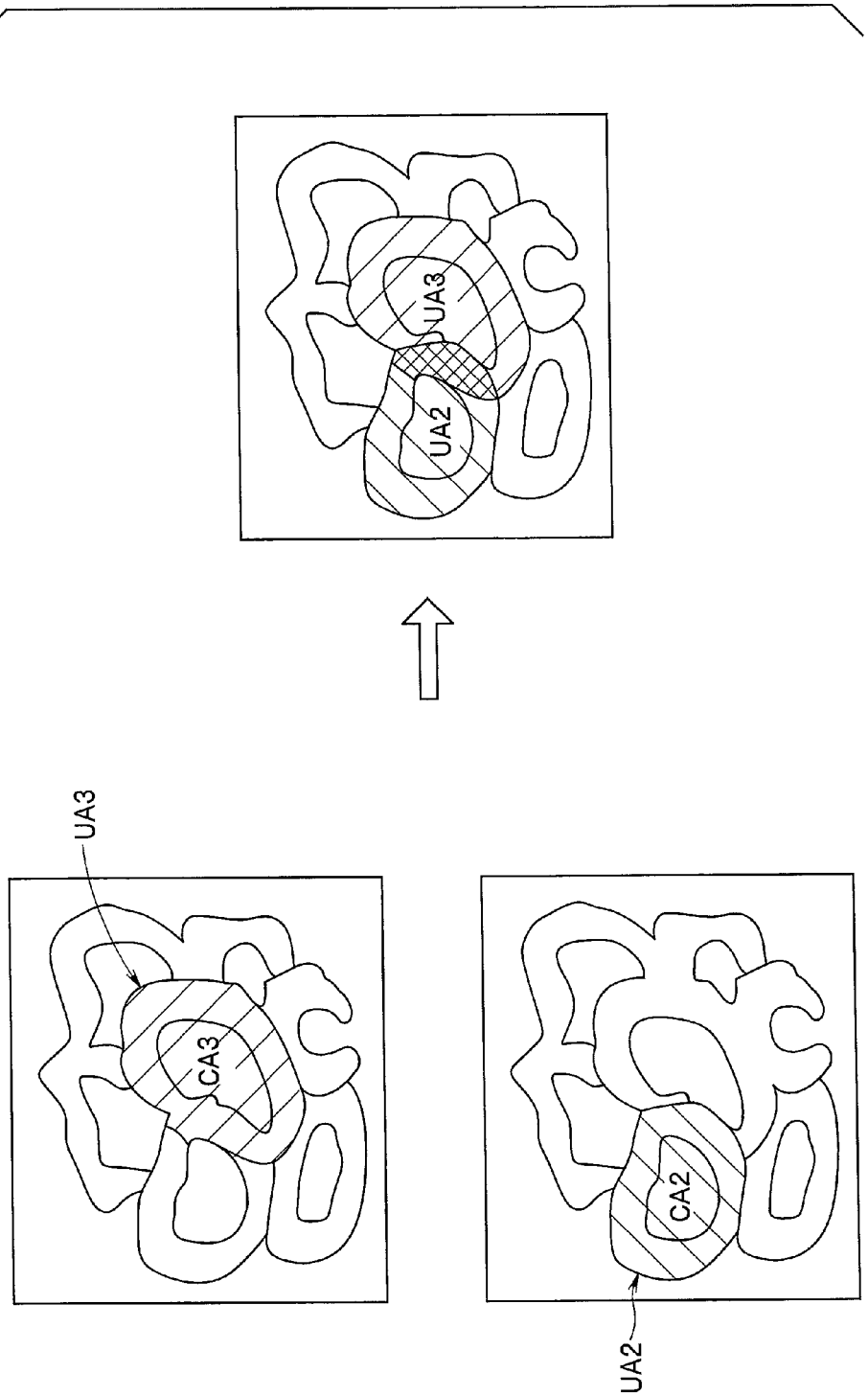
FIG. 13 is a diagram showing an example in which unit regions UA2 and UA3 overlap in the first embodiment.

When the processing or the method is carried out, as shown in FIG. 13, a range of certain unit region UA3 is allowed to overlap a range of another unit region UA2.

According to FIG. 13, the unit region UA3 set from the substantially closed region CA3 explained with reference to FIG. 12 is indicated by hatching. According to FIG. 13, the unit region UA2 set from the substantially closed region CA2 according to processing same as the processing in the case of the substantially closed region CA3 is indicated by hatching.

According to FIG. 13, the unit region UA2 and the unit region UA3 overlap in a region indicated by cross-hatching. However, when unit regions are set, a part of a certain unit region is allowed to overlap a part of another unit region in this way. In other words, when the unit region setting section 43*e* performs the setting of unit regions for a plurality of closed regions, the unit region setting section 43*e* performs the setting of unit regions independently for each of the plurality of closed regions. As a result, as shown in FIG. 13, parts of the unit regions (more specifically, belt-shaped MCE regions) are allowed to overlap each other.

Consequently, a region set as one unit in terms of the biological histology can be set as the unit region UAj from the image data. In other words, one closed region like the interval portion 52 including the blood vessels 53 or the substantially closed region CAj regarded as a closed region and one MCE region MAi formed in a belt-shaped closed loop shape surrounding the substantially closed region CAj can be set as the unit region UAj from the image data.

In the above explanation, when the width Wk of the MCE region MAi is calculated, the boundary pixel BPk of the substantially closed region CAj is used. However, the width Wk may be calculated from the MCE region MAi. In other words, the feature value calculating section like the width calculating section 44*a* may calculate a feature value, which is used for the range setting for a unit region, from the MCE region MAi serving as the mucous membrane microstructure region or may calculate the feature value, which is used for the range setting for a unit region, from the substantially closed region CAj serving as the closed region.

Note that content of the preprocessing in step S2 in FIG. 6A is not limited to the noise suppression and the inverse gamma correction. For example, correction of brightness and a tone may be added. Respective methods of the preprocessing do not limit the methods and may be changed according to a target image and characteristics of an apparatus. For example, in the present embodiment, the median filtering is used as the method of the noise suppression. However, other methods such as smoothing filter may be used.

The detecting or extracting method for the MCE region MAi in step S3 is not limited to the structural component extracting method. Other methods may be used. For example, the detecting or extracting method may be threshold processing for a pixel value such as a luminance value or a tone, a method using various frequency filters such as a Gabor filter, or linear detection processing using a Hessian matrix or a vector concentration degree, which is a publicly-known technique.

The detecting or identifying method for the substantially closed region CAj in step S4 is not limited to the method using the labeling. Other methods may be used. For example, a closed region may be searched to detect the substantially closed region CAj by scanning the boundary pixel BPk of the detected MCE region MAi.

In step S5, the width Wk is calculated by counting the number of pixels from the boundary pixel BPk. However, the calculation of the width Wk is not limited to this method. Other methods such as a method of using, as the width Wk, a size of a template or a filter used in the extraction of the MCE region MAi in step S3 may be used.

The calculation of the width Wk is carried out in all the boundary pixels BPk. However, the calculation of the width Wk is not limited to the use of all the boundary pixels BPk. For example, the width Wk may be calculated from pixels sampled at every several pixels.

Further, the calculation of the region size ASj is not limited to the average of the width Wk. Other statistical amounts such as a mode, a minimum, and a maximum of the width Wk may be used.

The calculation of the region size ASj is not limited to a method using the width Wk. The region size ASj may be calculated from a size, a shape, and the like of the substantially closed region CAj or the user may set any value. The region size ASj for specifying a range of a unit region may be determined from, for example, an area of the substantially closed region CAj.

Further, in the present embodiment, the range of the unit region UAj is set as the distance from the boundary pixel of the substantially closed region CAj. However, the setting of the range of the unit region UAj is not limited to this method. The range of the unit region UAj may be set with reference to, for example, a center point (a center of gravity) of the substantially closed region CAj.

In FIG. 13, the example is shown in which the respective unit regions UAj are allowed to overlap. However, it is also possible to determine which of the unit regions UAj overlapping portions belong to and divide overlapping regions.

In the above explanation, the unit region UAj is explained as including the MCE region MAj. However, the unit region UAj may be defined as not including the MCE region MAj. In the case of this definition, the unit region UAj=the substantially closed region CAj.

An image may be displayed on the display device 5 or the like by retaining respective pixels, which are set as the unit region UAj, as image data and generating a video signal with the video signal generating section 41c.

According to the present embodiment, the range set as one unit in terms of the biological histology concerning the mucous membrane microstructure can be set to be separable or extractable as a unit region. Therefore, it is possible to support diagnosis and the like of respective structures on an endoscopic image serving as a medical image. In other words, according to the present embodiment, the range set as one unit in terms of the biological histology concerning the mucous membrane microstructure can be, for example, separated and set or extracted as a unit region.

Therefore, the range set as one unit in terms of the biological histology can be separated or extracted for each of unit regions from a region to be diagnosed even in complicated image data. Therefore, it is easy to perform diagnosis and the like. On the other hand, in the case of the conventional example in which the range set as one unit in terms of the biological histology in the present embodiment cannot be set, diagnosis needs to be performed for a complicated range extending over a plurality of units in terms of the biological histology. It is difficult to perform the diagnosis and the like. Therefore, according to the first embodiment, it is easy to perform diagnosis as explained above. It is possible to effectively support diagnosis and the like by the surgeon or the like. Even when it is attempted to extract a region larger than the unit region, it is easy to extract a region of a desired region size with the unit region set as a unit.

Next, a modification of the first embodiment is explained. In the present modification, an image processing apparatus and an image processing method are explained that can accurately detect the unit region UAj when the MCE region MAi does not assume a complete closed curve because of, for example, destruction of a tissue due to cancer or image pickup conditions. More specifically, an MCE is sometimes unclear because a normal mucous membrane cell is destroyed or replaced by proliferation of a cancer cell. The present modification is explained below mainly with reference to FIG. 14A to FIG. 18.

The present modification corresponds to a modification concerning the processing for detecting the substantially closed region CAj in step S4 in the first embodiment. The present modification can also be applied when the substantially closed region CAj cannot be accurately detected in the first embodiment, for example, when the MCE region MAi detected in step S3 in the first embodiment does not assume a complete closed curve.

A configuration in the present modification is almost the same as the configuration in the first embodiment. More specifically, the arithmetic section 41b configuring the image processing section 41 in the first embodiment further includes, as indicated by a dotted line in FIG. 5, an imaginary mucous membrane microstructure setting section 43f that sets an imaginary mucous membrane microstructure region on a biological mucous membrane image.

In the case of the present modification, the imaginary mucous membrane microstructure setting section 43f sets an imaginary MCE region MAi as the imaginary mucous membrane microstructure region. Therefore, the imaginary mucous membrane microstructure setting section 43f has a function of an imaginary MCE region setting section.

In the present modification, the closed region identifying section 43d identifies, as the closed region (or the substantially closed region) explained in the first embodiment, a region surrounded by the mucous membrane microstructure region extracted by the region extracting section 43c and the imaginary mucous membrane microstructure region (more specifically, the imaginary MCE region MAi) set by the imaginary mucous membrane microstructure setting section 43f.

Figure 14A:
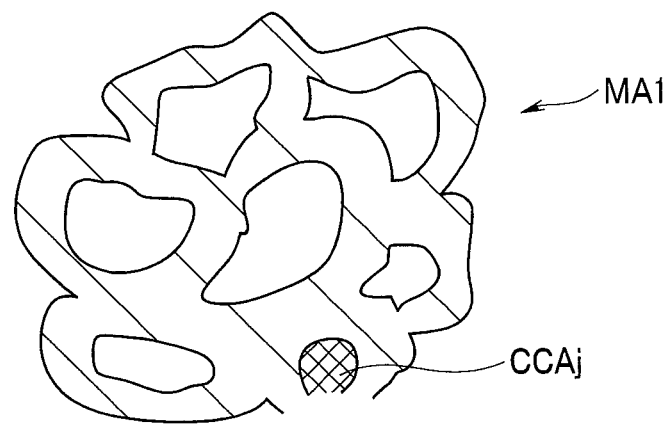
FIG. 14A is a diagram showing an example of a substantially closed region CAj set as a target in a modification of the first embodiment.
Figure 14B:
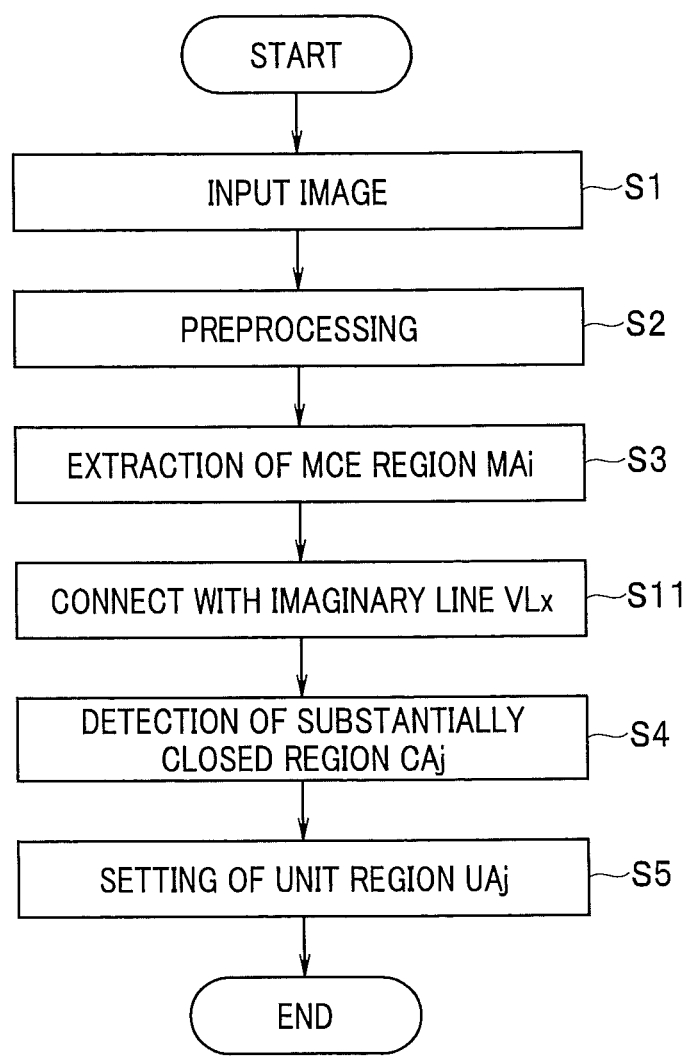
FIG. 14B is a flowchart showing an example of processing content in the modification.

In processing in the present modification, as shown in FIG. 14B, an opening end opened in the MCE region MAj as explained below is detected in step S11 after step S3 in the processing shown in FIG. 6. The imaginary mucous membrane microstructure setting section 43f performs processing for connecting the opening end using an imaginary line VLx. The processing in step S4 is performed after the processing for connecting the opening end using the imaginary line VLx. The other processing is the same as the processing in the first embodiment. Therefore, only differences from the first embodiment are mainly explained.

FIG. 14A shows an example in which the MCE region MA1 is detected or extracted in step S3. An unclosed region indicated by half-tone dot meshing in FIG. 14A is explained as a candidate region CCAj of the substantially closed region CAj. In the present modification, it is possible to identify the candidate region CCAj as a closed region substantially as in the case of the (closed) substantially closed region CAj and set a unit region as in the case of the substantially closed region CAj.

As explained with reference to FIG. 6A, the processing in steps S1 to S3 in FIG. 14B is performed. In step S3, the region extracting section 43c extracts the MCE region MAi (in FIG. 14A, i=1) shown in FIG. 14A and outputs the MCE region MAi to the imaginary mucous membrane microstructure setting section 43f. In the MCE region MAi extracted as explained above, when the MCE region MAi includes unclosed two opening ends, an open region surrounded by portions other than the two opening ends is the candidate region CCAj of the substantially closed region CAj. Therefore, in the case of the candidate region CCAj of such an opening region, a closed region is set by, for example, (detecting the core line CLi as explained below and) connecting the opening ends such that a unit region set as one unit in terms of the in terms of biological histology can be set.

The imaginary mucous membrane microstructure setting section 43f in the present modification performs processing explained below.

Figure 15:
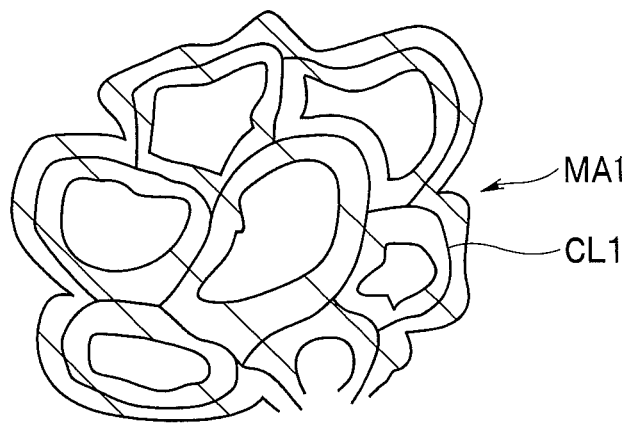
FIG. 15 is a diagram showing an example of a detection result of a core line CL1 in the modification.

First, the imaginary mucous membrane microstructure setting section 43f detects, concerning the MCE region MAj, the core line CLi of the MCE region Mai according to a publicly-known method such as thinning. A detection example of the core line CLi is shown in FIG. 15. Note that, in FIG. 15 to FIG. 18, the MCE region MAi (i=1) is indicated by hatching. Subsequently, when unclosed end points (also considered to be opening ends) are present in the core line CLi detected as shown in step S11 in FIG. 14B, the imaginary mucous membrane microstructure setting section 43f connects the end points using the imaginary line VLx (x≥1).

Figure 16:
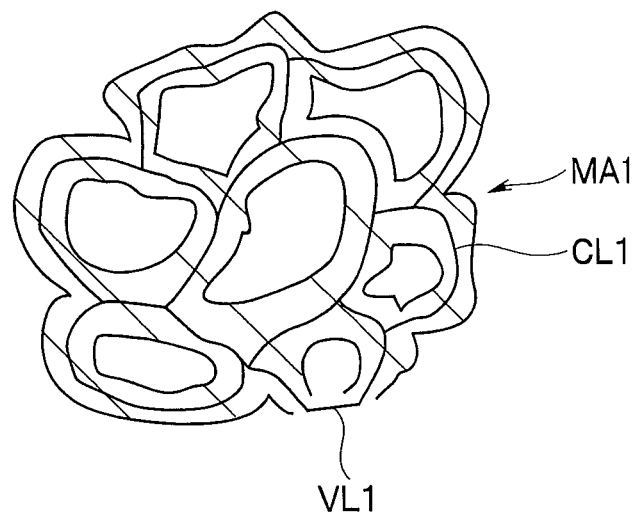
FIG. 16 is a diagram showing an example of an imaginary line VL1 in the modification.

A connection example of the imaginary line VLx is shown in FIG. 16. Subsequently, as in the case in which step S4 in FIG. 6A in the first embodiment is performed, the publicly-known labeling is carried out. Target pixels of the labeling are pixels other than pixels in the region detected as the MCE region MAi and the imaginary line VLx. The following processing is the same as the processing in the first embodiment.

Figure 17:
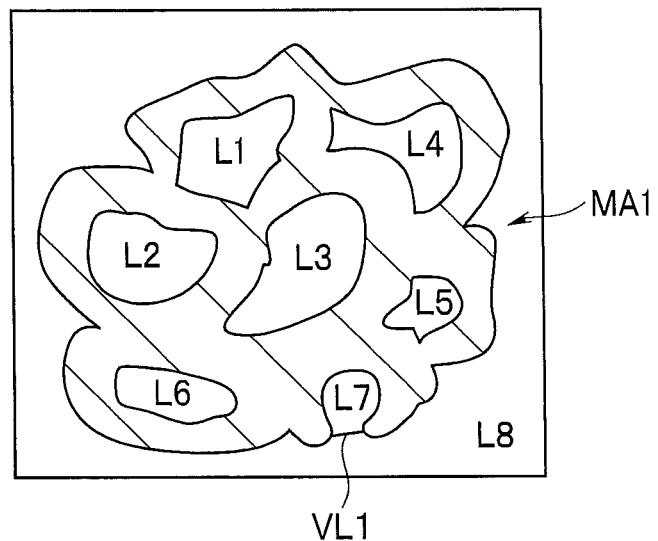
FIG. 17 is a diagram showing an example of a result of labeling performed using the imaginary line VL1 in the modification.

By using the imaginary line VLx, as shown in FIG. 17, it is possible to detect a region of a label L7 that does not form a closed region only in the MCE region MA1. Note that, for the calculation of the region size ASj and the width Wk, the pixels of the imaginary line VLx are not used and only the boundary pixel BPk of the MCE region MAi is used as in the first embodiment. After step S4, the setting of the unit region UAj in step S5 is performed. The processing shown in FIG. 14B ends.

Note that, in the present modification, the end points of the core line CLi are connected by the straight imaginary line VLx. However, the end points may be connected by a curved line or the like.

Figure 18:
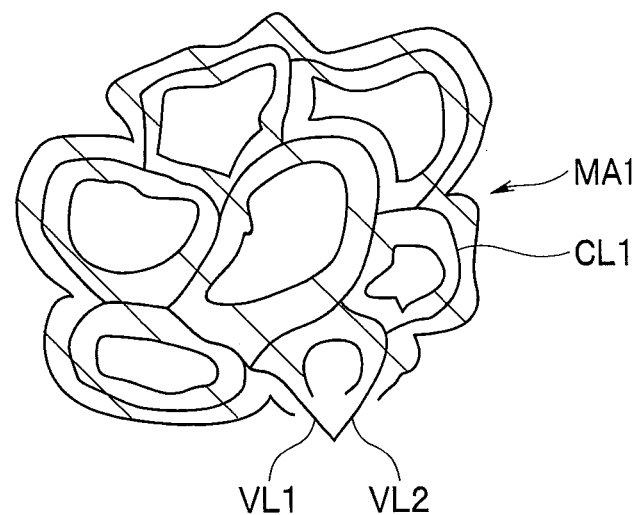
FIG. 18 is a diagram showing a setting example of imaginary lines VL1 and VL2 in the modification.

As shown in FIG. 18, it is also possible to draw the imaginary lines VLx (in FIG. 18, VL1 and VL2) from the end points of the respective core lines CLi in an extending direction of the core line CLi at the end points or an extending direction of the belt-shaped MCE region and detect or identify the substantially closed region CAj using an intersection of the imaginary lines VLx. Consequently, in some case, it is possible to accurately detect the substantially closed region CAj having a complicated shape compared with a case of connecting the end points with the straight line.

According to the present modification, besides effects same as the effects in the first embodiment, even when the MCE region MAi does not assume a complete closed curved line because of, for example, destruction of a tissue due to cancer, it is possible to set the unit region UAj at high accuracy.

Second Embodiment

Next, a second embodiment of the present invention is explained with reference to FIG. 19A to FIG. 27. In an endoscopic image obtained by picking up an image of a mucous membrane microstructure, as shown in a schematic diagram of FIG. 20, in some case, the MCE 51 between the adjacent interval portions 52 is unclear as indicated by a dotted line because of, for example, destruction of a tissue due to cancer or image pickup conditions.

Figure 21:
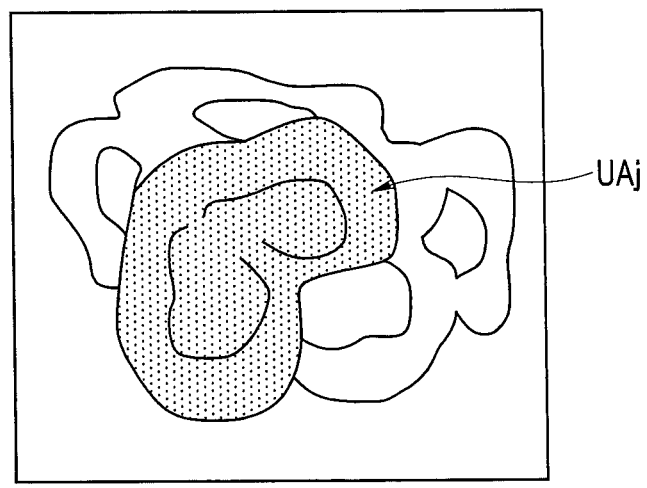
FIG. 21 is a diagram showing an example of a unit region UAj in a case in which processing explained in the first embodiment is applied to FIG. 20.

In the present embodiment, an image processing apparatus and a processing method of the image processing apparatus are explained that can set, in such a case, the respective interval portions 52 as individual unit regions without setting the interval portions 52 as one large unit region UAj as indicated by a half-tone dot meshing pattern in FIG. 21. The image processing apparatus and the processing method are explained below with reference to FIG. 19A to FIG. 27.

The present embodiment is equivalent to a case in which the same processing is performed from step S1 to step S3 in the first embodiment and, in the detection of the substantially closed region CAj and the setting of the unit region UAj in step S4 and subsequent steps, different processing is used. The processing is explained. Therefore, only differences from the first embodiment are explained.

Figure 19A:
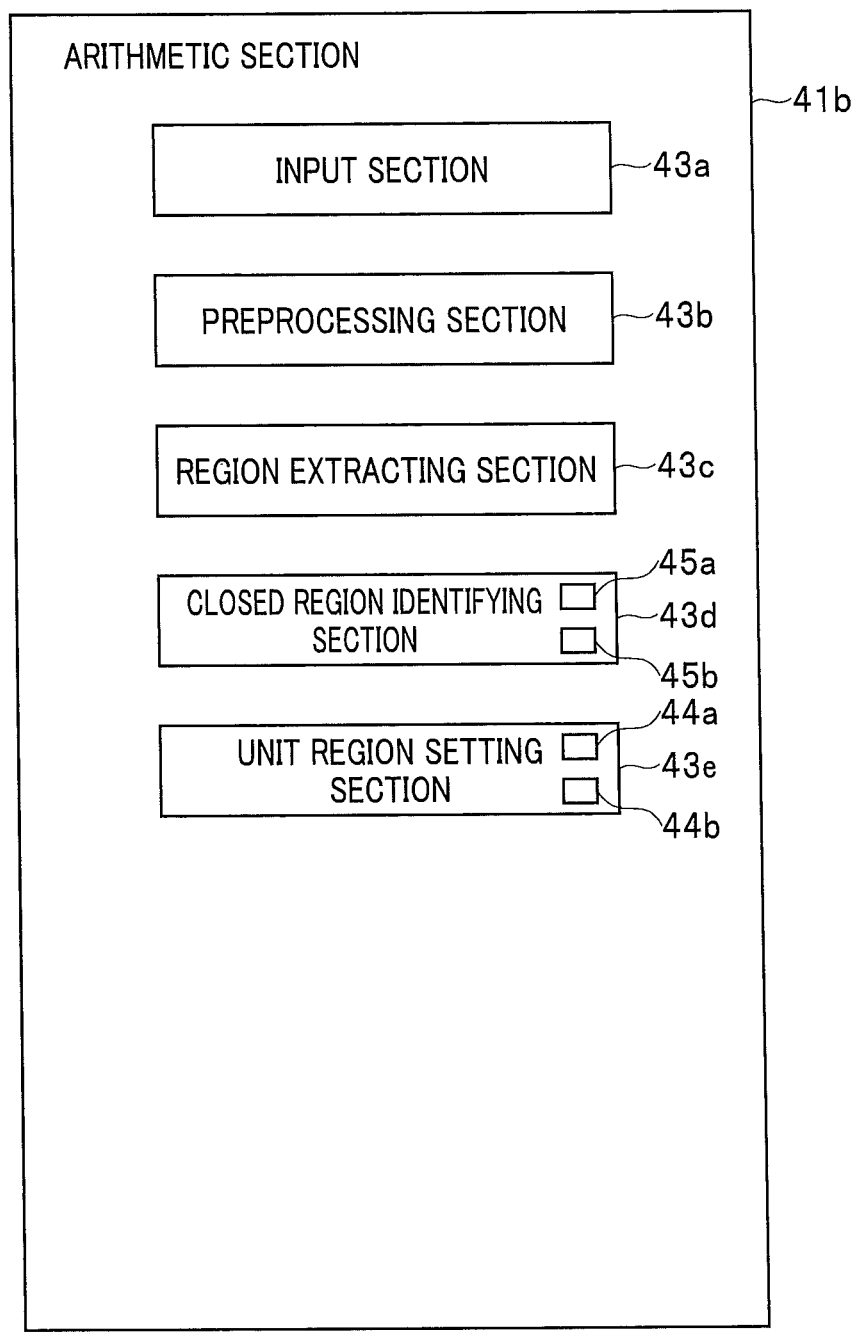
FIG. 19A is a block diagram showing a configuration of an arithmetic section in a second embodiment of the present invention.

A medical image processing device in the present embodiment has a configuration same as the configuration shown in FIG. 1. The arithmetic section 41b in the present embodiment includes, as shown in FIG. 19A, the input section 43a, the preprocessing section 43b, the region extracting section 43c, the closed region identifying section 43d, and the unit region setting section 43e explained above (in the first embodiment).

In the present embodiment, the closed region identifying section 43d includes a convolutional operation section 45a including a matched filter and a substantially closed region pixel candidate detecting/labeling section 45b that detects and labels pixel candidates of a substantially closed region. The substantially closed region pixel candidate detecting/labeling section 45b may be divided into a substantially closed region pixel candidate detecting section that detects pixel candidates of a substantially closed region and a labeling section that labels the detected pixel candidates of the substantially closed region. The unit region setting section 43e in the present embodiment performs setting of a unit region using processing (more specifically, information concerning the matched filter) different from the processing in the first embodiment.

Figure 19B:
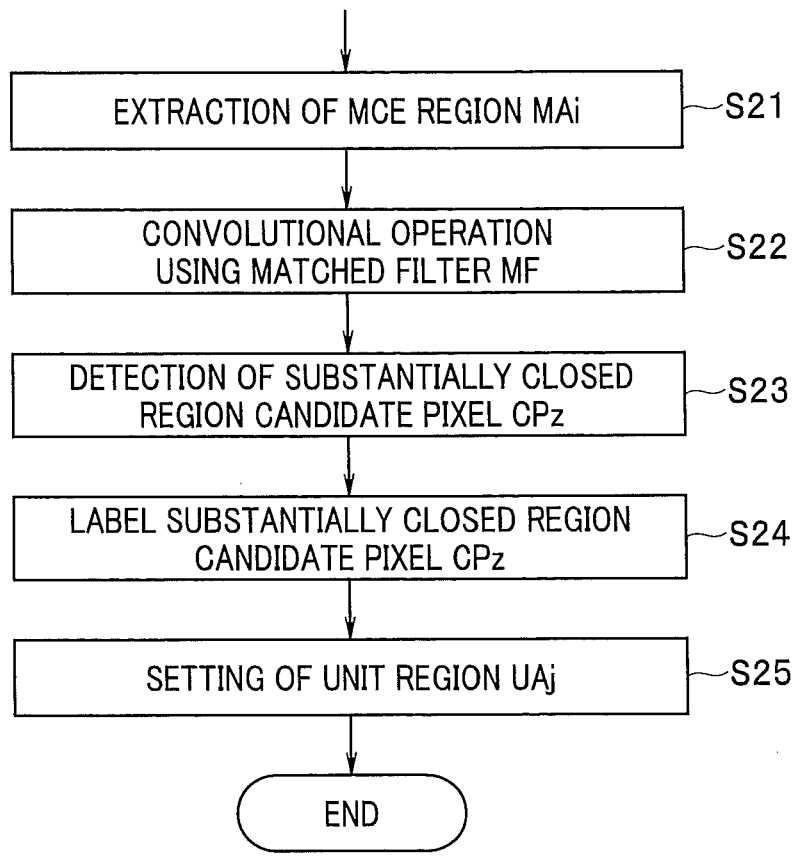
FIG. 19B is a flowchart showing an example of processing content in the second embodiment of the present invention.
Figure 20:
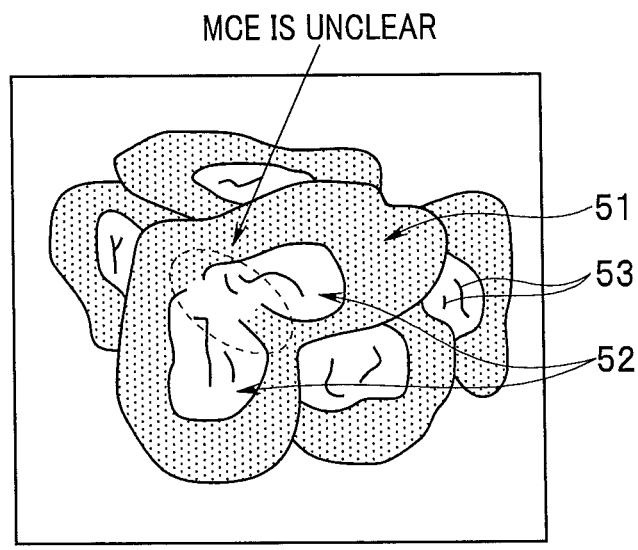
FIG. 20 is a schematic diagram showing an example of a case in which an MCE region is unclear in an endoscopic image.

Processing for setting a unit region is performed according to processing shown in FIG. 19B.

Figure 22:
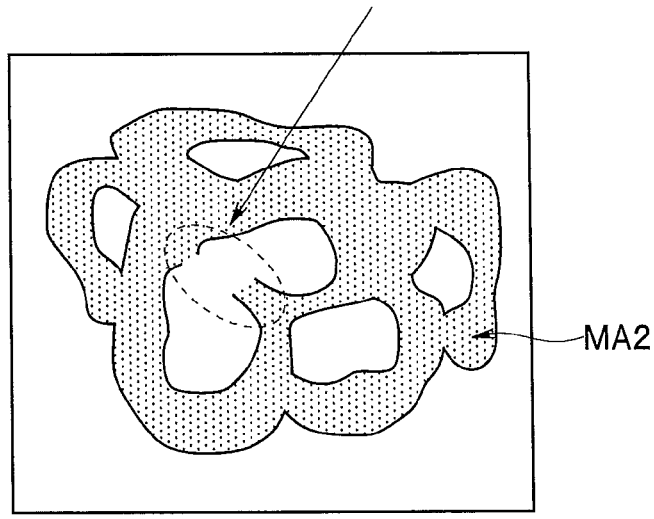
FIG. 22 is a diagram showing an example of a detection result of an MCE region MA2 in the second embodiment.

Step S21 in FIG. 19B is equivalent to the MCE region detection in step S3 in the first embodiment. For example, when the MCE region detection processing is applied to FIG. 20, a detection result of the MCE region MAi shown in FIG. 22 is obtained. At this point, in some case, a region where an MCE is unclear is not detected as the MCE region MAi. Note that, the MCE 51 is indicated by a half-tone dot meshing pattern in FIG. 20. The MCE region MAi shown in FIG. 22 is also indicated by a half-tone dot meshing pattern.

Figure 23:
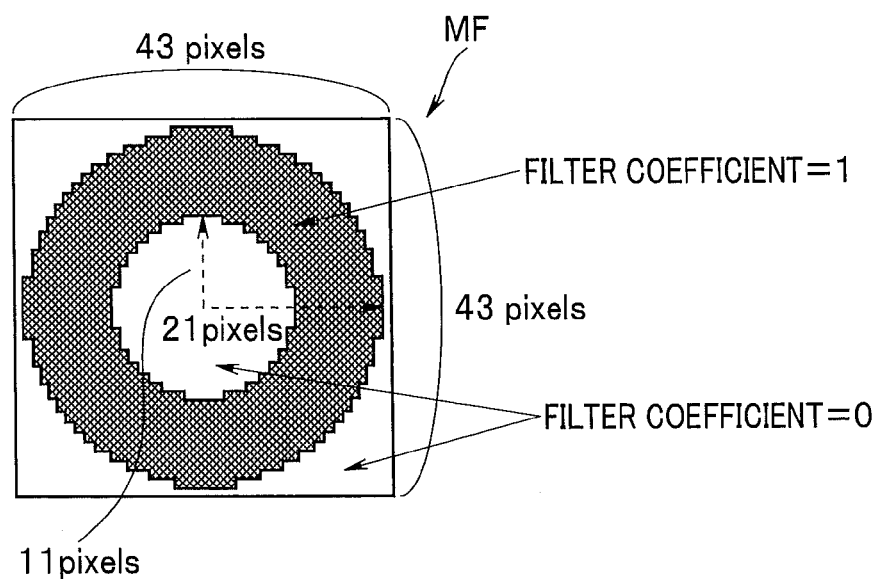
FIG. 23 is a diagram showing an example of a matched filter MF used in the second embodiment.

Subsequently, as shown in step S22, the convolutional operation section 45a of the closed region identifying section 43d carries out a convolutional operation on the MCE region MAi using a matched filter MF. As the matched filter MF, the matched filter MF in which a doughnut shape having a radius of 11 pixels on an inner side and a radius of 21 pixels on an outer side is designed in a rectangular region having a size of 43×43 shown in FIG. 23 is used, for example. Note that a filter coefficient in the matched filter MF is set to 1 in a gray doughnut shape portion and to 0 in a white portion other than the gray doughnut shape portion.

Figure 24:
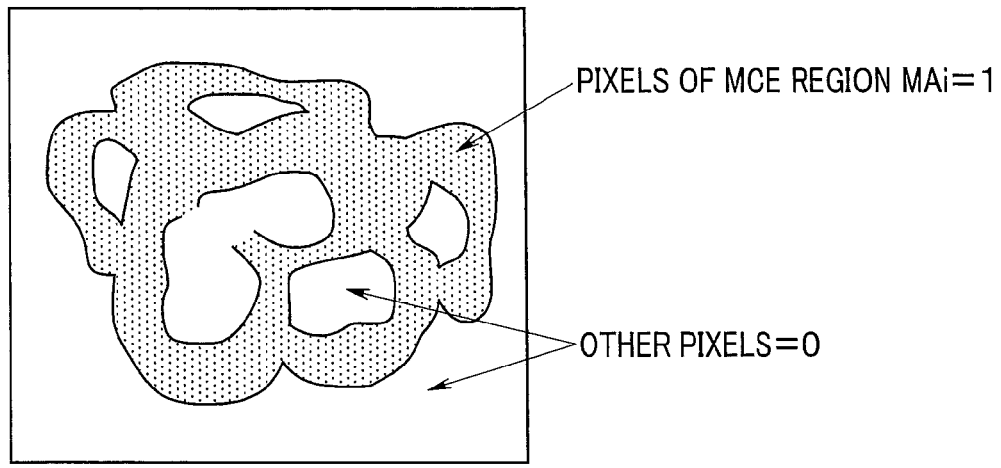
FIG. 24 is a diagram showing an example of pixel value setting of image data in the second embodiment.

When the convolutional operation is applied to image data in the MCE region MAi using the matched filter MF, a pixel value of the image data is set to 1 in pixels belonging to the MCE region MAi indicated by a half-tone dot meshing pattern and to 0 in the other pixels as shown in FIG. 24.

As a result of the convolutional operation, a matched filter response value $RVy$ ($0 \leq y < ISX \times ISY$) is calculated for all pixels of the image data.

Figure 25:
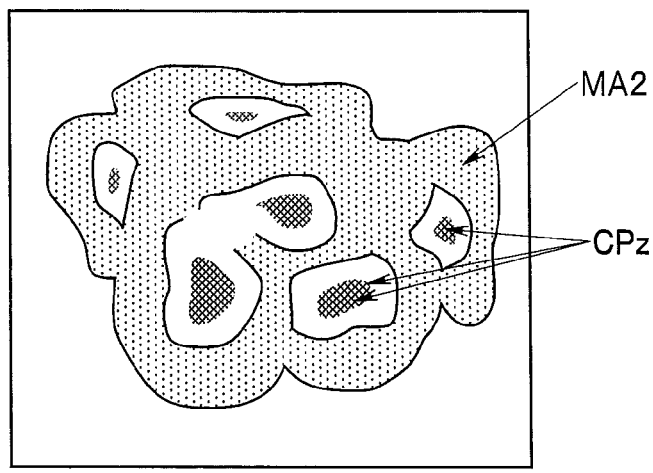
FIG. 25 is a diagram showing an example of a detection result of substantially closed region candidate pixels CPz in the second embodiment.

In the next step S23, the substantially closed region pixel candidate detecting/labeling section 45b of the closed region identifying section 43d detects or identifies, using the following Expression (1), pixels having the high matched filter response value $RVy$, that is, the substantially closed region candidate pixels $CPz$ ($z \geq 1$) using a threshold Thre1. Note that a total $CT$ of coefficients of the matched filter MF in the present embodiment is 908. The threshold Thre1 is set to, for example, 0.6. When the pixels satisfying Expression (1) (=the substantially closed region candidate pixels $CPz$) are detected, a result shown in FIG. 25 is obtained. Note that the substantially closed region candidate pixels $CPz$ represent respective pixels satisfying Expression (1). In FIG. 25, the MCE region MAi is indicated by a half-tone dot meshing pattern.

Matched filter response value $RVy$/(Total $CT$ of coefficients of matched filter MF)>Thre1    (1)

Figure 26:
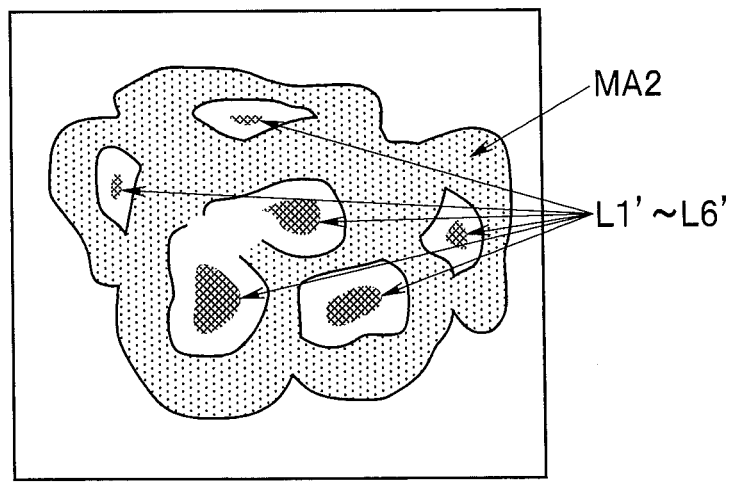
FIG. 26 is a diagram showing an example of a result of labeling for the substantially closed region candidate pixels CPz in the second embodiment.

In the next step S24, the substantially closed region pixel candidate detecting/labeling section 45b carries out the publicly-known labeling on the substantially closed region candidate pixels $CPz$. As a result, for example, the substantially closed region candidate pixels $CPz$ are divided into, for example, six labels (L1' to L6') as shown in FIG. 26.

Figure 27:
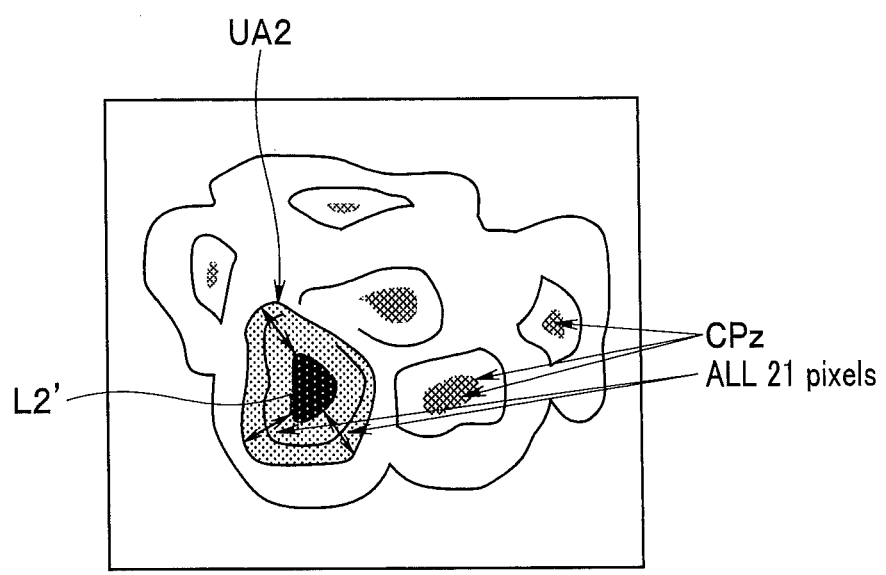
FIG. 27 is a diagram showing an example of setting of a unit region UA2 in the second embodiment.

In the next step S25, the unit region setting section 43e sets, respectively as the unit regions UAj, ranges of a length of a radius of a circle on an outer side of the matched filter MF (in the present embodiment, 21 pixels) from boundary pixels of the respective labels L1' to L6'. In FIG. 27, the unit region UA2 in the case of an example of the label L2' is shown. Unit regions can be set by applying the same processing to the label L3' and the like adjacent to the unit region UA2. Note that, as in the first embodiment and the modification of the first embodiment, the ranges of the respective unit regions UAj are allowed to overlap.

Note that, in the present embodiment, only one kind of the doughnut-shaped filter is used as the matched filter MF. However, a shape, a size, and the number of filters of the matched filter MF are not limited to this. A matched filter having an oval shape, a polygonal shape, or the like may be used. It is also possible to apply a plurality of matched filters having different sizes and shapes and adopt a matched filter having the largest filter response value $RVy$ when the plurality of matched filters are applied.

In the present embodiment, the range of the unit region UAj is set on the basis of the radius of the matched filter MF. However, setting of the range of the unit region UAj is not limited to this method. The range may be calculated from sizes of the respective labels L1' to L6' or the user may set the range in advance.

According to the present embodiment, even when an MCE between adjacent interval portions is unclear because of destruction of a tissue due to cancer, image pickup conditions, or the like and a plurality of unit regions UAj are combined or when end points of the core line CLi extracted using the publicly-known thinning are unclear, it is possible to divide the unit regions UAj to accurately set the range of the respective unit regions UAj.

In explanation of all the embodiments including the case of the modification explained above, inputted entire image data is used as a processing target. However, the user may set any region and set only an inside of a range of the set region as a processing target region.

In the explanation, the G image picked up in the narrow-band observation mode is used. However, other color signals of RGB (more specifically, an R image or a B image) may be used or an operation result calculated by a combination of the respective color signals such as G/R or G(R+G+B) may be used. Image data picked up in an observation mode other than the narrowband observation mode may be used.

In all the embodiments including the case of the modification, an MCE of a pyloric gland mucous membrane of a stomach is explained as an example. However, a target organ is not limited. The embodiments and the modification can be applied to other digestive organs such as a fundic gland mucous membrane of the stomach, an intestinal metaplasia, a large intestine, a small intestine, and an esophagus. More specifically, examples of the target organ include a tumor lesion assuming a tubular or ciliary finding of the large intestine and a Barrett esophagus mucous membrane.

Similarly, a target mucous membrane microstructure is not limited to the MCE. Other mucous membrane microstructures such as a blood vessel, a pit, a surface pattern may be used. In that case, a threshold, a filter coefficient, and the like in detection of the mucous membrane microstructure only have to be changed as appropriate according to the mucous membrane microstructures.

Numerical values of the threshold and the filter coefficient are not limited to numerical values described in this specification. The values may be changed.

Besides, various changes may be performed in a range in which the gist of the invention is not changed.

As explained above, with the medical image processing device and the medical image processing method using the medical image processing device of the present invention, it is possible to set a region divided and extracted as a unit region from an image of a mucous membrane microstructure picked up as a medical image. As a result, it is possible to support observation and diagnosis of the user.

Third Embodiment

In a third embodiment of the present invention, a medical image processing device is explained that sets a unit region from an image of a mucous membrane microstructure picked up as an endoscopic image serving as a medical image and discriminates, from the set unit region, a state of a mucous membrane including at least one or more unit regions as units. FIG. 28 to FIG. 43D relate to the third embodiment of the present invention.

Figure 28:
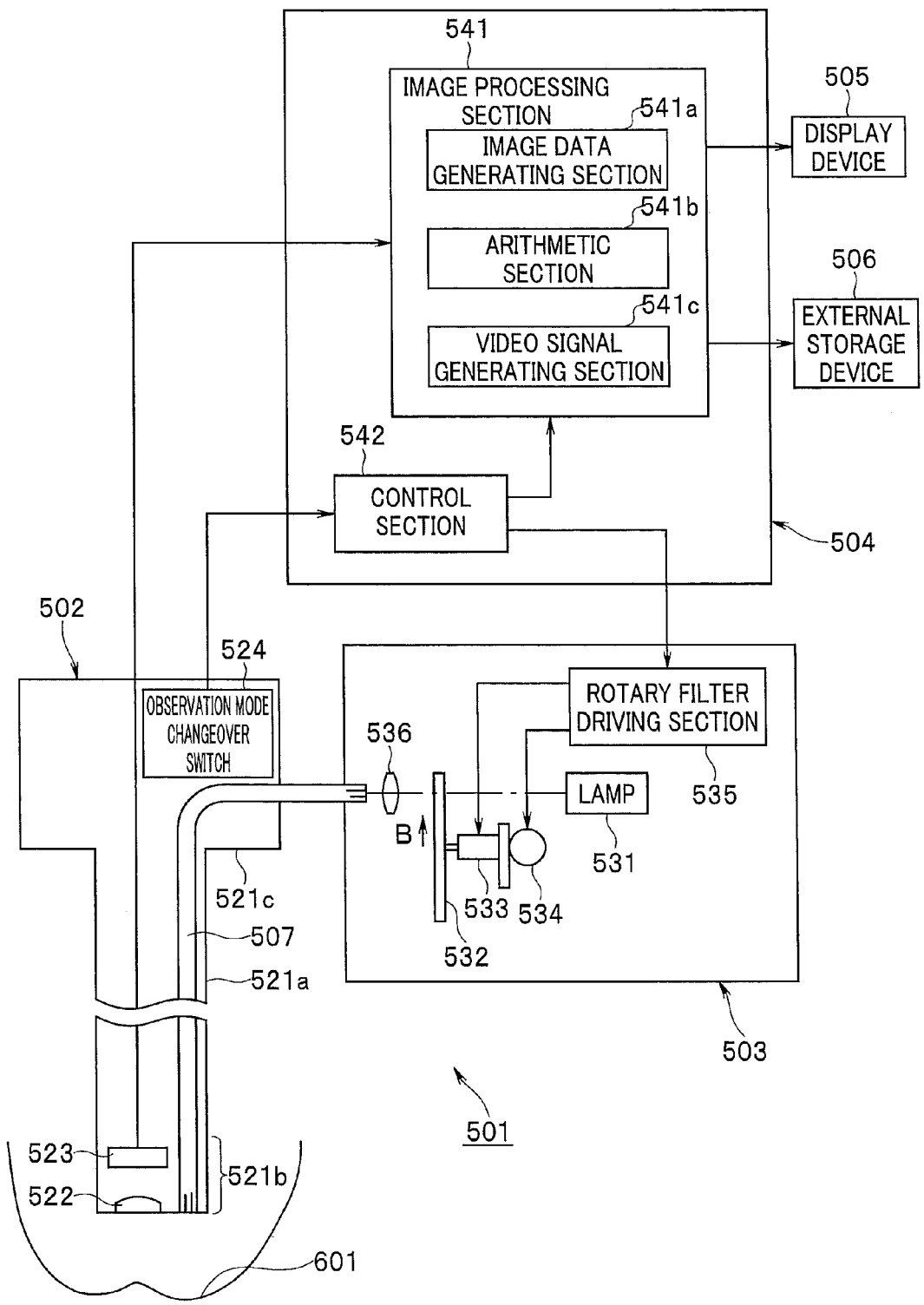
FIG. 28 is a diagram showing an example of a schematic configuration of an endoscope apparatus including a medical image processing device according to a third embodiment of the present invention.

As shown in FIG. 28, an endoscope apparatus 501 includes an endoscope 502 that is inserted into a body cavity of a subject and outputs, as a signal, an image obtained by picking up an image of an object such as a biological tissue 601 in the body cavity, a light source device 503 that emits illumination light for illuminating the biological tissue 601, a processor 504 configuring a medical image processing device that applies various kinds of processing to the output signal from the endoscope 502, a display device 505 that displays an image corresponding to a video signal from the processor 504, and an external storage device 506 that stores an output signal corresponding to a processing result in the processor 504.

The endoscope 502 includes an insertion portion 521*a* including an elongated shape and a dimension insertable into the body cavity of the subject, a distal end portion 521*b* provided on a distal end side of the insertion portion 521*a*, and an operation portion 521*c* provided on a proximal end side of the insertion portion 521*a*. A light guide 507 for transmitting the illumination light emitted in the light source device 503 to the distal end portion 521*b* is inserted through an inside of the insertion portion 521*a*.

One end face (a light incident end face) of the light guide 507 is detachably connected to the light source device 503. The other end face (a light emission end face) of the light guide 507 is arranged near a not-shown illumination optical system provided at the distal end portion 521*b* of the endoscope 502. With such a configuration, the illumination light emitted in the light source device 503 is emitted to the biological tissue 601 in the body cavity after being transmitted through the light guide 507 connected to the light source 503 and the not-shown illumination optical system provided at the distal end portion 521*b*.

At the distal end portion 521*b* of the endoscope 502, an objective optical system 522 that forms an optical image of the object and a charge coupled device (abbreviated as CCD) 523 arranged in an image forming position of the objective optical system 522 and configuring an image pickup section that picks up an optical image and acquires the optical image as an image are provided. In the operation portion 521*c* of the endoscope 502, an observation mode changeover switch 524 capable of performing an instruction for switching an observation mode to any one of a normal light observation mode and a narrowband light observation mode is provided.

The light source device 503 includes a white light source 531 formed by a Xenon lamp or the like, a rotary filter 532 that changes white light emitted from the white light source 531 to frame-sequential illumination light, a motor 533 that drives to rotate the rotary filter 532, a motor 534 that moves the rotary filter 532 and the motor 533 in a direction (a sign B in FIG. 28) perpendicular to an emission optical path of the white light source 531, a rotary filter driving section 535 that drives the motors 533 and 534 on the basis of control by a control section 542 of the processor 504, and a condensing optical system 536 that condenses the illumination light transmitted through the rotary filter 532 and supplies the illumination light to the incident end face of the light guide 507.

Figure 29:
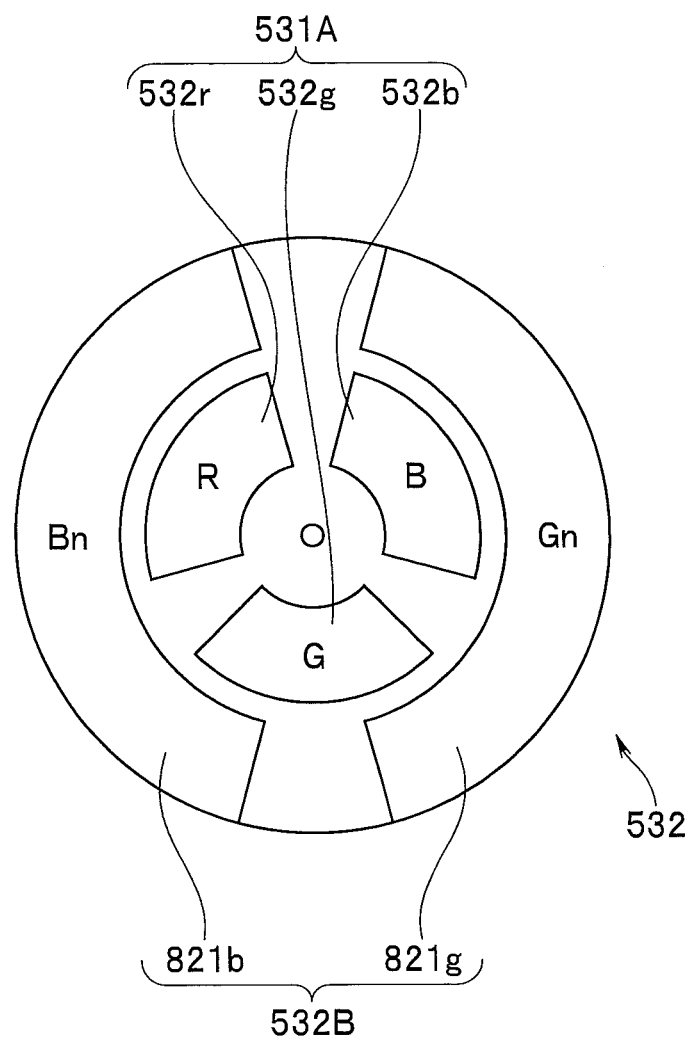
FIG. 29 is a diagram showing an example of a configuration of a rotary filter included in a light source device shown in FIG. 28.

As shown in FIG. 29, the rotary filter 532 is formed in a disk shape, a center of which is a rotating shaft. The rotary filter 532 includes a first filter group 532A including a plurality of filters provided along a circumferential direction on an inner circumference side and a second filter group 532B including a plurality of filters provided along a circumferential direction on an outer circumference side. A driving force of the motor 533 is transmitted to the rotating shaft, whereby the rotary filter 532 rotates. Note that, in the rotary filter 532, portions other than portions where the respective filters of the first filter group 532A and the second filter group 532B are arranged are configured by a light blocking member.

The first filter group 532A includes an R filter 532*r* that allows light in a red wavelength band to pass, a G filter 532*g* that allows light in a green wavelength band to pass, and a B filter 532*b* that allows light in a blue wavelength band to pass, which are respectively provided along the circumferential direction on the inner circumference side of the rotary filter 532.

Figure 30:
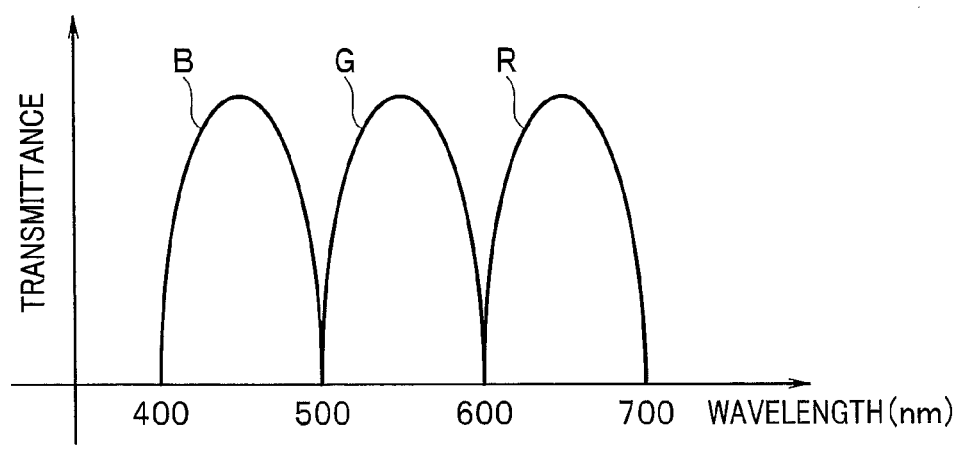
FIG. 30 is a diagram showing an example of transmission characteristic of respective filters included in a first filter group shown in FIG. 29.

For example, as shown in FIG. 30, the R filter 532*r* has a configuration for mainly transmitting light (R light) from 600 nm to 700 nm. For example, as shown in FIG. 30, the G filter 532*g* has a configuration for mainly transmitting light (G light) from 500 nm to 600 nm. Further, for example, as shown in FIG. 30, the B filter 532*b* has a configuration for mainly transmitting light (B light) from 400 nm to 500 nm. Note that, in FIG. 30, the R filter 532*r*, the G filter 532*g*, and the B filter 532*b* are simply indicated by R, G, and B.

The white light emitted in the white light source 531 is transmitted through the first filter group 532A, whereby wide band light for the normal light observation mode is generated.

The second filter group 532B includes a Bn filter 821*b* that allows blue and narrowband light to pass and a Gn filter 821*g* that allows green and narrowband light to pass, which are respectively provided along the circumferential direction on the outer circumference side of the rotary filter 532.

Figure 31:
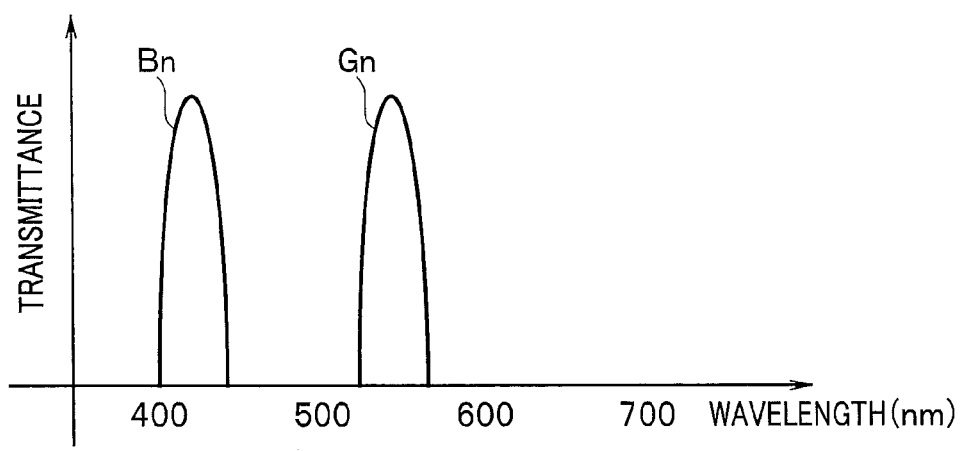
FIG. 31 is a diagram showing an example of transmission characteristics of respective filters included in a second filter group shown in FIG. 29.

For example, as shown in FIG. 31, a center wavelength of the Bn filter 821*b* is set near 415 nm. The Bn filter 821*b* is configured to transmit light (Bn light) in a narrow band compared with the B light.

For example, as shown in FIG. 31, a center wavelength of the Gn filter 821*g* is set near 540 nm. The Gn filter 821*g* is configured to transmit light (Gn light) in a narrow band compared with the G light. Note that, in FIG. 31, the Bn filter 821*b* and the Gn filter 821*g* are simply indicated by Bn and Gn.

The white light emitted in the white light source 531 is transmitted through the second filter group 532B, whereby narrowband lights in a plurality of discrete bands for the narrowband light observation mode are generated.

The processor 504 includes a configuration including a function of the medical image processing device in the present embodiment. More specifically, as shown in FIG. 28, the processor 504 includes an image processing section 541 and a control section 542. The image processing section 541 includes an image data generating section 541*a*, an arithmetic section 541*b*, and a video signal generating section 541*c*.

The image data generating section 541*a* of the image processing section 541 applies processing such as noise removal and A/D conversion to an output signal from the endoscope 502 on the basis of control by the control section 542 to thereby generate image data corresponding to an image obtained in the CCD 523.

The arithmetic section 541*b* of the image processing section 541 performs predetermined processing using the image data generated by the image data generating section 541*a* to thereby extract a mucous membrane microstructure of a living organism out of image data obtained by picking up an image of the biological tissue 601. The arithmetic section 541*b* performs an arithmetic operation for setting a unit region based on predetermined conditions from the mucous membrane microstructure. Further, after setting a discrimination target region including a unit region of attention as a unit region to be paid attention to, the arithmetic section 541*b* performs processing for discriminating a state of a mucous membrane of the discrimination target region on the basis of calculation of a feature value.

Note that, in the present embodiment, it is assumed that the mucous membrane microstructure of the living organism is included in the image data. Unit region setting processing serving as processing for setting, concerning the mucous membrane microstructure, as a unit region, a region or a range set as one unit in terms of biological histology is performed. Details of such unit region setting processing are explained below.

The video signal generating section 541c of the image processing section 541 applies processing such as gamma conversion and D/A conversion to the image data generated by the image data generating section 541a to thereby generate a video signal and outputs the video signal to the display device 505 and the like.

When the control section 542 detects that an instruction for switching to the normal light observation mode is performed on the basis of an instruction of the observation mode changeover switch 524, the control section 542 applies, to the rotary filter driving section 535, control for causing the light source device 503 to emit wideband light for the normal light observation mode. The rotary filter driving section 535 causes, on the basis of the control by the control section 542, the motor 534 to operate to insert the first filter group 532A on an emission optical path of the white light source 531 and retract the second filter group 532B from the emission optical path of the white light source 531.

When the control section 542 detects that an instruction for switching to the narrowband light observation mode is performed on the basis of an instruction of the observation mode changeover switch 524, the control section 542 applies, to the rotary filter driving section 535, control for causing the light source device 503 to emit narrowband lights in a plurality of bands for the narrowband light observation mode.

The rotary filter driving section 535 causes, on the basis of the control by the control section 542, the motor 534 to operate to insert the second filter group 532B on the emission optical path of the white light source 531 and retract the first filter group 532A from the emission optical path of the white light source 531.

That is, with the configuration of the endoscope apparatus 501 explained above, when the normal light observation mode is selected, it is possible to cause the display device 505 to display an image (a normal light image) having a tint substantially the same as a tint obtained when an observation target such as the biological tissue 601 is viewed by naked eyes and further cause the external storage device 506 to store the image. With the configuration of the endoscope apparatus 501 explained above, when the narrowband light observation mode is selected, it is possible to cause the display device 505 to display an image (a narrowband light image) in which a blood vessel near a surface layer included in the biological tissue 601 is highlighted and further cause the external storage device 506 to store the image.

Figure 32:
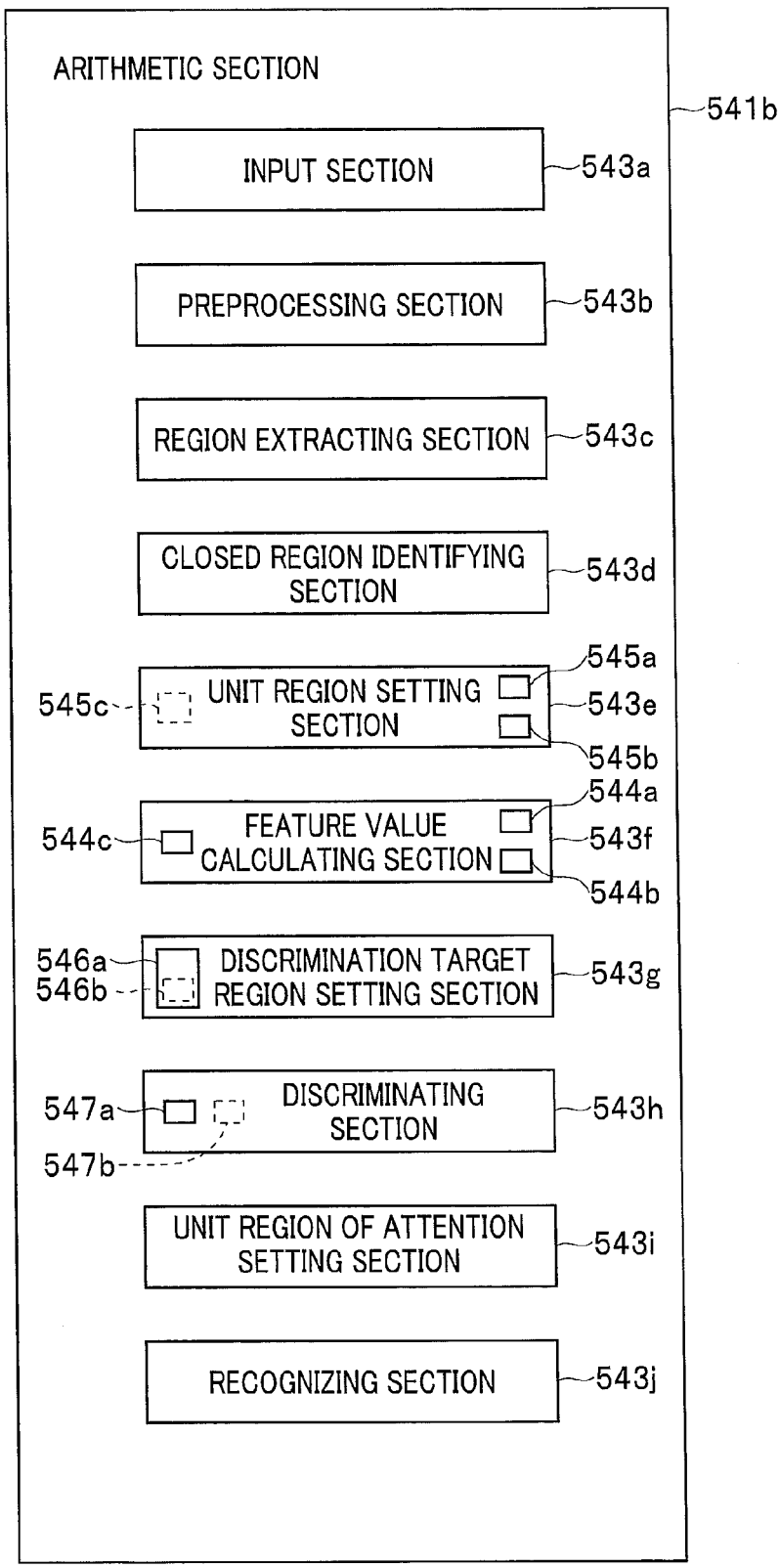
FIG. 32 is a block diagram showing a configuration of an arithmetic section shown in FIG. 28.

As shown in FIG. 32, the arithmetic section 541b configuring the medical image processing device includes an image input section (abbreviated simply as input section) 543a to which (image data of) a biological mucous membrane image serving as medical image information obtained by picking up an image of a biological mucous membrane with the CCD 523 is inputted from the image data generating section 541a, a preprocessing section 543b that applies preprocessing to the biological mucous membrane image inputted to the input section 543a, a region extracting section 543c that extracts a mucous membrane microstructure region corresponding to a mucous membrane microstructure subjected to the preprocessing, and a closed region identifying section (or a substantially closed region identifying section) 543d that identifies at least one closed region (or surrounded region) regarded as being surrounded by the mucous membrane microstructure region.

The arithmetic section 541b further includes a unit region setting section 543e that sets one or more unit regions on the basis of the mucous membrane microstructure region extracted by the region extracting section 543c and the closed region identified by the closed region identifying section 543d and a feature value calculating section 543f that calculates a feature value including a first feature value and the like from the unit region set by the unit region setting section 543e.

The arithmetic section 541b further includes a discrimination target region setting section 543g that sets a discrimination target region from a plurality of unit regions on the basis of the feature value (more specifically, a second feature value) calculated by the feature value calculating section 543f, a discriminating section 543h that discriminates a state of a mucous membrane in the discrimination target region on the basis of the first feature value calculated by the feature value calculating section 543f, and a unit region of attention setting section 543i that sets, when a plurality of unit regions are set by the unit region setting section 543e, from the plurality of unit regions, a unit region of attention serving as one unit region that meets predetermined conditions and to which a user such as a surgeon pays attention. Note that the unit region of attention setting section 543i is not limitedly provided on an inside of the arithmetic section 541b and may be provided on an outside of the arithmetic section 541b.

The feature value calculating section 543f includes a first feature value calculating section 544a that calculates a first feature value serving as a feature value used by the discriminating section 543h to discriminate a state of a mucous membrane including a discrimination target region, a second feature value calculating section 544b that calculates a second feature value serving as a feature value used to set the discrimination target region, and a third feature value calculating section 544c that calculates a third feature value concerning a relation with a unit region of attention with respect to a unit region around the unit region of attention.

Note that the medical image processing device is not limited to a configuration in which the arithmetic section 541b includes the input section 543a and may have a configuration in which the image processing section 541 (e.g., the image data generating section 541a) excluding the arithmetic section 541b includes the input section 543a.

As explained above, the processor 504 functioning as the medical image processing device in the present embodiment is characterized by including the arithmetic section 541b including the input section 543a, the region extracting section 543c, the closed region identifying section 543d, the unit region setting section 543e, (the first feature value calculating section 544a of) the feature value calculating section 543f, and the discriminating section 543h. The components other than the characteristic components may be provided according to necessity. Note that the region extracting section 543c may be configured to extract, without performing the preprocessing, the mucous membrane microstructure region corresponding to the mucous membrane microstructure from the biological mucous membrane image inputted to the input section 543a.

The unit region setting section 543e shown in FIG. 32 includes a width calculating section 545a functioning as a feature value calculating section that calculates, from the mucous membrane microstructure region or the closed region, a width of a belt-shaped mucous membrane microstructure region as a feature value used for range setting for a unit region and a range setting section 545b that sets a range of the unit region on the basis of the feature value of the width.

When a plurality of unit regions are set by the unit region setting section 543e, the discrimination target region setting section 543g sets a discrimination target region from the plurality of unit regions on the basis of the second feature value. The first feature value calculating section 544a performs calculation of the first feature value in the discrimination target region set in the discrimination target region setting section 543g.

The discrimination target region setting section 543g may include a threshold setting section 546a that sets a threshold used in setting a discrimination target region on the basis of the second feature value. The discrimination target region setting section 543g may set a discrimination target region from a unit region of attention and a plurality of unit regions around the unit region of attention on the basis of the threshold set by the threshold setting section 546a and the third feature value. A threshold selecting section 546b may be provided in the threshold setting section 546a as indicated by a dotted line in FIG. 32. One threshold to be actually used may be selected from a threshold of a distance, a threshold of an area, and a threshold of an order serving as a plurality of kinds of thresholds by the threshold selecting section 546b. A discrimination target region may be set using the selected threshold.

The discriminating section 543h includes a threshold-for-discrimination setting section 547a that sets, on the basis of the first feature value calculated by the first feature value calculating section 544a, a threshold for discrimination used for discriminating a state of a mucous membrane.

Note that the input section 543a configuring the arithmetic section 541b may be configured by an input end of image data to the arithmetic section 541b. In the configuration explained above, the region extracting section 543c, the closed region identifying section 543d, the unit region setting section 543e, the feature value calculating section 543f, the discrimination target region setting section 543g, the discriminating section 543h, the unit region of attention setting section 543i, and the like are provided in the arithmetic section 541b. However, the present embodiment is not limited to such a case. The region extracting section 543c, the closed region identifying section 543d, the unit region setting section 543e, the feature value calculating section 543f, the discrimination target region setting section 543g, the discriminating section 543h, the unit region of attention setting section 543i, and the like may be configured using kinds of dedicated hardware that perform the processing of the respective sections.

Next, action of the endoscope apparatus 501 including the processor 504 functioning as the medical image processing device is explained.

First, after turning on power supplies of the respective sections of the endoscope apparatus 501, a surgeon selects the normal light observation mode in the observation mode changeover switch 524. The surgeon inserts, while viewing an image displayed on the display device 505 when the normal light observation mode is selected, that is, an image having a tint substantially the same as a tint obtained when an object is viewed with naked eyes, the endoscope 502 into a body cavity to thereby bring the distal end portion 521b to a part where the biological tissue 601 set as an observation target is present.

When the normal light observation mode is selected by the observation mode changeover switch 524, lights of respective colors, i.e., R light, G light, and B light are sequentially emitted from the light source device 503 to the biological tissue 601. Images corresponding to the lights of the respective colors are respectively acquired in the endoscope 502.

When the image corresponding to the R light, the image corresponding to the G light, and the image corresponding to the B light are inputted, the image data generating section 541a of the image processing section 541 generates image data of color components corresponding to the respective images, respectively.

Figure 33A:
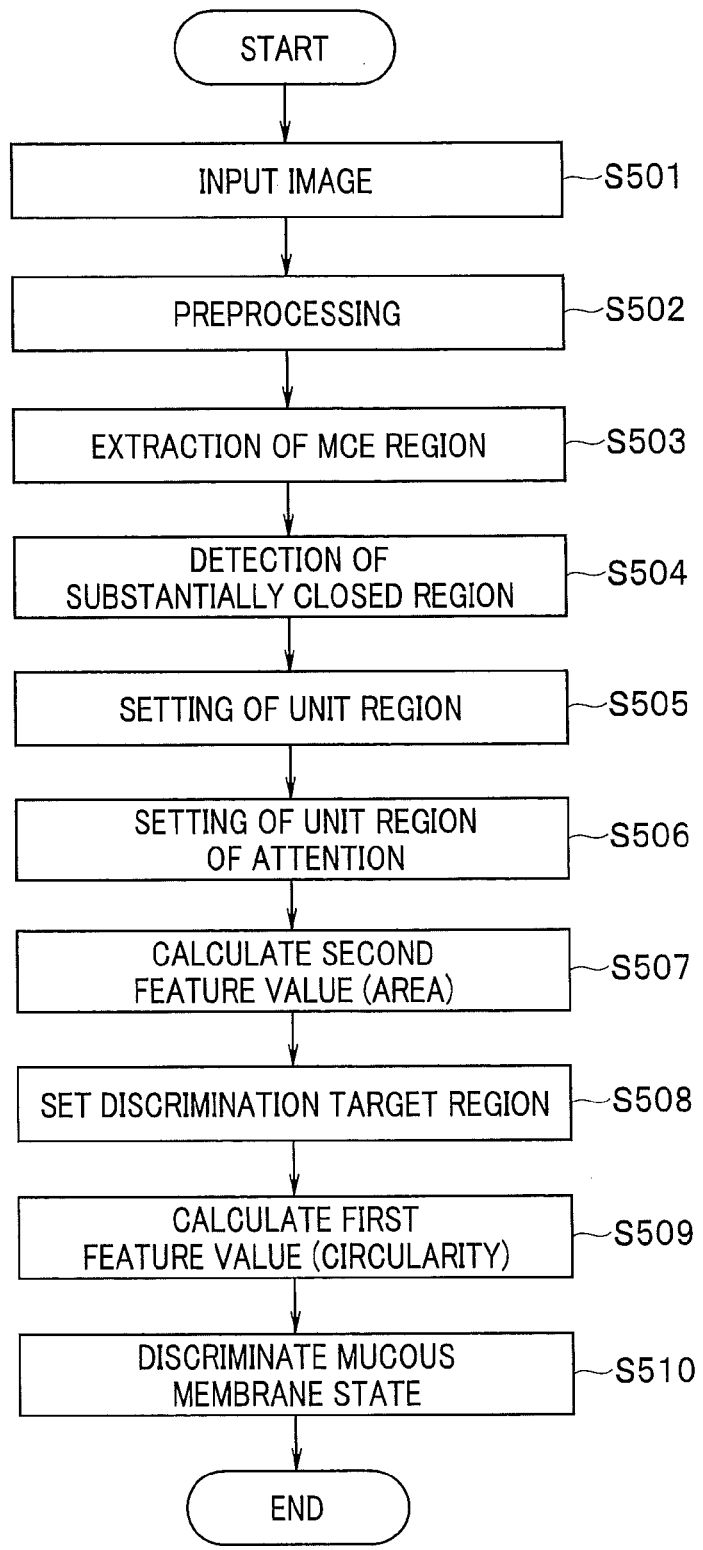
FIG. 33A is a flowchart showing processing content in the third embodiment.

Next, details of an operation for performing the unit region setting processing for setting a unit region included in the arithmetic section 541b of the image processing section 541 are explained. Steps S501 to S505 in FIG. 33A show main processing for performing the unit region setting processing.

In the following explanation, in the present embodiment, in an example of image data obtained by picking up an image of a pyloric gland of a stomach forming an epithelium pattern (an epithelium structure) on the biological tissue 601 in the narrowband light observation mode, the unit region setting processing is explained concerning a case in which a mucous membrane microstructure included in the image data is a marginal crypt epithelium (MCE).

Figure 34:
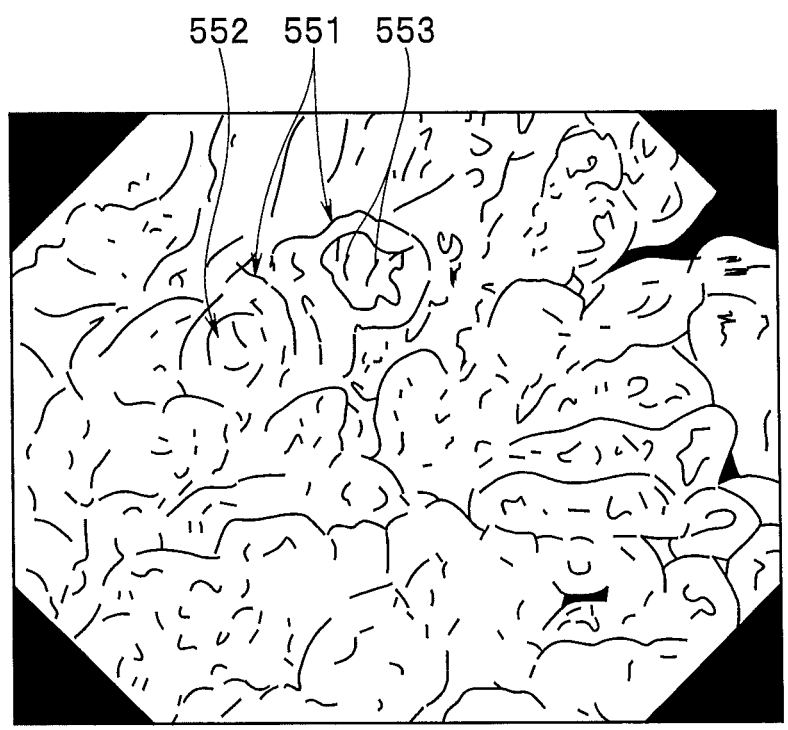
FIG. 34 is a schematic diagram of an endoscopic image.
Figure 35:
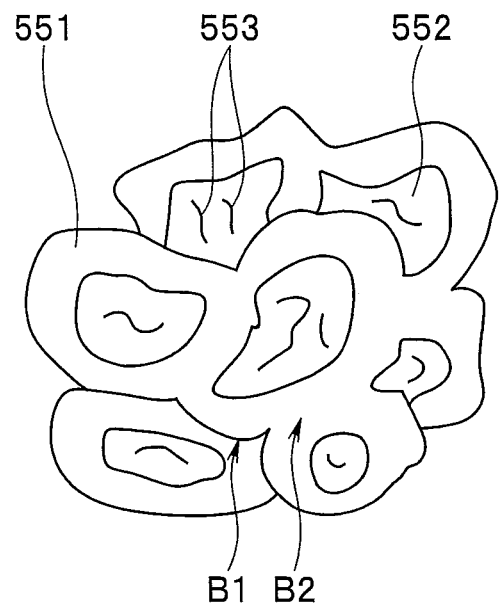
FIG. 35 is an enlarged schematic diagram of a part of FIG. 34.

FIG. 34 schematically shows an image obtained by picking up an image of the pyloric gland of the stomach in the narrowband light observation mode. There is a merit that a structure and the like near a surface layer are displayed more clearly than a case of the wideband light observation mode by picking up an image in the narrowband light observation mode. An image obtained by locally slicing out a part of the image similar to a part of FIG. 34 or a part of FIG. 34 is shown in FIG. 35. In FIG. 34 and FIG. 35, a plurality of belt-shaped MCEs 551 are present overlapping one another. An interval portion 552 is present in a region (usually a closed region) on an inner side surrounded by the MCE 551. Blood vessels 553 run in the interval portion 552.

Further, image data picked up by the endoscope 502 depends on image pickup conditions such as a distance and an angle and a state of a mucous membrane itself. Therefore, a boundary of one MCE 551 is clear in some case and a boundary of the MCE 551 adjacent to the MCE 551 is unclear in other cases. In FIG. 35, for example, a boundary of the MCE 551 indicated by a sign B1 is clear but a boundary of the MCE 551 indicated by a sign B2 is unclear.

As shown in step S501 in FIG. 33A, image data generated by the image data generating section 541a is inputted to the preprocessing section 543b in the arithmetic section 541b from the input section 543a. Note that image data in the present embodiment and the other embodiments is formed by three (color component) images of RGB, a size (lateral and longitudinal numbers of pixels) of which is ISX×ISY. Each of the respective images of R, G, and B includes 8-bit gradations formed by values 0 to 255. For example, ISX×ISY=640×480.

In the next step S502, the preprocessing section 543b applies preprocessing such as noise suppression and inverse gamma correction to the inputted image data. In the present embodiment, as the noise suppression, publicly-known median filtering (rearranging pixel values in a mask including a pixel of attention according to magnitudes and replacing a value of the pixel of attention with a median) is applied in a mask size of sizes 3×3.

Note that gamma correction is nonlinear processing applied to give visually linear gradation when an image is displayed on a monitor or the like. The inverse gamma correction resets the nonlinear gradation to the original linear gradation. Therefore, when the gamma correction is not applied to image data inputted to the preprocessing section 543b, the inverse gamma correction is unnecessary.

The image data subjected to the preprocessing is outputted to the region extracting section 543c. As shown in step S503, the region extracting section 543c performs extraction of a belt-shaped MCE region MBi (i≥1) as a mucous membrane microstructure region corresponding to a mucous membrane microstructure.

Figure 33B:
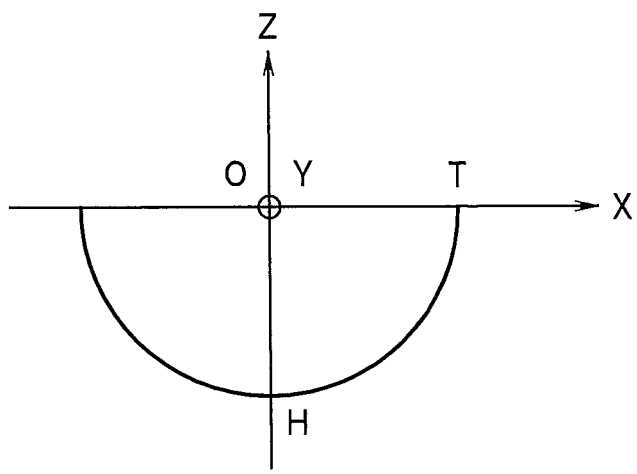
FIG. 33B is a diagram showing a semielliptical shape used in template matching.

As an extraction method for the MCE region MBi, for example, a structural component extraction method by template matching described in Japanese Patent No. 4409166 is used. FIG. 33B shows a semielliptical shape used in the template matching.

Note that a width T of a semielliptical shape used for creation of a template is set as T=3 to 9 (at an interval of 1.0). A depth H of the semielliptical shape may be set to a value corresponding to the depth of the MCE region MBi. As the other parameters, values described in the embodiment of the Japanese Patent No. 4409166 only have to be used as they are.

Figure 36:
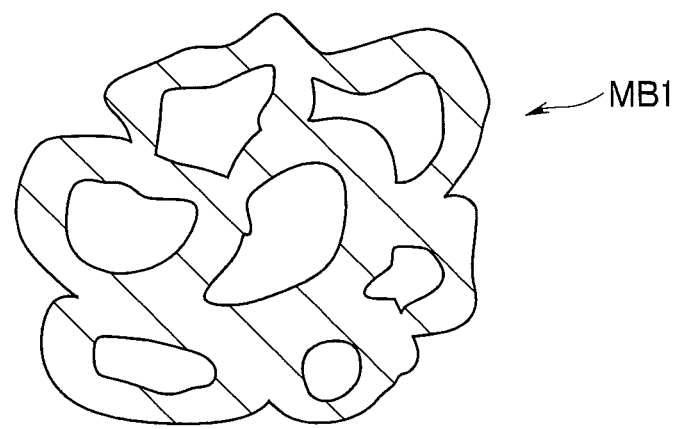
FIG. 36 is a diagram showing an example of a detection result of an MCE region MB1 in the third embodiment.

As in the embodiment of Japanese Patent No. 4409166, processing only has to be carried out targeting a G image among three images of RGB. Such an extraction method is applied to the image data shown in FIG. 34 or FIG. 35 to extract an MCE region MB1, for example, as shown in FIG. 36. The extracted MCE region MB1 is outputted to the closed region identifying section 543d. Note that the extracted MCE region MB1 is indicated by hatching in FIG. 36.

In the next step S504 in FIG. 33A, the closed region identifying section 543d performs processing for detecting or identifying a substantially closed region CBj (j≥1) substantially surrounded by the MCE region MBi detected as the mucous membrane microstructure region (in other words, as a closed region surrounded by or a substantially closed region regarded as being surrounded by the MCE region MBi).

Note that, in the third embodiment, the substantially closed region CBj is a surrounded closed region. However, the third embodiment may be applied to the case of the substantially closed region regarded as being surrounded as explained above.

Figure 37:
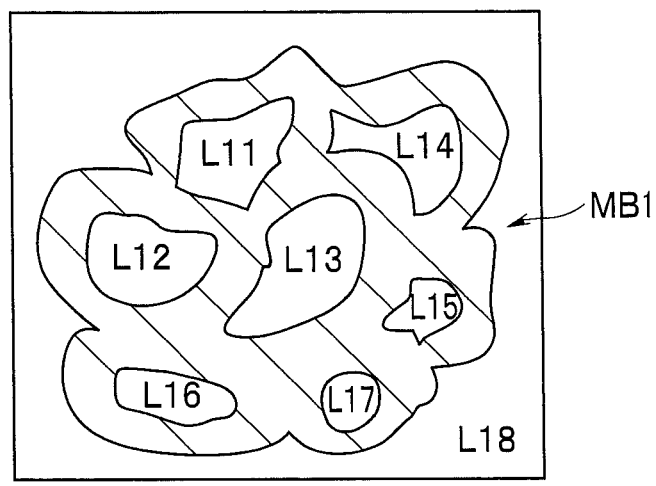
FIG. 37 is a diagram showing an example of a result of labeling of a region including the MCE region MB1 in the third embodiment.

In order to perform the processing in step S504, publicly-known labeling is carried out for regions of pixels other than the region detected as the MCE region MBi. When the labeling is applied to a detection result of the MCE region MB 1 shown in FIG. 36, the MCE region MB1 is divided into eight labels L11 to L18 as shown in FIG. 37. Note that, in FIG. 37, the MCE region MB1 is indicated by hatching.

Figure 38:
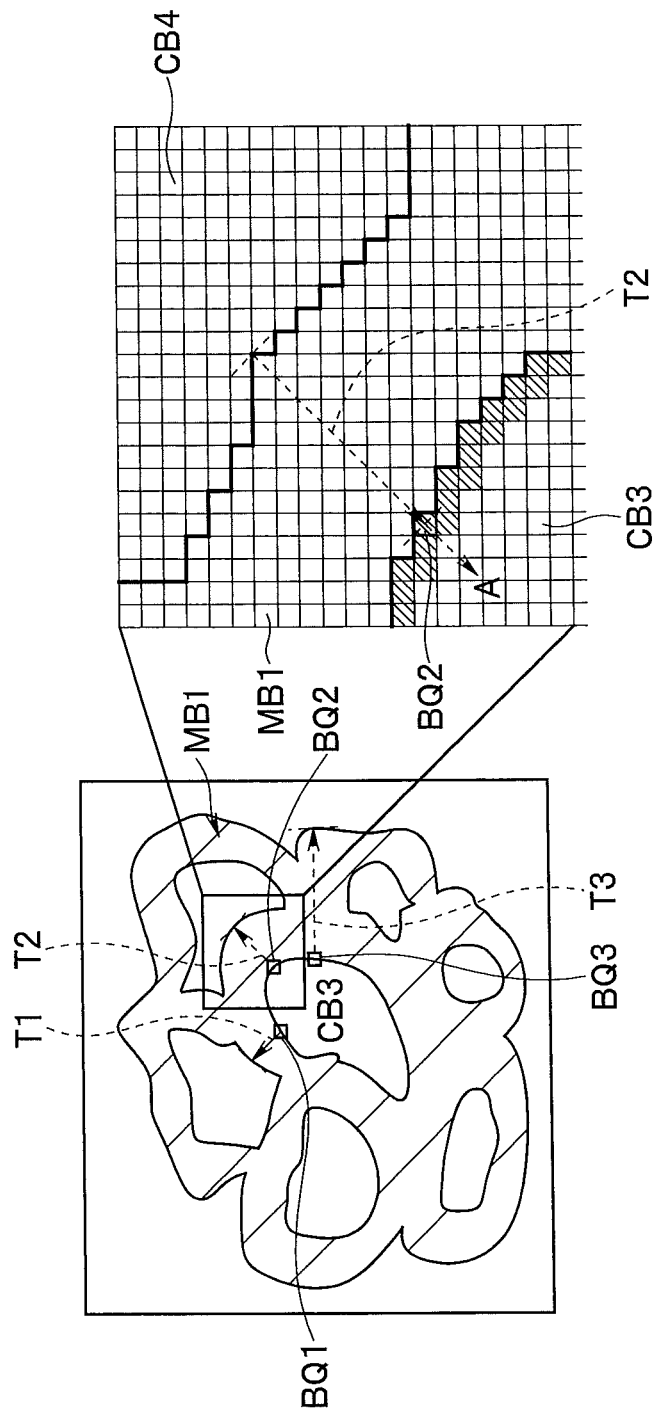
FIG. 38 is a diagram showing an example of a case in which a width Tk is calculated as a feature value of an MCE region MBi in the third embodiment.

Among the labels L11 to L18, the labels other than the label L18 including outermost peripheral pixels (pixels, X coordinates of which are 0 or 639, and pixels, Y coordinates of which are 0 or 479) of image data in pixels in the label are set as the substantially closed region CBj. In an example of application to FIG. 37, the labels L11 to L17 excluding the label L18 are respectively substantially closed regions CB1 to CB7. Although not all of CB1 to CB7 are clearly indicated by signs in FIG. 37, for example, in FIG. 40, closed regions of the labels L12 and L13 are shown as CB2 and CB3. In FIG. 38, closed regions of the labels L13 and L14 are clearly shown as CB3 and CB4. Information concerning the substantially closed regions CB1 to CB7 detected or identified by the closed region identifying section 543d is outputted to the unit region setting section 543e.

In the next step S505, the range setting section 545b of the unit region setting section 543e calculates a width serving as a feature value of the MCE region MBi on the basis of the substantially closed region CBj and performs processing for setting a range of a unit region UBj.

First, the width calculating section 545a of the unit region setting section 543e calculates a width Tk (k≥1) serving as a feature value of the MCE region MBi adjacent to one substantially closed region CBj. For example, the width calculating section 545a scans pixels in a direction opposite to the substantially closed region CBj adjacent to the MCE region MBi from a boundary pixel BQk (e.g., on the substantially closed region CBj side) with the MCE region MBi adjacent to the substantially closed region CBj and counts the number of pixels of the MCE region MBi to calculate the width Tk in the boundary pixel BQk.

FIG. 38 shows an example in which widths T1, T2, and T3 in, for example, three representative directions in a case in which the substantially closed region CB3 (in the case of j=3) is set as a target are calculated and an enlarged view of a case in which the width T2 is calculated in one direction with attention paid to a boundary pixel BQ2. Note that, the MCE region MB1 is indicated by hatching in FIG. 38.

In FIG. 38, a state is shown in which, when three boundary pixels BQ1, BQ2, and BQ3 are set in an outer periphery of the substantially closed region CB3, the widths T1, T2, and T3 of the MCE region MB1 adjacent to the substantially closed region CB3 are calculated respectively from the respective boundary pixels BQ1, BQ2, and BQ3. In the following explanation, concerning the case of one boundary pixel BQ2, the width T2 is calculated with reference to an enlarged view of a part including the boundary pixel BQ2.

As shown in an enlarged view of FIG. 38, the substantially closed region CB3 adjacent to the boundary pixel BQ2 is located in a left downward direction (a direction indicated by A in FIG. 38). Therefore, pixels are scanned in a right upward direction, which is a direction opposite to the left downward direction, from the boundary pixel BQ2. When the number of pixels of the MCE region MB1 is counted while the pixels are scanned in the right upward direction (in FIG. 38, the substantially closed region CB4 side), the number of pixels is 8. This is a value of the width T2.

Note that, when the substantially closed regions CBj adjacent to the boundary pixel BQk are present in a plurality of pixels, the pixels are scanned in directions of the respective substantially closed regions CBj. A smallest number of pixels is set as a value of the width Tk. In FIG. 38, only the three pixels of the boundary pixels BQ1, BQ2, and BQ3 discretely shown in the substantially closed region CB3 are illustrated. However, the calculation of the width Tk is carried out in all the boundary pixels BQk.

Next, an average of the widths Tk calculated in all the boundary pixels BQk is set as a region size BSj of an MCE region MBi adjacent to the substantially closed region CBj. The range setting section 545b sets or determines, on the basis of the calculation of the width by the width calculating section 545a, as a range of the unit region UBj, a region obtained by combining the substantially closed region CBj and the MCE region MBi located in a range of the region size BSj from the substantially closed region CBj.

Figure 39:
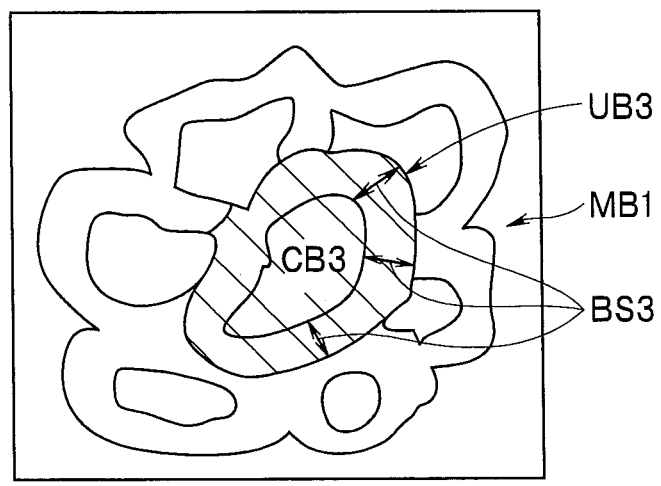
FIG. 39 is a diagram showing an example of setting of a unit region UB3 in the third embodiment.

FIG. 39 shows an example of a unit region UB3 set when the substantially closed region CB3 explained with reference to FIG. 38 is set as a target and a region size BS3 of the MCE region MB1 adjacent to the substantially closed region CB3. Note that the set unit region UB3 is indicated by hatching in FIG. 39. The unit region UB3 shown in FIG. 39 is a region obtained by combining the substantially closed region CB3 and the belt-shaped MCE region MB 1 located in a range of the region size BS3, which is determined by the average of the width, from an outer peripheral boundary of the substantially closed region CB3 to surround the substantially closed region CB3.

In the above explanation, the processing or the method for calculating, from the substantially closed region CBj, the width Tk serving as the feature value of the belt-shaped MCE region MBi surrounding the substantially closed region CBj and setting the range of the unit region UBj is illustrated targeting the substantially closed region CBj (of j=3). However, actually, the processing or the method is carried out for all the substantially closed regions CBj.

Figure 40:
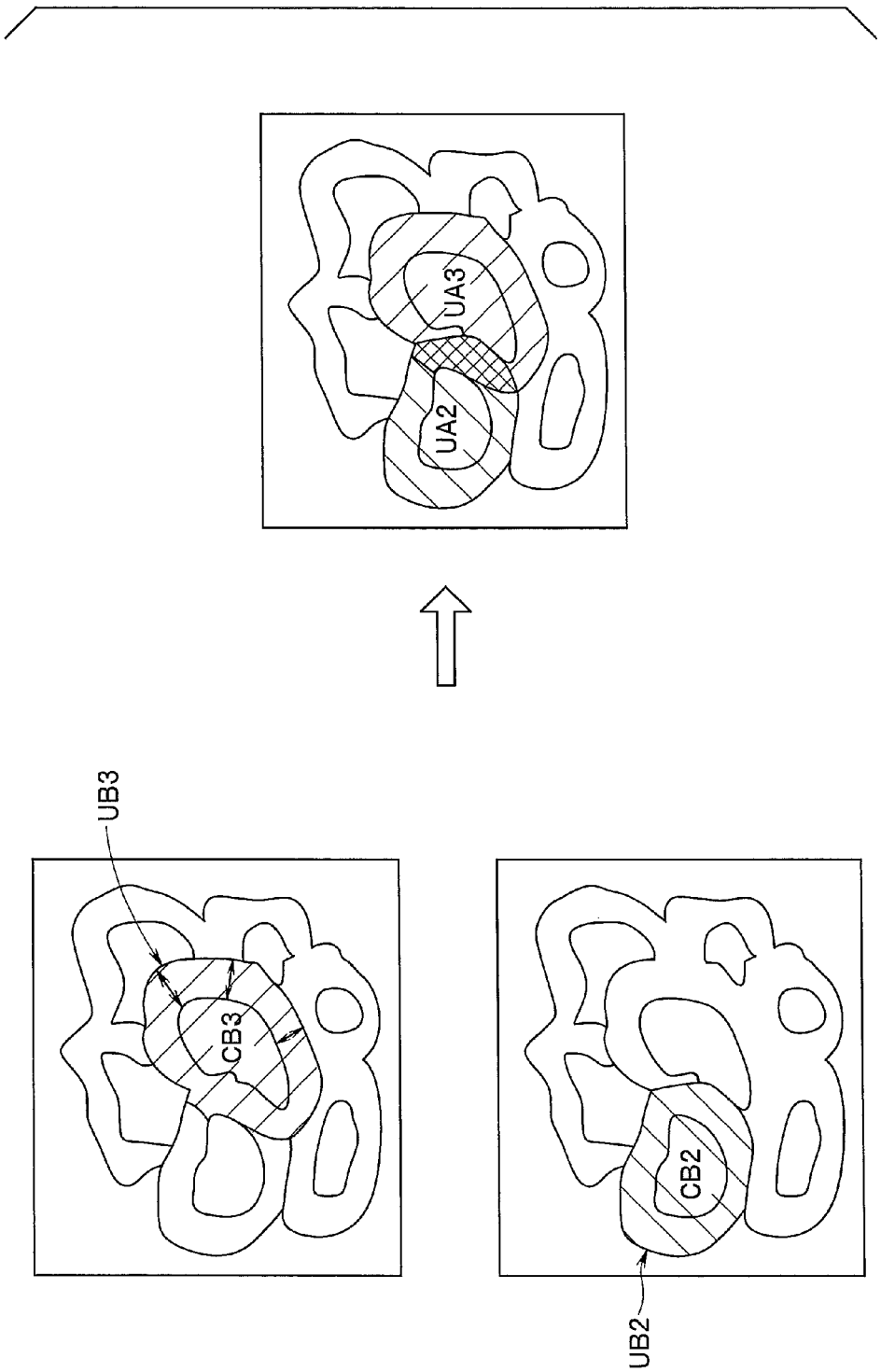
FIG. 40 is a diagram showing an example in which unit regions UB2 and UB3 overlap in the third embodiment.

When the processing or the method is carried out, as shown in FIG. 40, a range of certain unit region UB3 is allowed to overlap a range of another unit region UB2.

According to FIG. 40, the unit region UB3 set from the substantially closed region CB3 explained with reference to FIG. 39 is indicated by hatching. According to FIG. 40, the unit region UB2 set from the substantially closed region CB2 according to processing same as the processing in the case of the substantially closed region CB3 is indicated by hatching.

According to FIG. 40, the unit region UB2 and the unit region UB3 overlap in a region indicated by cross-hatching. However, when unit regions are set, a part of a certain unit region is allowed to overlap a part of another unit region (more specifically, a belt-shaped MCE region) in this way. In other words, when the unit region setting section 543e performs the setting of unit regions by setting MEC regions to surround a plurality of closed regions, the unit region setting section 543e performs the setting of unit regions independently for each of the plurality of closed regions. As a result, as shown in FIG. 40, MEC regions of parts of the unit regions are allowed to overlap each other.

Consequently, a region set as one unit in terms of the biological histology can be set as the unit region UBj from the image data. In other words, one closed region like the interval portion 552 including the blood vessels 553 or the substantially closed region CBj regarded as a closed region and one MCE region MBi formed in a belt-shaped closed loop shape surrounding the substantially closed region CBj can be set as the unit region UBj from the image data. Note that, by applying setting processing for a unit region to a processing target region in an image obtained by picking up an image of a biological tissue, it is possible to identify the processing target region (or a part of the processing target region) as a unit region group (or a unit region set region) with a unit region set as a unit. Therefore, the unit region setting section 543e can also be regarded as a unit region identifying section that identifies the processing target region as a set of unit regions with a unit region set as a unit.

When the processing of the setting of the unit region UBj in step S505 in FIG. 33A ends in this way, by calculating a feature value of the unit region UBj as explained below, it is possible to set a discrimination target region Ad including the unit region UBj and perform processing for discriminating a state of a mucous membrane including the set discrimination target region Ad.

Figure 41A:
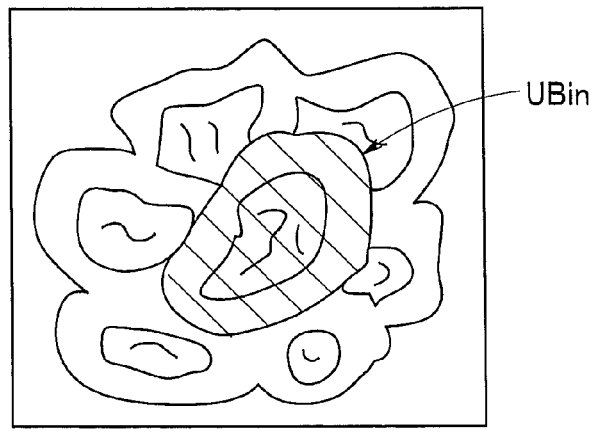
FIG. 41A is a diagram showing a set unit region of attention.

Therefore, in step S506 after step S505, the unit region of attention setting section 543i sets, as a unit region of attention UBin, one unit region present at a distance closest to a center of an image. FIG. 41A shows an example of the unit region of attention UBin set as meeting this condition C1 (i.e., one unit region present at a closest distance to a center of an image).

In the example shown in FIG. 41A, the unit region UB3 shown in FIG. 40 is set as the unit region of attention UBin.

As shown in FIG. 33A, in the next step S507, the second feature value calculating section 544b calculates a largest value of a width of an external shape (a contour) of the unit region of attention UBin as a second feature value concerning a size of a region size and a shape of a region of the unit region of attention UBin. The second feature value calculating section 544b outputs the calculated maximum value of the width to the discrimination target region setting section 543g. Note that a feature value calculated by the second feature value calculating section 544b is not limited to a maximum of the width of the unit region of attention UBin and may be an average of the width or an area may be calculated as explained below. A perimeter of the unit region of attention UBin may be calculated rather than the area.

In the next step S508, the discrimination target region setting section 543g sets, as the threshold of the distance set by the threshold setting section 546a, a circular region Ac having a diameter, for example, three times as large as the calculated maximum Tmax of the width and sets an inner side of the circular region Ac as the discrimination target region Ad. That is, the threshold setting section 546a sets a threshold of a distance from the maximum of the width serving as the second feature value.

Figure 41B:
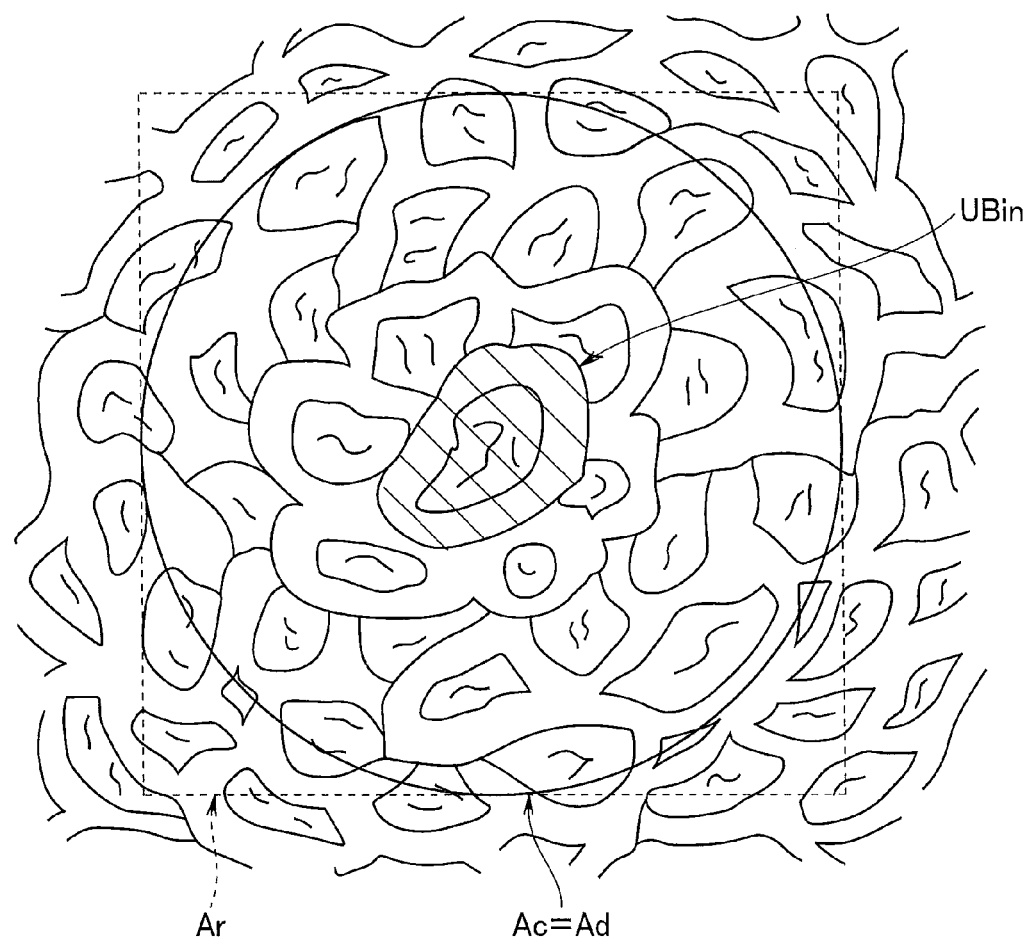
FIG. 41B is a diagram showing a setting example of a discrimination target region Ad set to include the unit region of attention.

In FIG. 41B, a setting example is shown in which an inside of the circular region Ac set in step S508 (i.e., equal to or smaller than the threshold of the distance) is set as the discrimination target region Ad (in FIG. 41B, abbreviated as Ac=Ad, however, the inner side of Ac is Ad). In the example shown in FIG. 41B, the circular region Ac centering on (a center of gravity position of) the unit region of attention UBin and having a radius three times as large as ½ of the calculated maximum Tmax of the width is set as the discrimination target region Ad. Unit regions included on an inner side of a circular region Ac are set as a unit region group of the discrimination target region Ad. In FIG. 41B, a region included in the discrimination target region Ad on an outer side of the region shown in FIG. 41A is also illustrated.

Note that the inner side of the circular region Ac is not limitedly set as the discrimination target region Ad. For example, a unit region, at least a part of which is included in the circular region Ac, may be set as a unit region of the discrimination target region Ad. A unit region, a half or more of a region of which is included in the circular region Ac, may be set as a unit region of the discrimination target region Ad. A unit region substantially entirely included in the circular region Ac may be set as a unit region of the discrimination target region Ad.

After setting (determining) the discrimination target region Ad, the discrimination target region setting section 543g outputs information concerning the setting (determination) to the first feature value calculating section 544a of the feature value calculating section 543f.

As shown in step S509 in FIG. 33A, the first feature value calculating section 544a calculates, as a first feature value of the discrimination target region Ad, for example, circularities of respective unit regions included in the discrimination target region Ad and calculates average circularity of the circularities.

Figure 42:
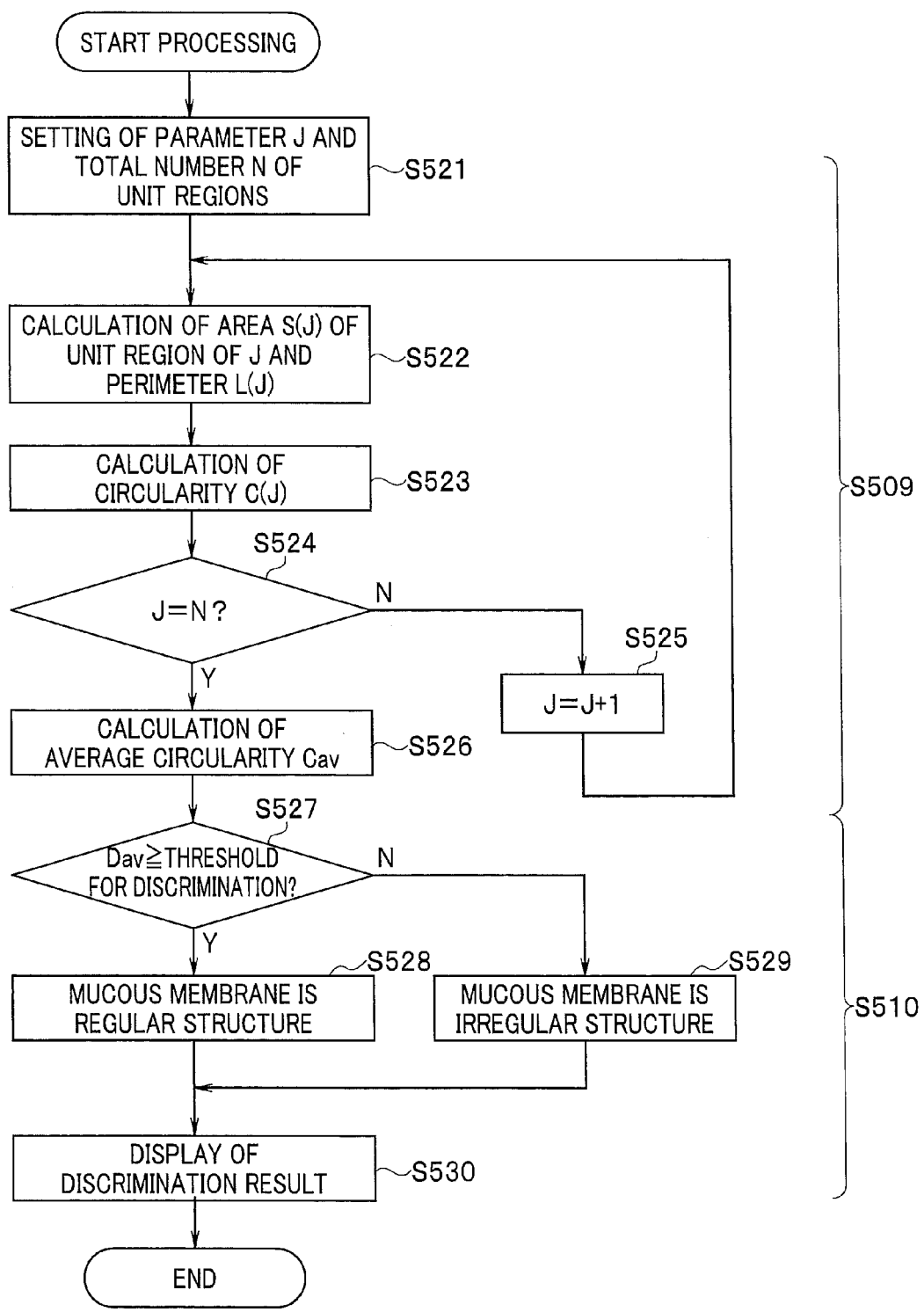
FIG. 42 is a flowchart showing detailed processing contents in steps S509 and S510 in FIG. 33A.

FIG. 42 shows details of processing of circularity calculation performed as the first feature value calculation in step S509 in FIG. 33A and processing of mucous membrane state discrimination in step S510 based on a processing result of the circularity calculation. Note that, in FIG. 42, the average circularity is calculated as a statistical amount of the first feature value. In step S510, discrimination of a mucous membrane state is performed according to a calculation result of the average circularity. However, the first feature value is not limited to the average circularity.

When the processing shown in FIG. 42 is started, as shown in step S521, (a circularity calculating section configuring) the first feature value calculating section 544a numbers (labels), with a number parameter J, the unit regions included in the determination target region Ad from the unit region of attention UBin and further sets a total number N of the unit regions included in the discrimination target region Ad.

In the next step S522, the circularity calculating section calculates, according to contour tracking of the unit region of the parameter J=1, a perimeter L(J) of a contour (of the unit region) and calculates an area S(J) in the contour.

In the next step S523, the circularity calculating section calculates circularity C(J) of the unit region of the parameter J. The circularity C(J) is represented as, for example, $C(J) = 4\pi S(J)/L(J)^2$. In the next step S524, the circularity calculating section determines whether the parameter J is equal to the total number N. When the parameter J is not equal to the total number N, after increasing J by 1 in step S525, the circularity calculating section returns to the processing in step S522.

When the calculation of circularities for all the unit regions included in the discrimination target region Ad ends in this way, in step S526, the circularity calculating section calculates average circularity Cav as a statistical amount of the first feature value.

The average circularity Cav is calculated by adding up circularities C from 1 to N of the parameter J and dividing the added-up circularity by the total number N. By calculating the average circularity Cav, the processing in step S509 in FIG. 33A ends and shifts to processing equivalent to step S510.

In step S527, the discriminating section 543h compares the average circularity Cav and the threshold for discrimination set by the threshold-for-discrimination setting section 547a and discriminates a mucous membrane state of the discrimination target region Ad according to whether the average circularity Cav is equal to or larger than the threshold for discrimination. When the average circularity is used as the first feature value, the threshold-for-discrimination setting section 547a sets the threshold for discrimination to, for example, about 0.6. When a determination result indicates that the average circularity Cav is equal to or larger than the threshold for discrimination in the determination processing in step S527, in step S528, the discriminating section 543h discriminates that the mucous membrane includes (is in a state including) a regular structure.

On the other hand, when a determination result indicates that the average circularity Cav is smaller than the threshold for discrimination, in step S529, the discriminating section 543h discriminates that the mucous membrane includes (is in a state including) an irregular structure. When it is discriminated that the mucous membrane includes the irregular structure, it is considered to be highly likely that a normal mucous membrane is in a state in which a shape of the normal mucous membrane is abnormal because of destruction of a structure.

On the other hand, when the average circularity Cav is equal to or larger than the threshold for discrimination, the normal mucous membrane is considered to be highly likely to be in a state in which the shape of the normal mucous membrane does not change from a structure of the normal membrane.

After steps S528 and S529, in step S530, the discriminating section 543h outputs the discrimination result to the video signal generating section 541c on the outside of the calculating section 541b, displays the discrimination result on the display device 505, and ends the processing shown in FIG. 42 or FIG. 33A.

The surgeon can obtain, from the state of the mucous membrane discriminated by the discriminating section 543h, information concerning whether the mucous membrane in the discrimination target region is highly likely to be a lesioned part. The surgeon can efficiently perform diagnosis by referring to the discrimination result by the discriminating section 543h.

Therefore, according to the present embodiment, it is possible to appropriately set a discrimination target region in a size with a unit region set as a unit and discriminate a state of a biological mucous membrane of the discrimination target region.

Note that, in the above explanation, the discrimination target region setting section 543g sets, as the discrimination target region Ad, the circular region Ac having a radius predetermined times (in a specific example, 1.5 times) as large as a maximum of a width of an external shape (a contour) of the unit region of attention UBin calculated as the second feature value of the unit region of attention UBin. The circular region Ac is not limitedly set as the discrimination target region Ad. For example, a rectangular region Ar indicated by a dotted line in FIG. 41B may be set as the discrimination target region Ad. Note that, in the rectangular region Ar shown in FIG. 41B, a length of one side is set to be three times as large as a maximum of a width of an external shape (a contour) of the unit region of attention UBin. However, the rectangular region Ar is not limited to this size.

As in the example explained with reference to FIG. 41B, the unit region setting section 543e may include a circular/rectangular region setting section 545c (indicated by a dotted line in FIG. 32) that sets, on the basis of the second feature value, the circular region Ac or the rectangular region Ar centering on the unit region of attention UBin. The unit region setting section 543e may set, as the discrimination target region Ad, (a group of) unit regions included in the circular region Ac or the rectangular region Ar set in the circular/rectangular region setting section 545c.

Figure 43A:
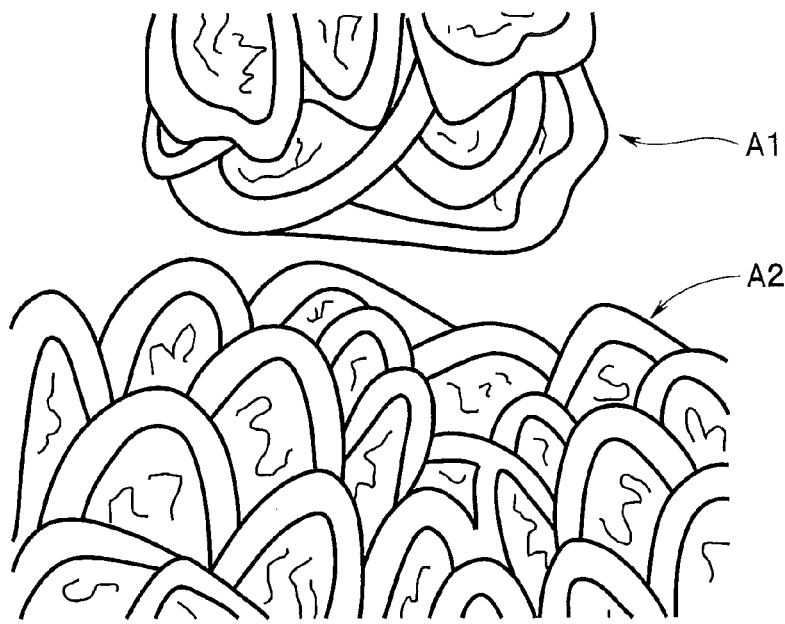
FIG. 43A is a diagram schematically showing an image example different from an image shown in FIG. 35 obtained by picking up an image of a biological mucous membrane inputted to the arithmetic section.
Figure 43B:
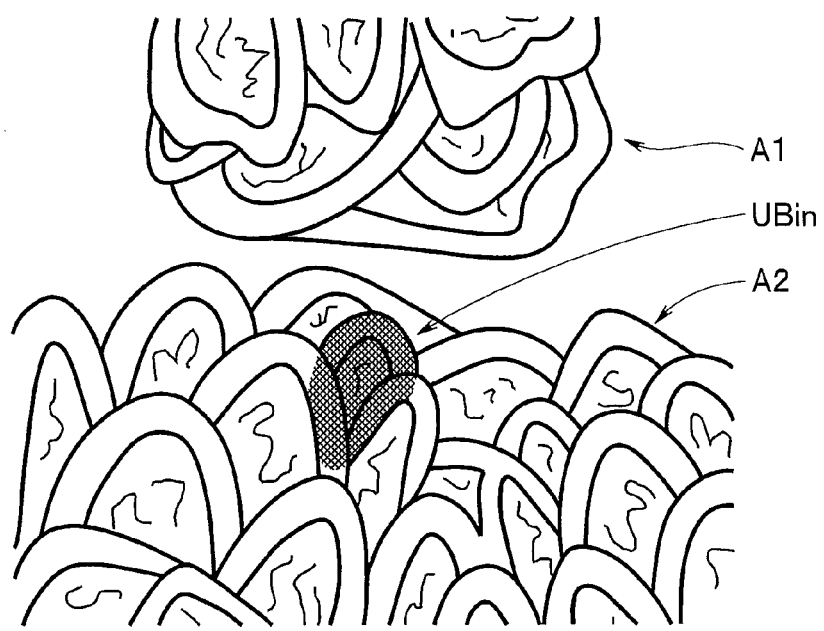
FIG. 43B is a diagram showing an example in which a unit region of attention set in a case of the image shown in FIG. 43A is set.
Figure 43C:
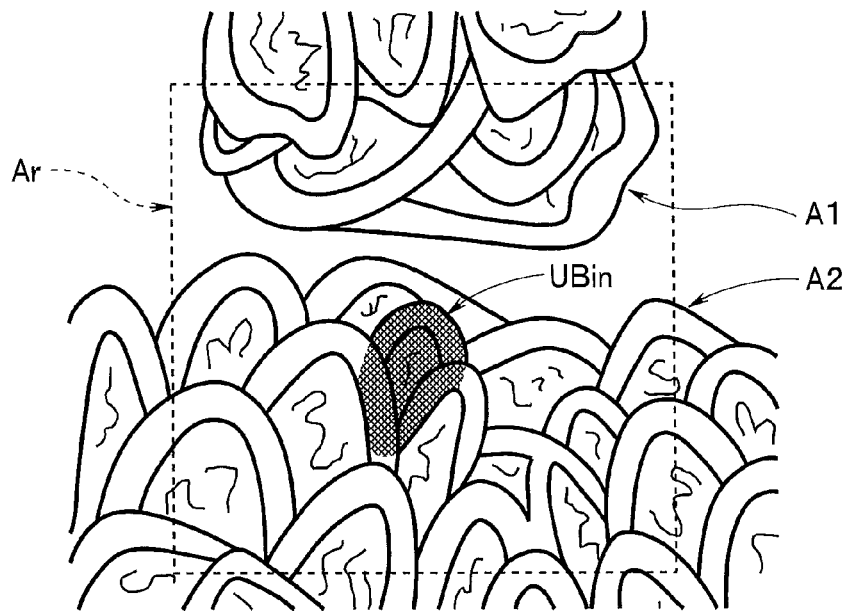
FIG. 43C is a diagram showing an example in which a rectangular region is further set in FIG. 43B.
Figure 43D:
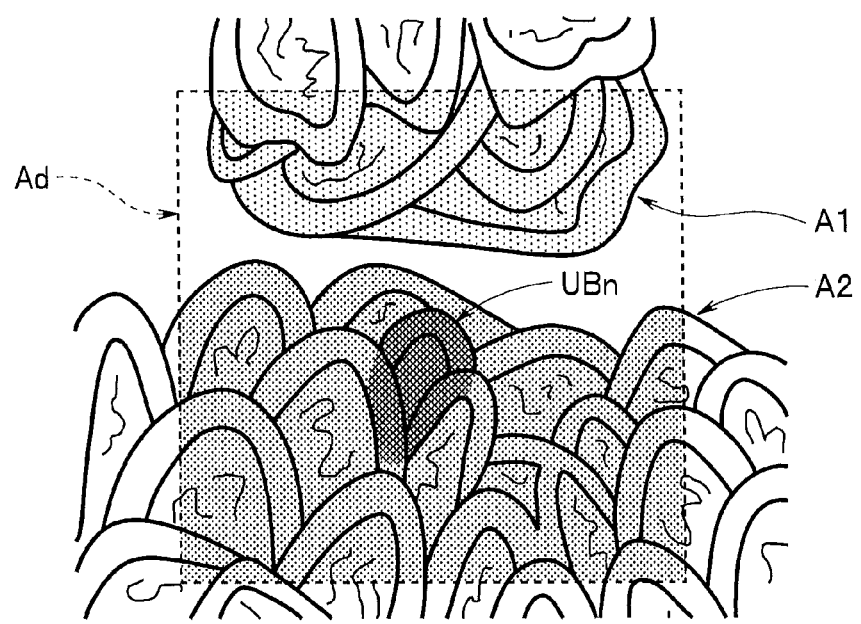
FIG. 43D is a diagram showing an example in which an inside of the rectangular region is set as a discrimination target region in FIG. 43C.

The setting method for the discrimination target region Ad explained above can be applied to an image in which unit regions are connected as shown in FIG. 41B and can be applied to an image having a structure in which a unit region group is separated into, for example, an upper region A1 and a lower region A2 as shown in FIG. 43A. In this case, as shown in FIG. 43B, for example, a unit region present at a closest distance to a center of an image can be set as the unit region of attention UBin, as shown in FIG. 43C, for example, the rectangular region Ar can be set with the unit region of attention UBin set in substantially a center as shown in FIG. 43C, and, as shown in FIG. 43D, the rectangular region Ar can be set as a discrimination target region Ad'. It is possible to discriminate a mucous membrane state of the discrimination target region Ad' on the basis of the first feature value on the basis of unit regions included in the discrimination target region Ad' shown in FIG. 43D.

However, in the structure in the case of the image shown in FIG. 41B, the respective unit regions are coupled or adjacent to unit regions adjacent thereto by an MCE serving as a common mucous membrane microstructure. On the other hand, in the structure in the case of the image shown in FIG. 43A, the unit regions are separated into the two regions A1 and A2 without being coupled or adjacent to the unit regions adjacent thereto by a belt-shaped MCE serving as the mucous membrane microstructure.

When the unit regions are separated into the two regions A1 and A2 as shown in FIG. 43A, a mucous membrane state is considered to be more appropriately discriminated when the discrimination target region is set excluding the region A1 side separated from the unit region of attention UBin.

Therefore, the discrimination target region may be set on the basis an order adjacent to the unit region of attention UBin as the third feature value that places more importance on a relation with the unit region of attention UBin. In this case, the order may be defined as explained below.

The unit region of attention UBin is set as a unit region of a zeroth order and, in a plurality of unit regions present around the unit region of attention UBin, for example, a unit region adjacent to the unit region of the zeroth order is set as a unit region of a first order, a unit region adjacent to the unit region of the first order and not adjacent to the unit region of the zeroth order is set as a unit region of a second order, and a unit region adjacent to the unit region of the second order and not adjacent to the unit region of the first order is set as a unit region of a third order. In other words, assuming that N is a natural number, a unit region adjacent to a unit region of an Nth order and not adjacent to a unit region of an N−1th order among the plurality of unit regions is set as a unit region of an N+1th order. A specific example is explained below.

The third feature value calculating section 544c calculates, as the third feature value, the order in the unit region of the zeroth order set as the unit region of attention UBin, the unit region of the first order adjacent to the unit region of the zeroth order, the unit region of the second order adjacent to the unit region of the first order, and the like. Concerning this order, the calculating section 541b includes a recognizing section 543j that recognizes, in the unit region of attention UBin and a plurality of unit regions present around the unit region of attention UBin, unit regions having a common mucous membrane microstructure as unit regions adjacent to one another (see FIG. 32). The third feature value calculating section 544c calculates, on the basis of a recognition result by the recognizing section 543j, orders adjacent to the unit region of attention UBin with respect to the plurality of unit regions present around the unit region of attention UBin. Therefore, the third feature value calculating section 544c includes a function of an order calculating section that calculates an order serving as the third feature value.

In the above explanation, the unit region of attention setting section 543i sets the unit region of attention UBin using the condition C1 (i.e., one unit region present at a closest distance to a center of an image). However, a condition for setting the unit region of attention UBin is not limited to the condition C1. The unit region of attention UBin may be set according to conditions C2 to C5 explained below on the basis of information concerning orders connected (coupled) to unit regions.

The unit region of attention setting section 543i may set the unit region of attention UBin according to the following conditions C2 to C5:

C2: a unit region in which an order of a unit region coupled thereto (U-1, U-2, etc. in the specification explained below) can be secured to a highest order,
C3: a unit region closest to a center (or a center of gravity) of an entire unit region group to be coupled,
C4: a unit region set at random in an image, and
C5: a unit region to be manually set.

Note that the unit region of attention UBin is not limited to one and a plurality of the unit regions of attention UBin may be set. Further, the unit region of attention UBin is not limited to one and the setting of the discrimination target region Ad and the discrimination of a mucous membrane state may be performed concerning all the unit regions. As order in performing the setting and the discrimination, the setting and the discrimination may be carried out in order from a unit region matching the conditions (C1 to C5), or may be carried out at random, or may be simply carried out in order from an upper right of the image.

In the above explanation, the first feature value calculating section 544a calculates average circularity as the first feature value. However, the first feature value is not limited to circularity. An area, a tone (a luminance value or a pixel value), a perimeter, and the like may be calculated from the unit regions included in the discrimination target region Ad. The first feature value calculating section 544a may calculate, as the first feature value, a statistical amount of dispersion (a fluctuation coefficient) besides the average statistical amount.

When the processing shown in FIG. 33A is performed, in step S507, the second feature value calculating section 544b calculates an area of the unit region of attention UBin as the second feature value (not as the width) as explained below. In step S508, the discrimination target region setting section 543g may set, on the basis of the calculated area, a discrimination target region using an order on the basis of a comparison result obtained by using a threshold of the area.

The discrimination target region setting section 543g sets a range of the discrimination target region Ad according to whether the area of the unit region of attention UBin calculated as the second feature value is equal to or larger than a threshold (more specifically, a threshold of an area). In this way, the discrimination target region setting section 543g sets, on the basis of the calculated second feature value, (the range of) the discrimination target region Ad with the unit region set as a unit. That is, the discrimination target region setting section 543g sets, on the basis of the calculated second feature value, the discrimination target region Ad as a unit region group including the unit region of attention UBin.

When setting the discrimination target region Ad, the discrimination target region setting section 543g may set (determine) the discrimination target region Ad on the basis of the third feature value representing a structural relation between the unit region of attention UBin and the unit region UBj around the unit region of attention UBin as explained below.

Figure 44:
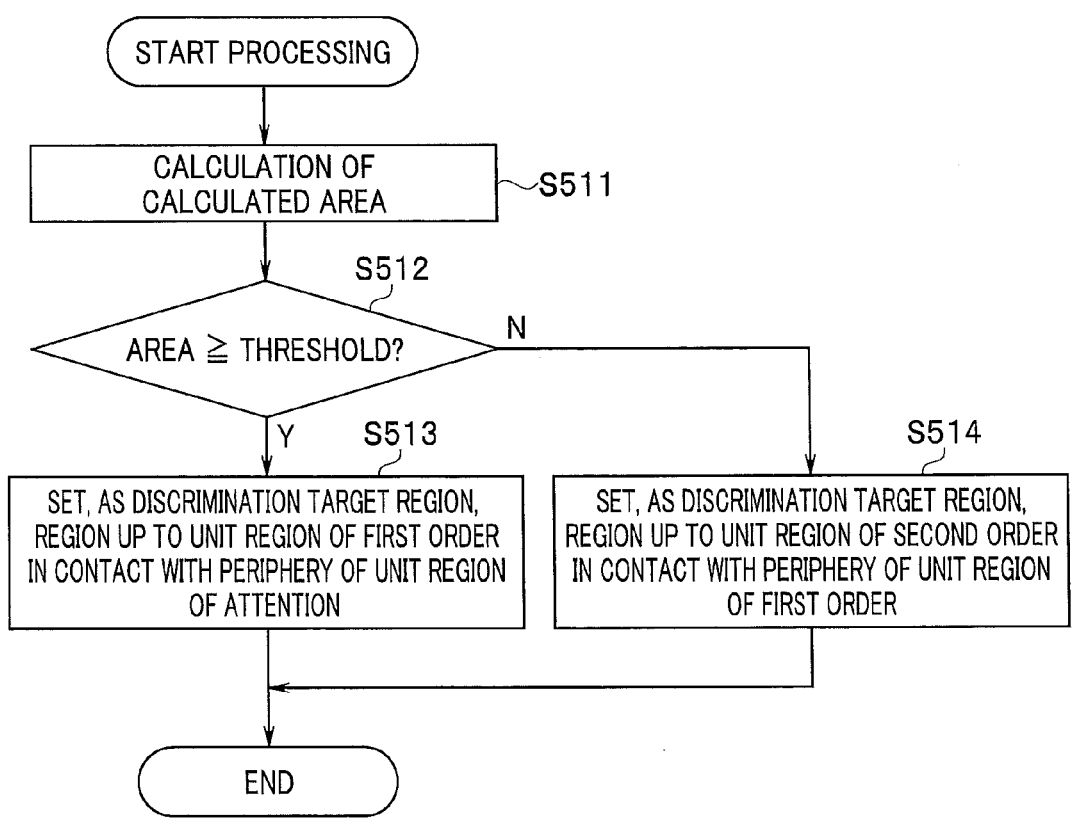
FIG. 44 is a flowchart showing processing content for setting a discrimination target region on the basis of a second feature value calculated with respect to the unit region of attention.

FIG. 44 shows a processing in which the discrimination target region setting section 543g sets (determines) the discrimination target region Ad on the basis of the area serving as the third feature value.

As shown in step S511, the area calculated by the second feature value calculating section 544b is inputted to the discrimination target region setting section 543g. As shown in step S512, the discrimination target region setting section 543g determines whether the area calculated by the second feature value calculating section 544b is equal to or larger than the threshold of an area set by the threshold setting section 546a. Note that the threshold setting section 546a sets the threshold of an area to, for example, about 5000, more specifically, the number of pixels of 5000.

When a determination result indicating that the area is equal to or larger than the threshold of an area is obtained in the determination processing in step S512, as shown in step S513, the discrimination target region setting section 543g sets, as the discrimination target region Ad, the unit region of attention UBin to the unit region UBj directly in contact with a periphery of the unit region of attention UBin. In other words, the discrimination target region setting section 543g sets, as the discrimination target region Ad, a region (of a unit region or a unit region group) from a unit region of a zeroth order, in which the unit region of attention UBin is set as the unit region of the zeroth order, to a unit region of a first order in direct contact with the unit region of the zeroth order.

Figure 45A:
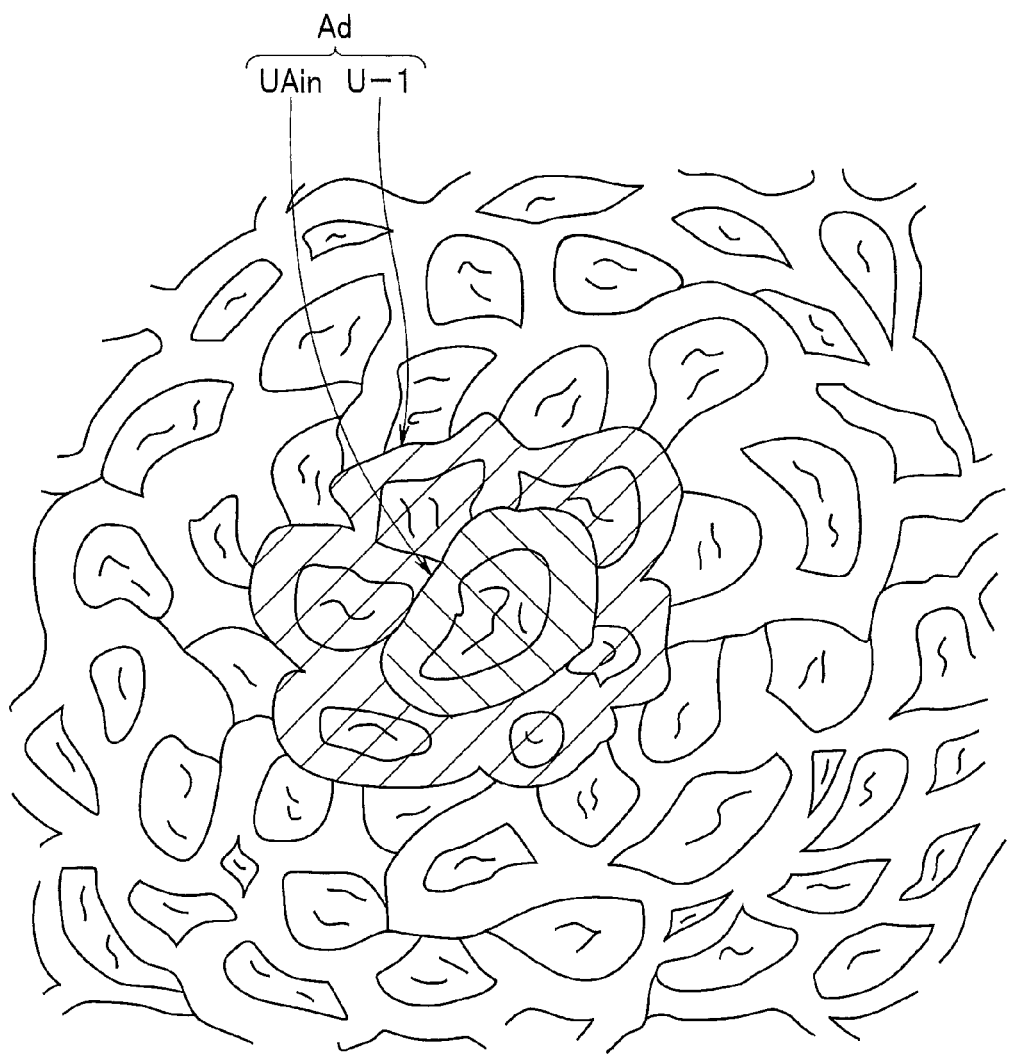
FIG. 45A is a diagram showing a discrimination target region set in a case in which an area is equal to or larger than a threshold in the processing in FIG. 44.
Figure 45B:
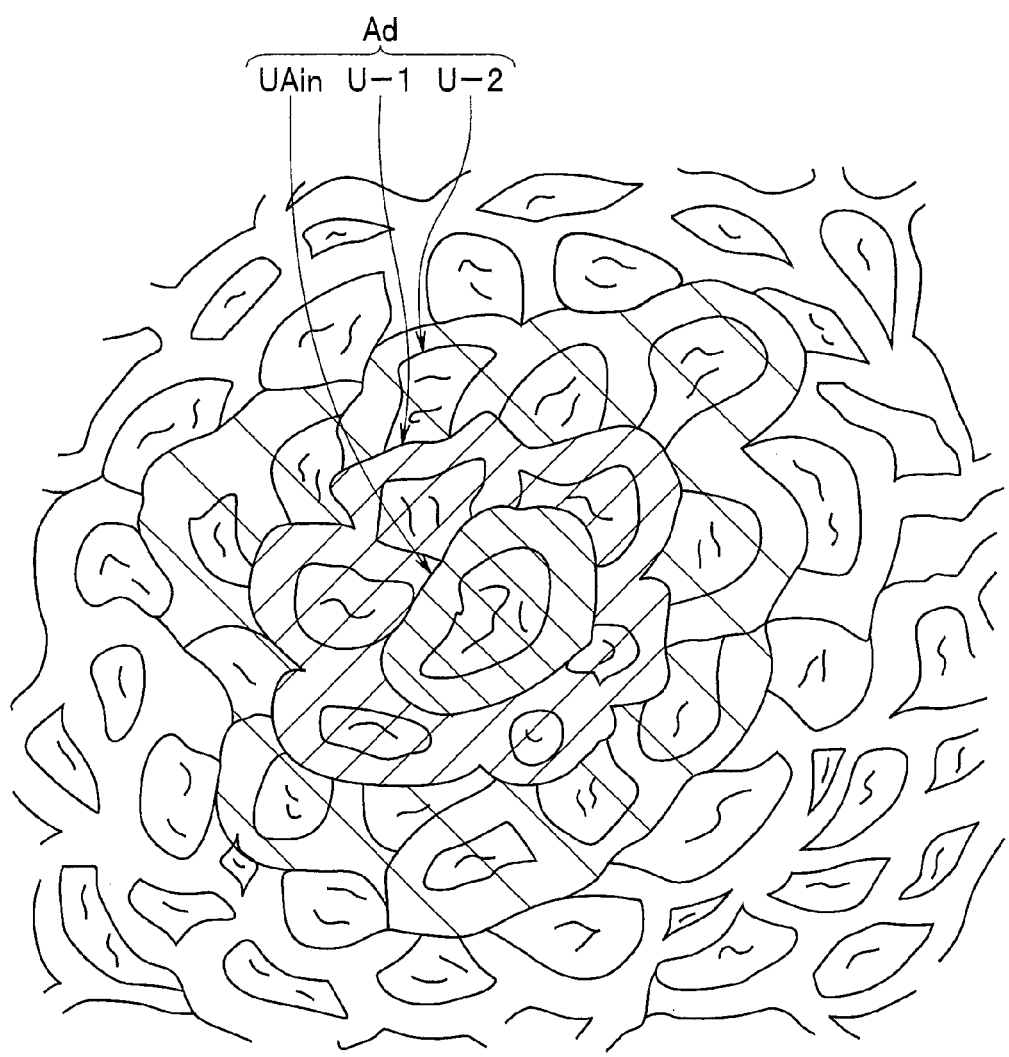
FIG. 45B is a diagram showing a discrimination target region set in a case in which an area is smaller than the threshold in the processing in FIG. 44.

For example, when the area of the unit region of attention UBin shown in FIG. 41A is equal to or larger than the threshold of an area, as shown in FIG. 45A, the discrimination target region setting section 543g sets, as the discrimination target region Ad, the unit region of attention UBin to a unit region (group) U-1 of a first order indicated by hatching around the unit region of attention UBin. On the other hand, when the area of the unit region of attention UBin is smaller than the threshold of an area in the determination in step S512 in FIG. 44, as shown in step S514, the discrimination target region setting section 543g sets, as the discrimination target region Ad, the unit region of attention UBin to the unit region (group) U-1 of the first order directly in contact with the unit region of attention UBin and a unit region (group) U-2 of a second order directly in contact with the unit region (group) U-1 of the first order. In other words, the discrimination target region setting section 543g sets, as the discrimination target region Ad, a region (of a unit region group) from a unit region of a zeroth order to a unit region of a first order and a unit region of a second order. In this case, the discrimination target region Ad is set as shown in FIG. 45B. The discrimination target region setting section 543g ends the setting processing for the discrimination target region as shown in FIG. 44, that is, ends the processing in step S508 in FIG. 33A.

In this way, when, for example, the area value serving as the second feature value is smaller than the threshold, a range of unit regions included in the discrimination target region Ad is expanded to be larger than a range set when the area value is equal to or larger than the threshold. Consequently, it is possible to appropriately perform discrimination without insufficiency of information used to discriminate a state of a mucous membrane from the discrimination target region Ad.

After setting (determining) the discrimination target region Ad, the discrimination target region setting section 543g outputs information concerning the setting (the determination) to the first feature value calculating section 544a of the feature value calculating section 543f. As explained above, the processing in step S509 and subsequent steps in FIG. 33A is performed as explained above.

Figure 46:
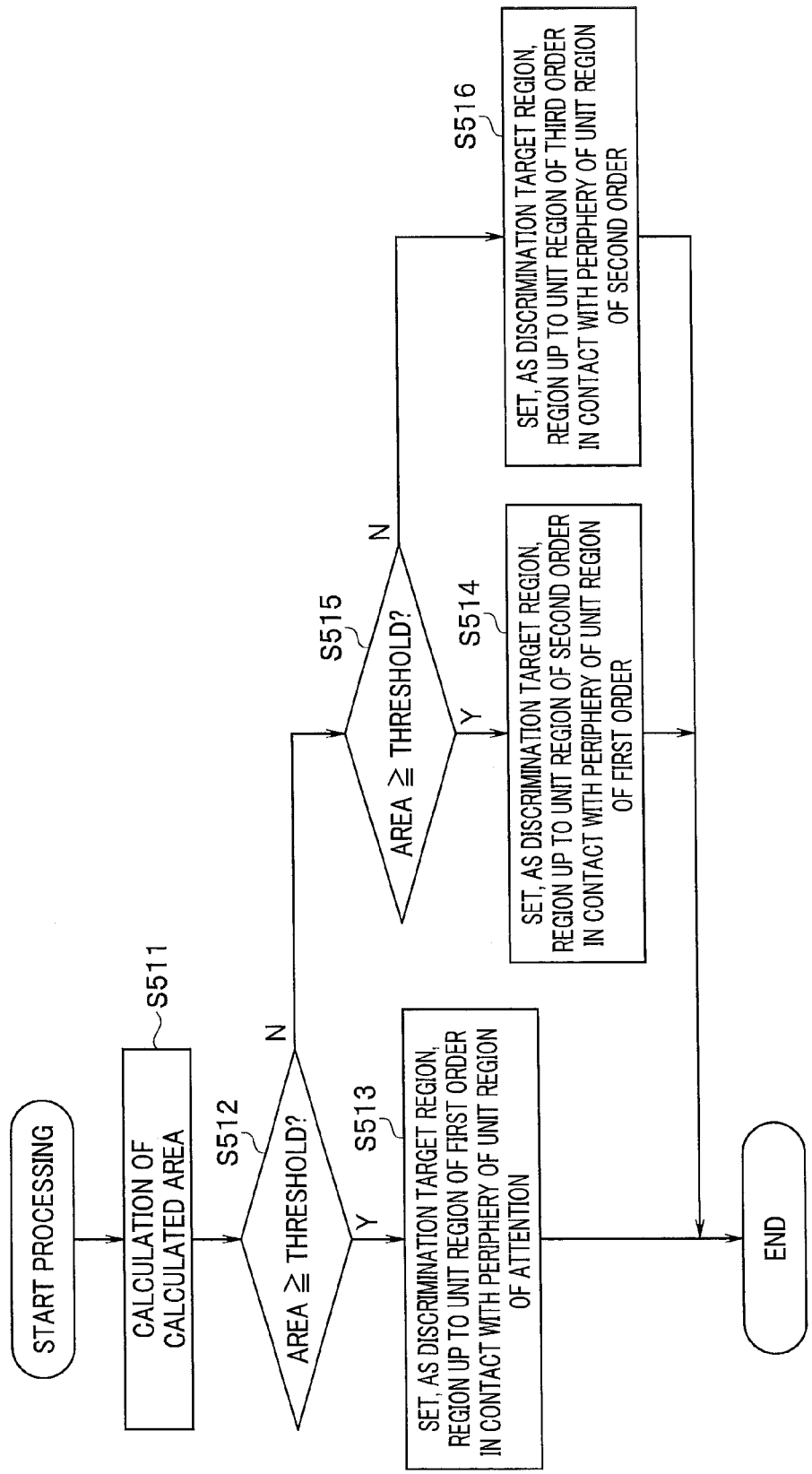
FIG. 46 is a flowchart showing processing content for setting a discrimination target region using two thresholds on the basis of the second feature value calculated with respect to the unit region of attention.

Note that the setting of the discrimination target region Ad is not limited to setting the discrimination target region Ad to the unit region (group) U-1 of the first order or the unit region (group) U-2 of the second order according to an area of the unit region of attention UBin as shown in FIG. 44. A unit region (group) U-3 of a third order may be set to be used. For example, when the area of the unit region of attention UBin is smaller than the threshold (more specifically, 5000) in the determination in step S512 in FIG. 44, the discrimination target region setting section 543g may further determine whether the area of the unit region of attention UBin is equal to or larger than a second threshold (e.g., 3000) (a value smaller than the threshold) as shown in step S515 in FIG. 46.

When the area value of the unit region of attention UBin is equal to or larger than the second threshold, the discrimination target region setting section 543g includes, in the discrimination target region Ad, unit regions up to the unit region (group) U-2 as shown in step S514 in FIG. 42.

On the other hand, when the value of the area of the unit region of attention UBin is smaller than the second threshold, the discrimination target region setting section 543g may include, in the discrimination target region Ad, unit regions up to the unit region (group) U-3 of the third order in contact with a periphery of the unit region (group) U-2 of the second order as shown in step S516. In this way, it is also possible to set the two stages of thresholds and set, according to a result of comparison with the thresholds, an order of a unit region (group) included in the discrimination target region Ad. It is also possible to set three or more stages of thresholds and set, according to a result of comparison with the thresholds, an order of a unit region (group) included in the discrimination target region Ad.

Alternatively, it is also possible to set, according to, for example, arithmetic processing indicated by Expression (2) below, an order (this order is defined as a connection order) N of a unit region (group) included in the discrimination target region Ad.

$$\text{Connection order } N=10000/(\text{area of unit region of attention } UB\text{in}) \quad (2)$$

A fraction after a decimal point in a calculation result of Expression (2) is omitted. When a calculation result is smaller than 1 (i.e., an area of the unit region of attention UBin exceeds 10000), N is set to 1.

Next, discrimination target region setting means and discrimination target region setting method using an order effective for range setting for a discrimination target region in the case of the image shown in FIG. 43A are explained below. After performing setting of a unit region shown in step S541 in FIG. 47 on the image shown in FIG. 43A, processing for setting of a unit region of attention is performed as shown in step S542.

In this case, the recognizing section 543j recognizes that unit regions including a common mucous membrane microstructure are unit regions (or unit region groups) adjacent to each other. The third feature value calculating section 544c calculates, as the third feature value, an order of a unit region adjacent to the unit region of attention UBin on the basis of a recognition result by the recognizing section 543j.

As explained above, in the image shown in FIG. 43A, for example, as shown in FIG. 43B, the unit region of attention UBin is set as, for example, a unit region present at a distance closest to a center of the image. Note that, as explained above, the unit region of attention UBin may be set to meet, for example, the condition of C2 or C3 other than the condition of C1 as explained above.

Figure 47:
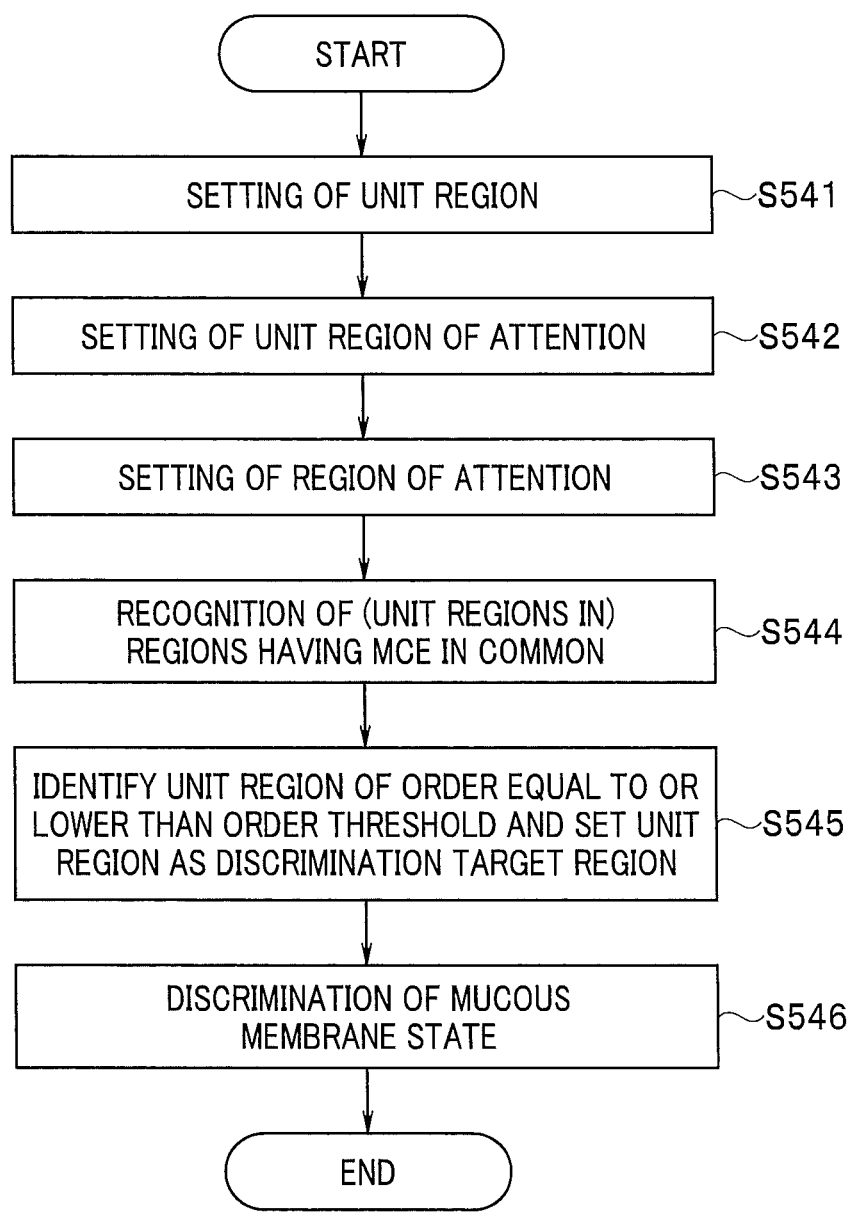
FIG. 47 is a flowchart showing processing content in a case in which a discrimination target region is set for the image shown in FIG. 43A using an order as a third feature value.

As shown in step S543 in FIG. 47, the second feature value calculating section 544b performs calculation of second feature values such as an area and a width of the unit region of attention UBin. As shown in step S544, the discrimination target region setting section 543g identifies, on the basis of a calculation result of the second feature values, a unit region of an order equal to or smaller than a threshold of an order and sets the unit region as the discrimination target region Ad. For example, when setting the discrimination target region Ad according to the processing shown in FIG. 44, the discrimination target region setting section 543g sets a unit region of an order equal to or smaller than 2 as the discrimination target region Ad when an area of the unit region of attraction UBin is equal to or smaller than a threshold.

Figure 48:
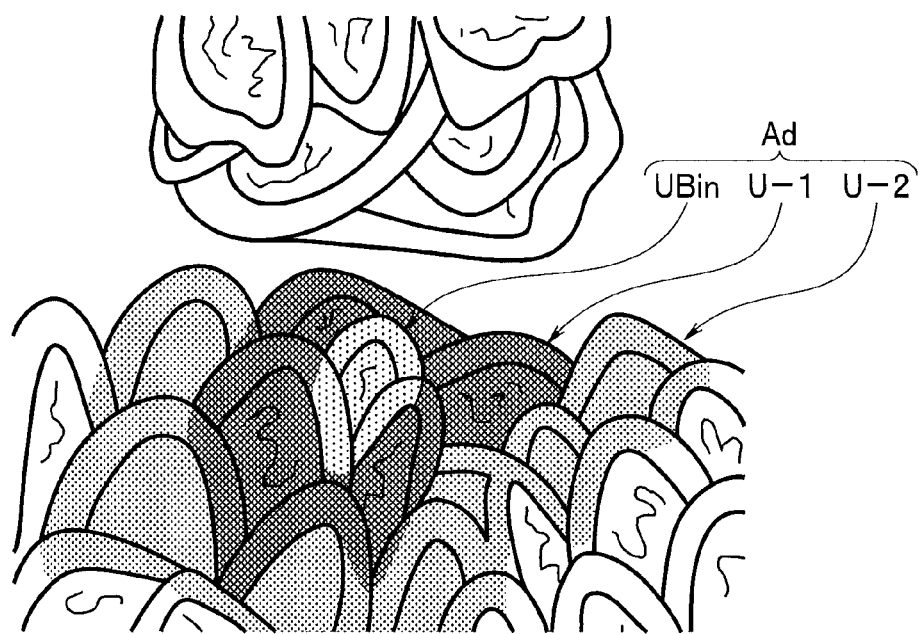
FIG. 48 is a diagram showing an example of a discrimination target region set in the processing in FIG. 47.
Figure 49:
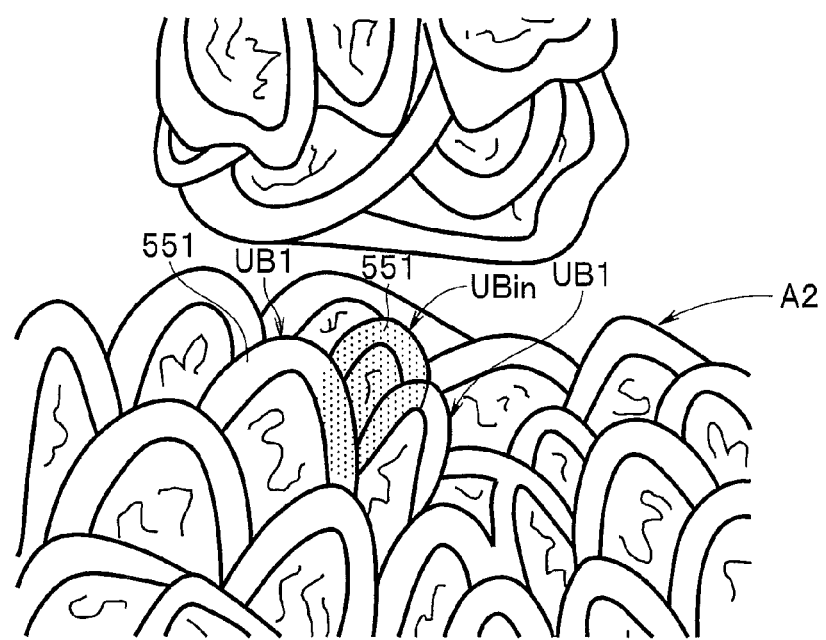
FIG. 49 is an explanatory diagram for explaining that the number of unit regions in contact with a common MEC is recognized by a recognizing section.

FIG. 48 shows an example of the discrimination target region Ad set when the area of the unit region of attention UBin is equal to or smaller than the threshold with respect to the image shown in FIG. 43A. In this case, the unit region of attention UBin is set as a unit region of a zeroth order. The discrimination target region Ad is set by the unit region (group) U-1 of the first order including four unit regions in contact with an outer side of the unit region of attention UBin via the common MCE 551 and the unit region (group) U-2 of the second order including seven unit regions in contact with an outer side of the unit region (group) U-1 of the first order via a common MCE. Note that, FIG. 49 shows an explanatory diagram for explaining that the unit regions around the unit region of attention UBin are in contact via the common MCE 551. As shown in FIG. 49, in the unit region of attention UBin, a lower portion of the belt-shaped MCE 551 forming the unit region of attention UBin is common to the MCE 551 of the unit regions UB1 and UB2. The other unit regions are also in contact via the common MCE 551. The recognizing section 543j recognizes that unit regions having the MCE 551 serving as a common mucous membrane microstructure among a plurality of unit regions around the unit region of attention UBin are unit regions adjacent to each other.

When the discrimination target region Ad is set using the order with respect to the unit region of attention UBin in this way, it is possible to set a region having a high relation with the unit region of attention UBin as the discrimination target region Ad. As shown in FIG. 47, in the next step S545 of step S544, the discriminating section 543h performs discrimination of a mucous membrane state using a calculation result of a first feature value by the first feature value calculating section 544a with respect to the discrimination target region Ad. Further, in the next step S546, the discriminating section 543h outputs a discrimination result to the video signal generating section 541c. The discrimination result is displayed on the display device 505. The processing shown in FIG. 47 ends.

When the discrimination target region Ad is set using the order as shown in FIG. 47, not only when the unit regions are coupled as shown in FIG. 41B but also in the case of the image in which the unit regions are not coupled like the regions A1 and A2 as shown in FIG. 43A, the discrimination target region Ad can be set to include a unit region having a high relation with the unit region of attention UBin. Therefore, it is possible to perform highly accurate discrimination of a mucous membrane state.

Note that, in FIG. 42, the discrimination is performed using the average circularity Cav and the threshold for discrimination. However, it is also possible to calculate a fluctuation coefficient CV of circularity, an area, or a perimeter and discriminate that a structure has an irregular mucous membrane state when the fluctuation coefficient CV is equal to or larger than a threshold (e.g., 0.3) of a fluctuation coefficient and that a structure has a regular mucous membrane state when the fluctuation coefficient CV is smaller than the threshold.

It is also possible to compare circularity, an area, or a perimeter of the unit region of attention UBin and an average in the discrimination target region Ad and discriminate that a structure has an irregular mucous membrane state when a ratio of the former and the latter is equal to or larger than a threshold of 1.3 and that a structure has a regular mucous membrane state when the ratio is smaller than the threshold.

In the above explanation, the various feature values are calculated in the entire respective unit regions included in the discrimination target region Ad. However, the various feature values may be calculated from each of blood vessels, MCEs, and interval portions included in the respective unit regions. A mucous membrane state may be discriminated using a threshold corresponding to each of the blood vessels, the MCEs, and the interval portions.

In the above explanation for setting (calculating) a unit region, when the width Tk of the MCE region MBi is calculated, the width Tk is calculated using the boundary pixel BQk of the substantially closed region CBj. However, the width Tk may be calculated from the MCE region MBi. In other words, the feature value calculating section like the width calculating section 545a may calculate a feature value used in the range setting for a unit region from the MCE region MBi serving as the mucous membrane microstructure region or may calculate a feature value used for the range setting for a unit region from the substantially closed region CBj serving as the closed region.

Note that the content of the preprocessing in step S502 in FIG. 33A is not limited to the noise suppression and the inverse gamma correction. For example, correction of brightness and a tone may be added. Concerning the respective methods of the preprocessing, the methods are not limited. The methods may be changed according to a target image and characteristics of an apparatus. For example, in the present embodiment, the median filtering is used as the method for noise suppression. However, other methods such as a smooth filter may be used.

The detecting or extracting method for the MCE region MBi in step S503 is not limited to the structural component extraction method. Other methods may be used. For example, the detecting or extracting method may be threshold processing for a luminance value or a pixel value such as a tone, a method using various frequency filters such as a Gabor filter, or linear detection processing using a Hessian matrix or a vector concentration degree, which is a publicly-known technique.

The detecting or identifying method for the substantially closed region CBj in step S504 is not limited to the method using the labeling. Other methods may be used. For example, a closed region may be searched to detect the substantially closed region CBj by scanning the boundary pixel BQk of the detected MCE region MBi.

In step S505, the width Tk is calculated by counting the number of pixels from the boundary pixel BQk. However, the calculation of the width Tk is not limited to this method. Other methods such as a method of using, as the width Tk, a size of a template or a filter used in the extraction of the MCE region MBi in step S503 may be used.

The calculation of the width Tk is carried out in all the boundary pixels BQk. However, the calculation of the width Tk is not limited to the use of all the boundary pixels BQk. For example, the width Tk may be calculated from pixels sampled at every several pixels.

Further, the calculation of the region size BSj is not limited to the average of the width Tk. Other statistical amounts such as a mode, a minimum, and a maximum of the width Tk may be used.

The calculation of the region size BSj is not limited to a method using the width Tk. The region size BSj may be calculated from a size, a shape, and the like of the substantially closed region CBj or the user may set any value. The region size BSj for specifying a range of a unit region may be determined from, for example, an area of the substantially closed region CBj.

Further, in the present embodiment, the range of the unit region UBj is set as the distance from the boundary pixel of the substantially closed region CBj. However, the setting of the range of the unit region UBj is not limited to this method. The range of the unit region UBj may be set with reference to, for example, a center point (a center of gravity) of the substantially closed region CBj.

In FIG. 40, the example is shown in which the respective unit regions UBj are allowed to overlap. However, it is also possible to determine which of the unit regions UBj overlapping portions belong to and divide overlapping regions.

An image may be displayed on the display device 505 or the like by retaining respective pixels, which are set as the unit region UBj, as image data and generating a video signal with the video signal generating section 541c.

According to the present embodiment, in a medical image representing a mucous membrane microstructure, a region set as one unit in terms of the biological histology is set to be separable or identifiable as a unit region. It is possible to, with the unit region set as a unit, set a discrimination target region including a unit region group of an appropriate size around the unit region of attention UBin to include the unit region of attention UBin and discriminate a mucous membrane state of the discrimination target region.

Therefore, even in complicated image data, it is possible to set a discrimination target region to be diagnosed to an appropriate size with a biologically histological unit region set as a unit. It is possible to appropriately discriminate a mucous membrane state of the discrimination target region and support diagnosis and the like.

On the other hand, in the case of the conventional example in which a biologically histological unit region cannot be set, it is necessary to perform diagnosis for a complicated range extending over a plurality of units in terms of the biological histology. It is difficult to perform state discrimination.

Note that, in the third embodiment, it is also possible to set the unit region of attention UBin as the discrimination target region Ad, (set) the unit region of attention UBin alone (as the discrimination target region Ad and) perform calculation of the first feature value, and perform discrimination of a mucous membrane state of the unit region of attention UBin on the basis of the calculated first feature value. More specifically, for example, the unit region of attention UBin set in FIG. 41A is set as the discrimination target region Ad. The unit region of attention UBin shown in FIG. 43B may be set as the discrimination target region Ad.

Figure 50:
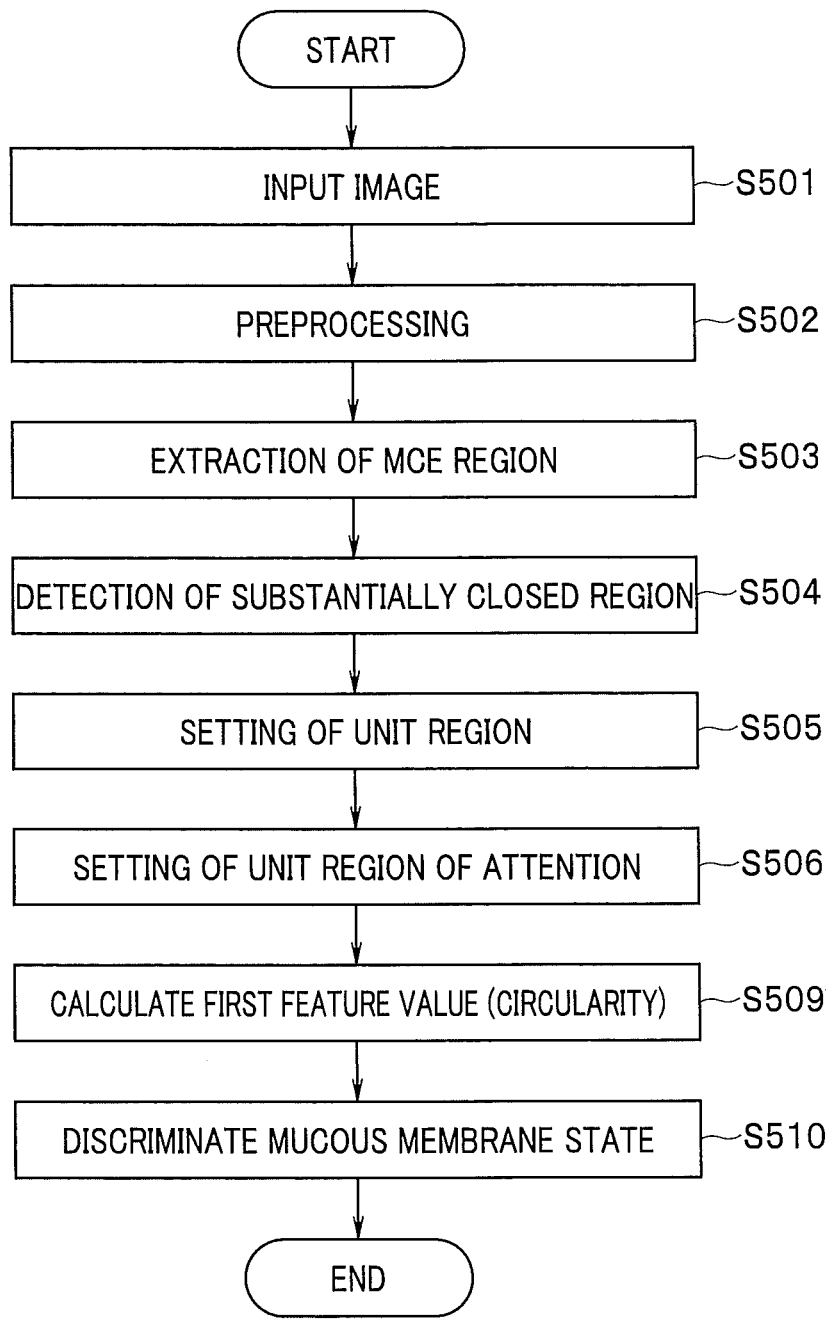
FIG. 50 is a flowchart showing processing content in a modification of the third embodiment.

FIG. 50 shows processing in this case. The processing in steps S501 to S506 shown in FIG. 50 is the same as the contents explained with reference to FIG. 33A. After the processing in step S506, S507 and S508 in FIG. 33A are not performed and processing in steps S509 and S510 is performed.

Note that, in FIG. 33A, the calculation of the first feature value is performed for the discrimination target region Ad including the plurality of unit regions including the unit region of attention UBin. However, in step S509 shown in FIG. 50, the first feature value calculating section 544a performs the calculation of the first feature value for the unit region of attention UBin. For example, the first feature value calculating section 544a calculates circularity as the first feature value of the unit region of attention UBin. In step S510, the discriminating section 543h determines that a mucous membrane of the unit region of attention UBin has a regular structure when the calculated circularity is equal to or larger than, for example, a threshold of 0.6 and that the mucous membrane has an irregular structure when the circularity is smaller than 0.6. Alternatively, the discriminating section 543h may determine that the mucous membrane of the unit region of attention UBin has a regular structure when a fluctuation coefficient of thickness (width) of an MCE included in the unit region of attention UBin is smaller than 0.3 and that the mucous membrane has an irregular structure when the fluctuation coefficient is equal to or larger than 0.3.

Note that, in the embodiments and the like explained above, as an example of discrimination of a mucous membrane state, discrimination of a category representing whether a mucous membrane has a regular structure or an irregular structure and representing a "state" of the mucous membrane state is explained. However, the discrimination of the mucous membrane state is not limited to the discrimination of the category. It is also possible to compare a calculation result of a statistical value of the first feature value with a threshold and perform discrimination of a category concerning a "condition of a disease" or "medical classification" for discriminating a disease is cancer or not cancer. In the embodiments, the discrimination of the mucous membrane state is explained in the case of the stomach. However, the embodiments can also be applied to medical images obtained by picking up images of biological mucous membranes of a large intestine, an esophagus, and the like.

Note that the discriminating section 543h may be configured to include the first feature value calculating section 544a that calculates the first feature value. The discriminating section 543h may be configured to include a statistical amount calculating section 547b that calculates a statistical amount of the first feature value as indicated by a dotted line in FIG. 32. The discriminating section 543h may discriminate a mucous membrane state on the basis of the statistical amount. Embodiments configured by partially combining the embodiments and the like also belong to the present invention.

Note that the present invention is not limited to the embodiments explained above. It goes without saying that various alterations and applications are possible within a range not departing from the spirit of the invention.

What is claimed is:

1. A medical image processing device comprising:
a processor comprising hardware, the processor being configured to implement:
an input section to which a biological mucous membrane image obtained by picking up an image of a biological mucous membrane is inputted;
a region extracting section configured to extract a mucous membrane microstructure region corresponding to a mucous membrane microstructure, which is a microscopic structure included in the biological mucous membrane, from the biological mucous membrane image inputted to the input section;
an imaginary mucous membrane microstructure setting section configured to set an imaginary mucous membrane microstructure region on the biological mucous membrane image;
a closed region identifying section configured to identify at least one closed region regarded as being surrounded by the mucous membrane microstructure region extracted by the region extracting section and the imaginary mucous membrane microstructure region set by the imaginary mucous membrane microstructure setting section; and
a unit region setting section configured to set a unit region, which is a region set as one unit in terms of biological histology, on the basis of the mucous membrane microstructure region extracted by the region extracting section and the closed region identified by the closed region identifying section.

2. The medical image processing device according to claim 1, wherein the region extracting section extracts a belt-shaped structure region in the biological mucous membrane image as the mucous membrane microstructure region.

3. The medical image processing device according to claim 1, wherein, when the unit region setting section performs the setting of the unit region for a plurality of the closed regions, the unit region setting section performs the setting of the unit region independently for each of the plurality of closed regions.

4. The medical image processing device according to claim 1, wherein the processor is further configured to implement:
a feature value calculating section configured to calculate a feature value used for range setting for the unit region from the mucous membrane microstructure region or the closed region; and
a range setting section configured to set a range of the unit region on the basis of the feature value.

5. The medical image processing device according to claim 1, wherein the mucous membrane microstructure is an epithelium pattern or a pit pattern based on a blood vessel and a gland structure on the biological mucous membrane.

6. The medical image processing device according to claim 1, wherein the imaginary mucous membrane microstructure setting section connects unclosed end points in the mucous membrane microstructure region extracted by the region extracting section and sets the imaginary mucous membrane microstructure region.

7. The medical image processing device according to claim 1, wherein the imaginary mucous membrane microstructure setting section sets the imaginary mucous membrane microstructure region using an imaginary line extending in an extending direction of the mucous membrane microstructure region from an unclosed end point in the mucous membrane microstructure region extracted by the region extracting section.

8. The medical image processing device according to claim 4, wherein the feature value calculating section is configured by a width calculating section that calculates a size of a width of the mucous membrane microstructure region surrounding the closed region.

9. A medical image processing device comprising:
a processor comprising hardware, the processor being configured to implement:
an input section to which a biological mucous membrane image obtained by picking up an image of a biological mucous membrane is inputted;
a region extracting section configured to extract a mucous membrane microstructure region corresponding to a mucous membrane microstructure, which is a microscopic structure included in the biological mucous membrane, from the biological mucous membrane image inputted to the input section;
a closed region identifying section configured to identify at least one closed region regarded as being surrounded by the mucous membrane microstructure region extracted by the region extracting section; and
a unit region setting section configured to set, when the biological mucous membrane is an epithelium pattern, a region of an interval portion serving as the closed region and a region of a crypt side edge epithelium adjacent to an outer side of a peripheral edge of the region of the interval portion and forming the mucous membrane microstructure having a closed belt shape and surrounding the interval portion.

10. A medical image processing device comprising:
a processor comprising hardware, the processor being configured to implement:
an input section to which a biological mucous membrane image obtained by picking up an image of a biological mucous membrane in inputted;
a region extracting section configured to extract a mucous membrane microstructure region corresponding to a mucous membrane microstructure, which is a microscopic structure included in the biological mucous membrane, from the biological mucous membrane image inputted to the input section;
a closed region identifying section configured to identify at least one closed region regarded as being surrounded by the mucous membrane microstructure region extracted by the region extracting section;
a unit region setting section configured to set a unit region, which is a region set as one unit in terms of biological histology, on the basis of the mucous membrane microstructure region extracted by the region extracting section and the closed region identified by the closed region identifying section;
a first feature value calculating section configured to calculate a first feature value from a discrimination target region set on the basis of the unit region set in the unit region setting section;
a discriminating section configured to discriminate, on the basis of the first feature value calculated by the first feature value calculating section, a state of a mucous membrane including the discrimination target region;
a unit region of attention setting section that, when a plurality of the unit regions are set in the unit region setting section, is configured to set, from the plurality of unit regions set in the unit region setting section, a unit region of attention serving as one unit region to be paid attention to;
a second feature value calculating section configured to calculate a second feature value from the unit region of attention; and
a discrimination target region setting section configured to set, on the basis of the second feature value, from the plurality of unit regions, the discrimination target region for which the calculation of the first feature value is performed, wherein
the first feature value calculating section performs the calculation of the first feature value in the discrimination target region set in the discrimination target region setting section.

11. The medical image processing device according to claim 10, wherein the processor is further configured to implement a third feature value calculating section configured to calculate a third feature value representing a relation with the unit region of attention with respect to the plurality of unit regions, wherein
the discrimination target region setting section includes a threshold setting section that sets a threshold used in setting the discrimination target region on the basis of the second feature value, and
sets the discrimination target region from the plurality of unit regions on the basis of the threshold and the third feature value.

12. The medical image processing device according to claim 11, wherein
the third feature value calculating section calculates, as the third feature value, an order with respect to the plurality of unit regions adjacent to the unit region of attention, and
the discrimination target region setting section sets, as the discrimination target region, the plurality of unit regions having an order equal to or smaller than the threshold.

13. The medical image processing device according to claim 11, wherein
the third feature value calculating section calculates, as the third feature value, a distance from the unit region of attention with respect to the plurality of unit regions, and
the discrimination target region setting section sets, as the discrimination target region, the plurality of unit regions whose distance from the unit region of attention is equal to or smaller than the threshold.

14. The medical image processing device according to claim 10, wherein
the unit region setting section includes a rectangular region setting section that sets, on the basis of the second feature value, a size of a rectangular region centering on the unit region of attention, and
the unit region setting section sets, as the discrimination target region, the plurality of unit regions included in the rectangular region set in the rectangular region setting section.

15. The medical image processing device according to claim 12, wherein the third feature value calculating section calculates, as the third feature value, an order of the plurality of unit regions calculated by setting the unit region of attention as a unit region of a zeroth order, recognizing, as a unit region of a first order, a unit region adjacent to the unit region of the zeroth order among the plurality of unit regions, and setting, as a unit region of an N+1th order, a unit region adjacent to a unit region of an Nth order and not adjacent to a unit region of an N-1th order among the plurality of unit regions, where N is a natural number.

16. The medical image processing device according to claim 12, wherein the processor is further configured to implement a recognizing section configured to recognize that unit regions including a common mucous membrane microstructure among the plurality of unit regions are unit regions adjacent to each other, wherein
    the third feature value calculating section calculates an order adjacent to the unit region of attention with respect to the plurality of unit regions on the basis of a recognition result by the recognizing section.

17. The medical image processing device according to claim 10, wherein
    the discriminating section includes a statistical amount calculating section that calculates a statistical amount of the first feature value, and
    the discriminating section discriminates the mucous membrane state on the basis of the statistical amount.

18. The medical image processing device according to claim 2, wherein the unit region setting section sets, as the unit region, the closed region and a belt-shaped region surrounding the closed region in the belt-like structure region.

\* \* \* \* \*